US009333334B2

(12) United States Patent
Jeffery et al.

(10) Patent No.: US 9,333,334 B2
(45) Date of Patent: May 10, 2016

(54) METHODS FOR ATTACHING AND WEARING A NEUROSTIMULATOR

(71) Applicant: thync, inc., Los Gatos, CA (US)

(72) Inventors: Douglas Jeffery, San Jose, CA (US); Isy Goldwasser, Los Gatos, CA (US); Wing Law, Cupertino, CA (US); Remi Demers, Saint-Nicolas (CA); Jay Frederick Hamlin, Santa Cruz, CA (US); Daniel Z. Wetmore, San Francisco, CA (US); Sumon K. Pal, Boston, MA (US); Jonathan Charlesworth, Boston, MA (US); William J. Tyler, Newton, MA (US)

(73) Assignee: thync, inc., Los Gatos, CA (US)

( * ) Notice: Subject to any disclaimer, the term of this patent is extended or adjusted under 35 U.S.C. 154(b) by 0 days.

(21) Appl. No.: 14/634,661

(22) Filed: Feb. 27, 2015

(65) Prior Publication Data

US 2015/0335876 A1 Nov. 26, 2015

Related U.S. Application Data

(63) Continuation-in-part of application No. 29/508,490, filed on Nov. 6, 2014, which is a continuation-in-part of application No. 29/513,764, filed on Jan. 5, 2015, which is a continuation-in-part of application No.29/517,629, filed on Feb. 13, 2015.

(Continued)

(51) Int. Cl.
*A61N 1/04* (2006.01)
(52) U.S. Cl.
CPC ............... *A61N 1/0492* (2013.01); *A61N 1/04* (2013.01)

(58) Field of Classification Search
CPC ........................... A61N 1/0476; A61N 1/0456
See application file for complete search history.

(56) References Cited

U.S. PATENT DOCUMENTS

| 4,431,000 A | 2/1984 | Butler et al. |
| 4,503,861 A | 3/1985 | Entrekin |

(Continued)

FOREIGN PATENT DOCUMENTS

| EP | 502919 B1 | 11/1993 |
| EP | 801957 A1 | 10/1997 |

(Continued)

OTHER PUBLICATIONS

Rossini et al.; Non-invasive electrical and magnetic stimulation of the brain, spinal cord and roots: basic principles and procedures for routine clinical application; Electroenceph. Clin. Neurophysiol.; 91(2); pp. 79-92; Aug. 1994.

(Continued)

*Primary Examiner* — Carl H Layno
*Assistant Examiner* — Jennifer Ghand
(74) *Attorney, Agent, or Firm* — Shay Glenn LLP

(57) ABSTRACT

Methods for attaching a wearable neurostimulator to a user's head (or head and neck) using a cantilever electrode apparatuses for neuromodulation. In practice an electrode assembly may mate with the wearable neuromodulation devices so that the device is worn over one portion of the electrode assembly while the rest of the electrode assembly attaches to another portion of the body. The neuromodulator may be worn on a portion of the electrode assembly in a cantilevered manner (e.g., held at one end while the opposite end is free-floating), which allows the rigid neuromodulation device to conform to a variety of user head sizes and shapes.

19 Claims, 23 Drawing Sheets

Related U.S. Application Data

(60) Provisional application No. 62/002,910, filed on May 25, 2014, provisional application No. 62/065,577, filed on Oct. 17, 2014, provisional application No. 62/076,459, filed on Nov. 6, 2014, provisional application No. 62/075,896, filed on Nov. 6, 2014, provisional application No. 62/099,950, filed on Jan. 5, 2015, provisional application No. 62/099,977, filed on Jan. 5, 2015.

(56) References Cited

U.S. PATENT DOCUMENTS

| | | |
|---|---|---|
| 4,638,436 A | 1/1987 | Badger et al. |
| 4,646,744 A | 3/1987 | Capel |
| 4,664,117 A | 5/1987 | Beck |
| 5,144,952 A | 9/1992 | Frachet et al. |
| 5,183,041 A | 2/1993 | Toriu et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,522,878 A | 6/1996 | Montecalvo et al. |
| 5,540,736 A | 7/1996 | Haimovich et al. |
| 5,573,552 A | 11/1996 | Hansjurgens |
| 5,578,065 A * | 11/1996 | Hattori et al. ............ 607/46 |
| 5,593,427 A | 1/1997 | Gliner et al. |
| 5,655,539 A | 8/1997 | Wang et al. |
| 6,324,432 B1 * | 11/2001 | Rigaux et al. ............ 607/62 |
| 6,445,955 B1 | 9/2002 | Michelson et al. |
| 6,463,328 B1 | 10/2002 | John |
| 6,526,318 B1 | 2/2003 | Ansarinia |
| 6,567,702 B1 | 5/2003 | Nekhendzy et al. |
| 6,623,430 B1 | 9/2003 | Slayton et al. |
| 6,731,987 B1 | 5/2004 | McAdams et al. |
| 6,983,184 B2 | 1/2006 | Price |
| 7,120,499 B2 | 10/2006 | Thrope et al. |
| 7,146,217 B2 | 12/2006 | Firlik et al. |
| 7,283,861 B2 | 10/2007 | Bystritsky |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 | 2/2010 | Castel et al. |
| 7,891,615 B2 | 2/2011 | Bevirt |
| 7,949,403 B2 | 5/2011 | Palermo et al. |
| 8,086,318 B2 | 12/2011 | Strother et al. |
| 8,097,926 B2 | 1/2012 | De Graff et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 8,380,315 B2 | 2/2013 | DeGiorgio et al. |
| 8,428,738 B2 | 4/2013 | Valencia |
| 8,494,627 B2 | 7/2013 | Bikson et al. |
| 8,506,469 B2 | 8/2013 | Dietrich et al. |
| 8,560,075 B2 | 10/2013 | Covalin |
| 8,639,343 B2 | 1/2014 | De Vos |
| 8,688,239 B2 | 4/2014 | Hartlep et al. |
| 8,843,210 B2 | 9/2014 | Simon et al. |
| 8,903,494 B2 | 12/2014 | Goldwasser et al. |
| 9,002,458 B2 | 4/2015 | Pal et al. |
| 9,014,811 B2 | 4/2015 | Pal et al. |
| 2002/0116036 A1 | 8/2002 | Daignault et al. |
| 2003/0060736 A1 | 3/2003 | Martin et al. |
| 2003/0225323 A1 * | 12/2003 | Kiani et al. ............ 600/323 |
| 2004/0015079 A1 | 1/2004 | Berger et al. |
| 2004/0098065 A1 | 5/2004 | Hagglof et al. |
| 2004/0267333 A1 | 12/2004 | Kronberg |
| 2005/0143677 A1 | 6/2005 | Young et al. |
| 2005/0165460 A1 | 7/2005 | Erfan |
| 2005/0267388 A1 * | 12/2005 | Hanna ............ 601/70 |
| 2007/0088419 A1 * | 4/2007 | Fiorina et al. ............ 607/152 |
| 2007/0173890 A1 | 7/2007 | Armstrong |
| 2007/0213790 A1 | 9/2007 | Nolan et al. |
| 2007/0276451 A1 | 11/2007 | Rigaux |
| 2007/0299370 A1 | 12/2007 | Bystritsky |
| 2008/0045882 A1 | 2/2008 | Finsterwald |
| 2008/0132974 A1 | 6/2008 | Strother et al. |
| 2008/0194965 A1 | 8/2008 | Sliwa et al. |
| 2008/0208266 A1 | 8/2008 | Lesser et al. |
| 2008/0215113 A1 | 9/2008 | Pawlowicz |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0099623 A1 | 4/2009 | Bentwich |
| 2009/0112098 A1 | 4/2009 | Vaezy et al. |
| 2009/0112133 A1 | 4/2009 | Deisseroth et al. |
| 2009/0112280 A1 | 4/2009 | Wingeier et al. |
| 2009/0177243 A1 | 7/2009 | Lebedev et al. |
| 2009/0210028 A1 * | 8/2009 | Rigaux et al. ............ 607/46 |
| 2009/0270947 A1 | 10/2009 | Stone et al. |
| 2009/0287108 A1 | 11/2009 | Levy |
| 2010/0042180 A1 * | 2/2010 | Mueller et al. ............ 607/46 |
| 2010/0049264 A1 | 2/2010 | Henke et al. |
| 2010/0057154 A1 | 3/2010 | Dietrich et al. |
| 2010/0145399 A1 | 6/2010 | Johari et al. |
| 2010/0256436 A1 | 10/2010 | Partsch et al. |
| 2010/0298623 A1 | 11/2010 | Mishelevich et al. |
| 2011/0029038 A1 | 2/2011 | Hyde et al. |
| 2011/0082326 A1 | 4/2011 | Mishelevich et al. |
| 2011/0082515 A1 | 4/2011 | Libbus et al. |
| 2011/0092800 A1 | 4/2011 | Yoo et al. |
| 2011/0093033 A1 | 4/2011 | Nekhendzy |
| 2011/0112394 A1 | 5/2011 | Mishelevich |
| 2011/0114191 A1 * | 5/2011 | Wheater et al. ............ 137/12 |
| 2011/0130615 A1 | 6/2011 | Mishelevich |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0178441 A1 | 7/2011 | Tyler |
| 2011/0178442 A1 | 7/2011 | Mishelevich |
| 2011/0190668 A1 | 8/2011 | Mishelevich |
| 2011/0190846 A1 | 8/2011 | Ruffini et al. |
| 2011/0196267 A1 | 8/2011 | Mishelevich |
| 2011/0208094 A1 | 8/2011 | Mishelevich |
| 2011/0213200 A1 | 9/2011 | Mishelevich |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270138 A1 | 11/2011 | Mishelevich |
| 2011/0270345 A1 | 11/2011 | Johnston et al. |
| 2011/0276112 A1 | 11/2011 | Simon et al. |
| 2011/0288610 A1 | 11/2011 | Brocke |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0046531 A1 | 2/2012 | Hua |
| 2012/0101366 A1 | 4/2012 | Ruohonen et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0185020 A1 | 7/2012 | Simon et al. |
| 2012/0209346 A1 | 8/2012 | Bikson et al. |
| 2012/0245653 A1 | 9/2012 | Bikson et al. |
| 2012/0283502 A1 | 11/2012 | Mishelevich et al. |
| 2012/0302912 A1 | 11/2012 | Moffitt et al. |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 * | 3/2013 | Akhadov et al. ............ 600/544 |
| 2013/0158627 A1 | 6/2013 | Gozani et al. |
| 2013/0184779 A1 | 7/2013 | Bikson et al. |
| 2013/0197401 A1 | 8/2013 | Sato et al. |
| 2013/0204315 A1 | 8/2013 | Wongsarnpigoon et al. |
| 2013/0226275 A1 | 8/2013 | Duncan |
| 2013/0267761 A1 | 10/2013 | Bentwich |
| 2013/0282095 A1 | 10/2013 | Mignolet et al. |

(56) References Cited

U.S. PATENT DOCUMENTS

| | | | |
|---|---|---|---|
| 2013/0318168 | A1 | 11/2013 | Demain et al. |
| 2013/0325096 | A1 | 12/2013 | Dupelle et al. |
| 2014/0031895 | A1 | 1/2014 | Rahimi et al. |
| 2014/0277324 | A1* | 9/2014 | DiUbaldi et al. ............ 607/139 |
| 2014/0336728 | A1 | 11/2014 | Franke et al. |
| 2015/0088224 | A1 | 3/2015 | Goldwasser et al. |

FOREIGN PATENT DOCUMENTS

| | | |
|---|---|---|
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/78834 A1 | 10/2001 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2010/047834 A1 | 4/2010 |
| WO | WO2010/067145 A1 | 6/2010 |
| WO | WO2011/057028 A1 | 5/2011 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156052 A1 | 11/2012 |
| WO | WO2013/071307 A1 | 5/2013 |
| WO | WO2013/192582 A1 | 12/2013 |

OTHER PUBLICATIONS

Pal et al.; U.S. Appl. No. 14/639,015 entitled "Transdermal electrical stimulation for modifying or inducing cognitive state," filed Mar. 4, 2015.

Pal et al.; U.S. Appl. No. 14/634,551 entitled "Methods for user control of neurostimulation to modify a cognitive state," filed Feb. 27, 2015.

Jeffery et al.; U.S. Appl. No. 14/634,664 entitled "Cantilever electrodes for transdermal and transcranial stimulation," filed Feb. 27, 2015.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Bachtold et al.; Focused ultrasound modifications of neural circuit activity in a mammalian brain; Ultrasound Med Biol; 24(4); 557-565; May 1998.

Breneman et al.; Piezo- and Flexoelectric Membrane Materials Underlie Fast Biological Motors in the Ear. Mat Res Soc Symp Proc; 1186E; Spring 2009 (author manuscript, 9 pgs.).

Bystritsky et al.; A review of low-intensity focused ultrasound pulsation. Brain stimulation; 4(3); 125-136; Jul. 2011.

Chaieb et al.; Transcranial alternating current stimulation in the low kHz range increases motor cortex excitability; Restor Neurol Neurosci; 29(3); pp. 167-175; Mar. 2011.

Dalecki, D.; Mechanical bioeffects of ultrasound. Annual review of biomedical engineering; 6; 229-248; Aug. 2004.

DaSilva et al.; Electrode positioning and montage in transcranial direct current stimulation; J Vis Exp; 51; e2744; 11 pgs.; May 2011.

Digitimer Ltd.; DS2 and DS3 Isolated Stimulator (product information); 2 pgs.; downloaded from http://www.digitimer.com/research/stimulators/index.htm on Feb. 10, 2014.

Electozyme; Company and Product Information; 3 pgs.; printed Feb. 11, 2014 from http://electrozyme.com/applications/.

Feurra et al.; Frequency specific modulation of human somatosensory cortex; Front Psychol; 2(13); 6 pgs.; Feb. 2011.

Garilov et al.; The effect of focused ultrasound on the skin and deep nerve structures of man and animal. Progress in brain research; 43; 279-292; 1976 (year of pub. sufficiently earlier than effective US filing date and any foreign priority date).

GoFlow; tDCS Kit; product information; 9 pgs..; printed Feb. 10, 2014 (http://flowstateengaged.com/).

Griesbauer et al.; Wave Propagation in Lipid Monolayers; Biophysical Journal; 97(10); 2710-2716; Nov. 2009.

Grindhouse Wetware; Thinking Cap; product information; 1 pg.; printed Feb. 10, 2014 (http://www.grindhousewetware.com/thinkingcap.html).

Heimburg, T.; Lipid ion channels. Biophysical chemistry; 50; pp. 2-22; Aug. 2010.

Hynynen et al.; 500-element ultrasound phased array system for noninvasive focal surgery of the brain: a preliminary rabbit study with ex vivo human skulls. Magnetic resonance in medicine; 52(1), 100-107; Jul. 2004.

Hynynen et al.; Clinical applications of focused ultrasound-the brain. International journal of hyperthermia ; 23(2), 193-202; Mar. 2007.

Kanai et al.; Frequency-dependent electrical stimulatioin of the visual cortex; Curr. Biol.; 18(23); pp. 1839-1843; Dec. 9, 2008.

Mihran et al.; Temporally-specific modification of myelinated axon excitability in vitro following a single ultrasound pulse. Ultrasound in Medicine & Biology; 16(3), 297-309; 1990 (year of pub. sufficiently earlier than effective US filing date and any foreign priority date).

Min et al.; Focused ultrasound-mediated suppression of chemically-induced acute epileptic EEG activity. BMC Neuroscience; 23, 12 pgs.; Mar. 2011.

Morris et al.; Lipid stress at play: Mechanosensitivity of voltage-gated channels; Mechanosensitive Ion Channels, B. Current Topics in Membranes; 59, Chapter 11; 297-338; 2007 (year of pub. sufficiently earlier than effective US filing date and any foreign priority date).

Morris et al.; Nav channel mechanosensitivity: activation and inactivation accelerate reversibly with stretch. Biophysical Journal; 93(3); 822-833; Aug. 2007.

O'Brien, Jr.; Ultrasound-biophysics mechanisms. Progress in biophysics and molecular biology; 93(1-3), pp. 212-255; Jan.-Apr. 2007 (author manuscript; 74 pgs.).

Paulus, W.; Transcranial electrical stimulation (tES-tDCS; tRNS, tACS) methods; Neuropsychol Rehabil.; 21(5); pp. 602-617; Oct. 2011.

Petrov et al.; Flexoelectric effects in model and native membranes containing ion channels; European biophysics journal; 22(4); pp. 289-300; Oct. 1993.

Prausnitz; The effects of electric current applied to skin: a review for transdermal drug delivery; Advanced Drug Delivery Reviews; vol. 18; pp. 395-425; Feb. 8, 1996.

Rinaldi et al.; Modification by focused ultrasound pulses of electrically evoked responses from an in vitro hippocampal preparation. Brain Research; 558(1); pp. 36-42; Aug. 1991.

Saiote et al.; High-frequency TRNS reduces BOLD activity during visuomotor learning; PLOS one; 8(3); e59669; 8 pgs.; Mar. 2013.

Schutter et al.; Brain oscillations and frequency-dependent modulation of cortical excitability; Brain Stimulation; 4(2); pp. 97-103; Apr. 2011.

Shealy et al.; Reversible effects of ultrasound on spinal reflexes; Archives of neurology; 6; pp. 374-386; May 1962.

STD Pharmaceutical Products; Idrostar intophoresis machine (product and use information); 9 pgs.; Dec. 2011 (printed Feb. 11, 2014 from http://www.iontophoresis.info/instructions/).

Sukharev et al.; Mechanosensitive channels: multiplicity of families and gating paradigms. Sci STKE; vol. 2004; p. re4 (24 pgs.); Feb. 2004.

ter Haar; Therapeutic applications of ultrasound. Prog Biophysics Mol Biol; 93; pp. 111-129; Jan.-Apr. 2007.

(56) References Cited

OTHER PUBLICATIONS

Terney et al.; Increasing human brain excitability by transcranial high-frequency random noise stimulation; The Journal of Neuroscience; 28(52); pp. 14127-14155; Dec. 2008.

Tsui et al.; In vitro effects of ultrasound with different energies on the conduction properties of neural tissue; Ultrasonics; 43; pp. 560-565; Jun. 2005.

Tufail et al.; Transcranial pulsed ultrasound stimulates intact brain circuits; Neuron; 66, pp. 681-694; Jun. 2010.

Tufail et al.; Ultrasonic neuromodulation by brain stimulation with transcranial ultrasound. Nature protocols; 6(9); pp. 1453-1470; Sep. 2011.

Turi et al.; Both the cutaneous sensation and phosphene perception are modulated in a frequency-specific manner during transcranial alternating current stimulation; Restor. Neurol. Neurosci.; 31(3); pp. 275-285; 2013 (year of pub. sufficiently earlier than effective US filing date and any foreign priority date).

Tyler et al.; U.S. Appl. No. 61/663,409 entitled "Device and Methods for Noninvasive Neuromodulation Using Targeted Transcranial Electrical Stimulation," filed Jun. 22, 2012.

Tyler et al.; U.S. Appl. No. 61/550,334 entitled "Improvement of Direct Communication," filed Oct. 21, 2011.

Tyler et al; Remote excitation of neuronal circuits using low-intensity, low-frequency ultrasound. PLoS ONE; 3(10); e3511; pp. 1-11; Oct. 2008.

Velling et al.; Modulation of the functional state of the brain with the aid of focused ultrasonic action; Neuroscience and behavioral physiology; 18; pp. 369-375; Sep.-Oct. 1988.

Vickery et al.; Ubiquity and Specificity of Reinforcement Signals throughout the Human Brain. Neuron; 72; pp. 166-177; Oct. 2011.

Yang et al.; Transcranial ultrasound stimulation: a possible therapeutic approach to epilepsy. Medical Hypotheses; 76(3); pp. 381-383; Mar. 2011.

Yoo et al.; Focused ultrasound modulates region-specific brain activity; NeuroImage; 56(3); pp. 1267-1275; Jun. 2011.

Yoo et al.; Transcranial focused ultrasound to the thalamus alters anesthesia time in rats; NeuroReport; 22(15); pp. 783-787; Oct. 2011 (author manuscript; 9 pgs.).

Zaghi et al.; Noninvasive brain stimulation with low-intensity electrical currents: putative mechanisms of action for direct and alternating current stimulation; Neuroscientist; 16(3); pp. 285-307; Jun. 2010 (pre-pub version; 24 pgs.).

Goldwasser et al.; U.S. Appl. No. 14/715,461 entitled "Wearable transdermal neurostimulator having cantilevered attachment," filed May 18, 2015.

Charlesworth et al.; U.S. Appl. No. 14/715,476 entitled "Methods and apparatuses for amplitude-modulated ensemble waveforms for neurostimulation," filed May 18, 2015.

Demers et al.; U.S. Appl. No. 14/715,483 entitled "Methods and apparatuses for control of a wearable transdermal neurostimulator to apply ensemble waveforms," filed May 18, 2015.

Demers et al.; U.S. Appl. No. 14/715,470 entitled "Transdermal neurostimulator adapted to reduce capacitive build-up," filed May 18, 2015.

Coutinho et al.; Musical emotions: predicting second-by-second subjective feelings of emotion from low-level psychoacoustic features and physiological measurements; Emotion; 11(4); pp. 921-937; Aug. 2011.

Gracenote; Timeline-metadata-api; 3 pages; retrieved from the internet Jul. 7, 2015; (https://github.com/gracenote/timeline-metadata-api/blob/master/README.md).

\* cited by examiner

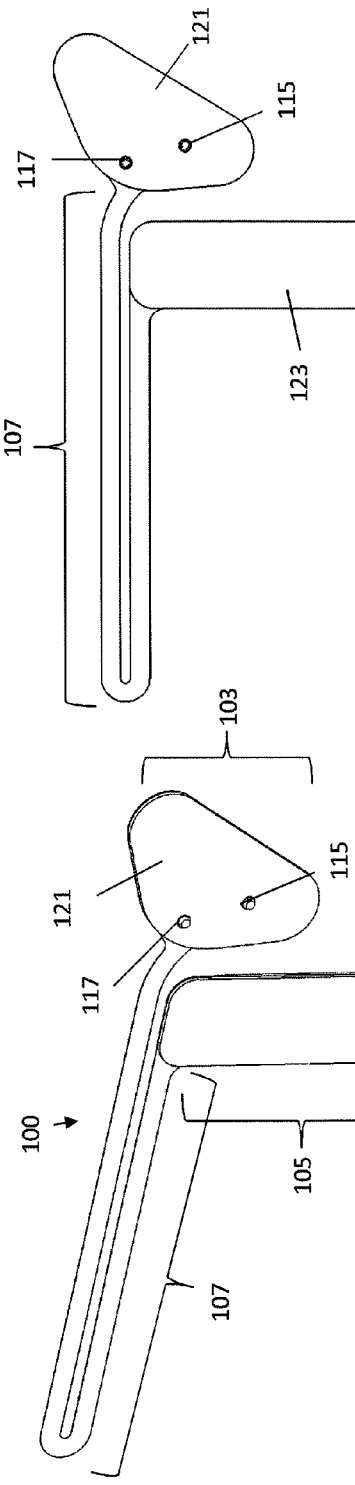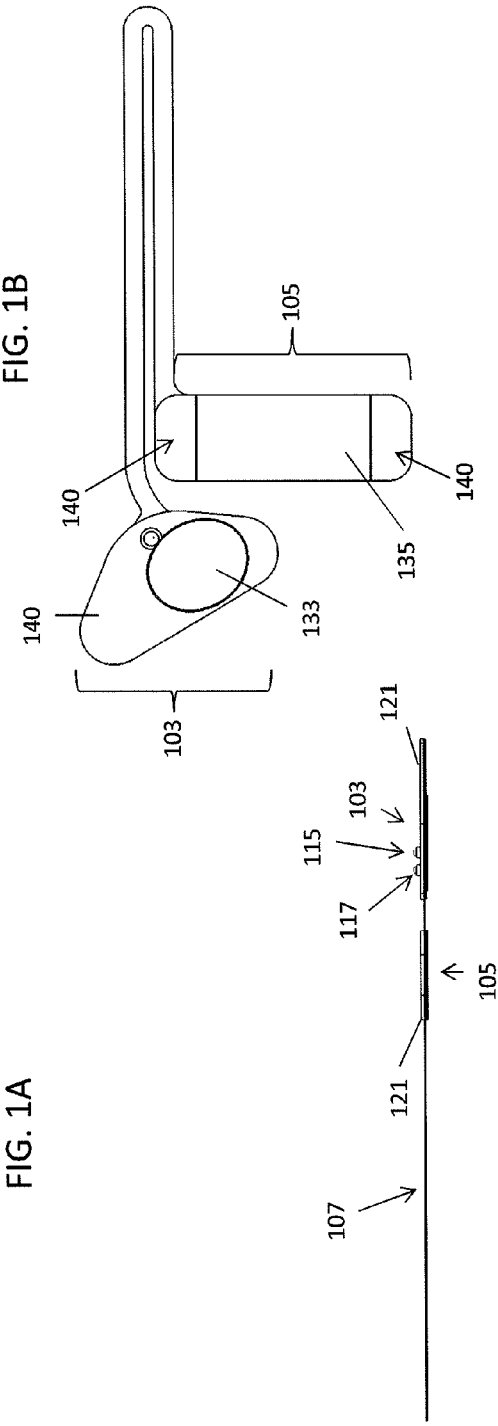

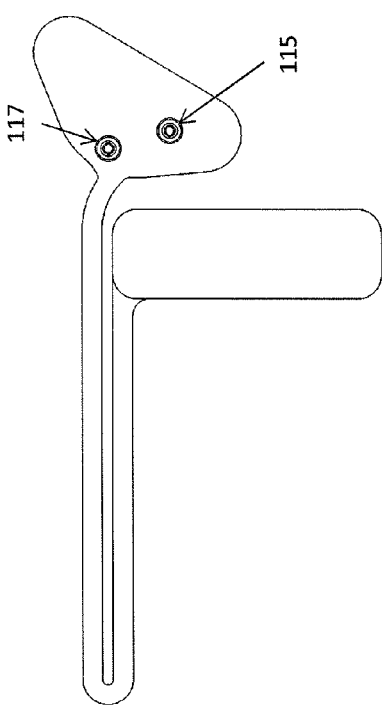
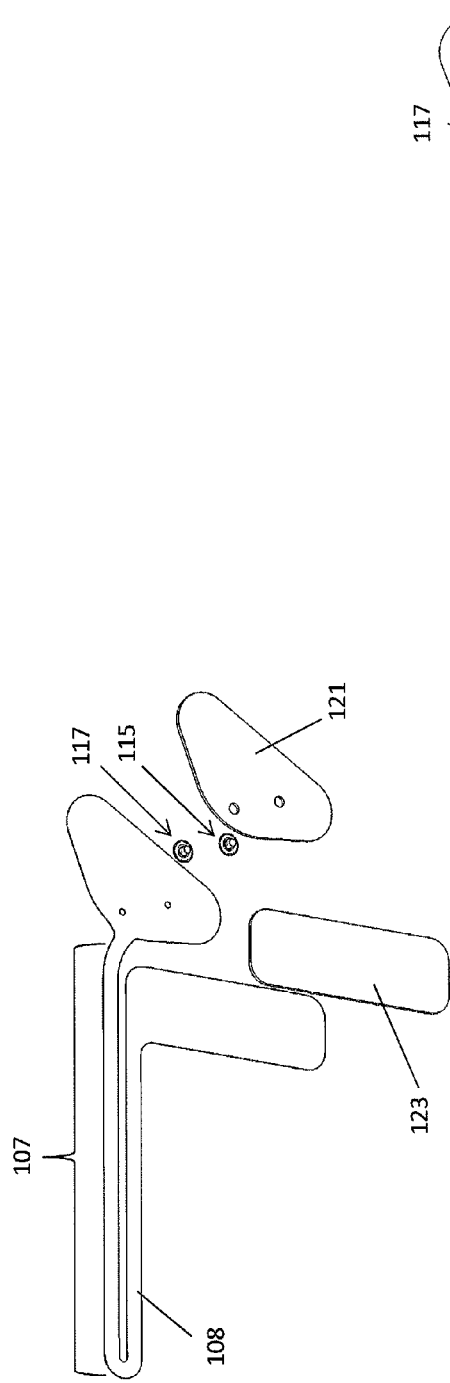
FIG.2A
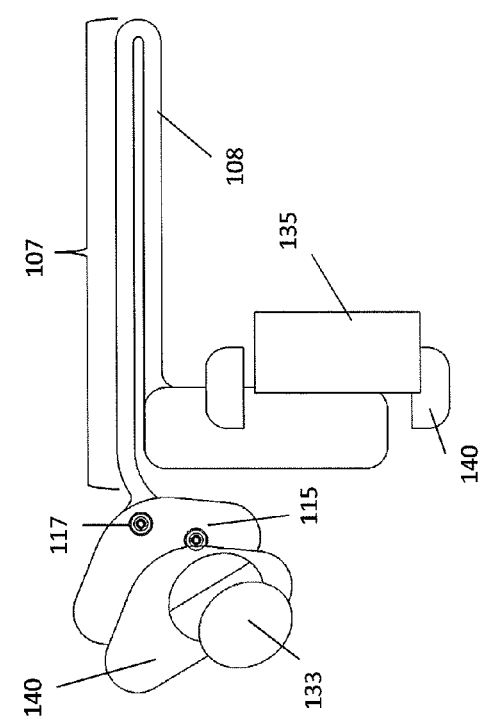
FIG. 2B
FIG. 3

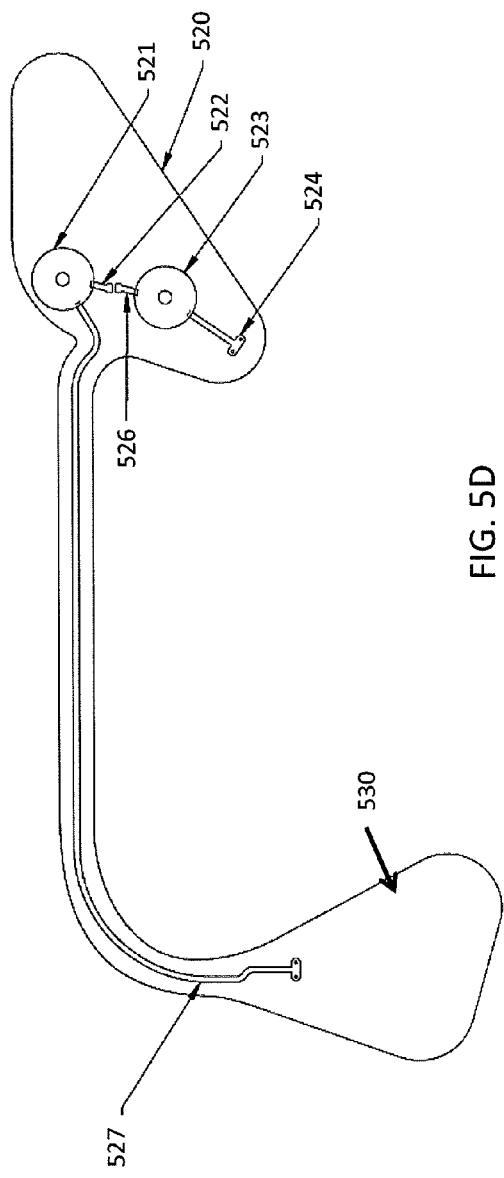
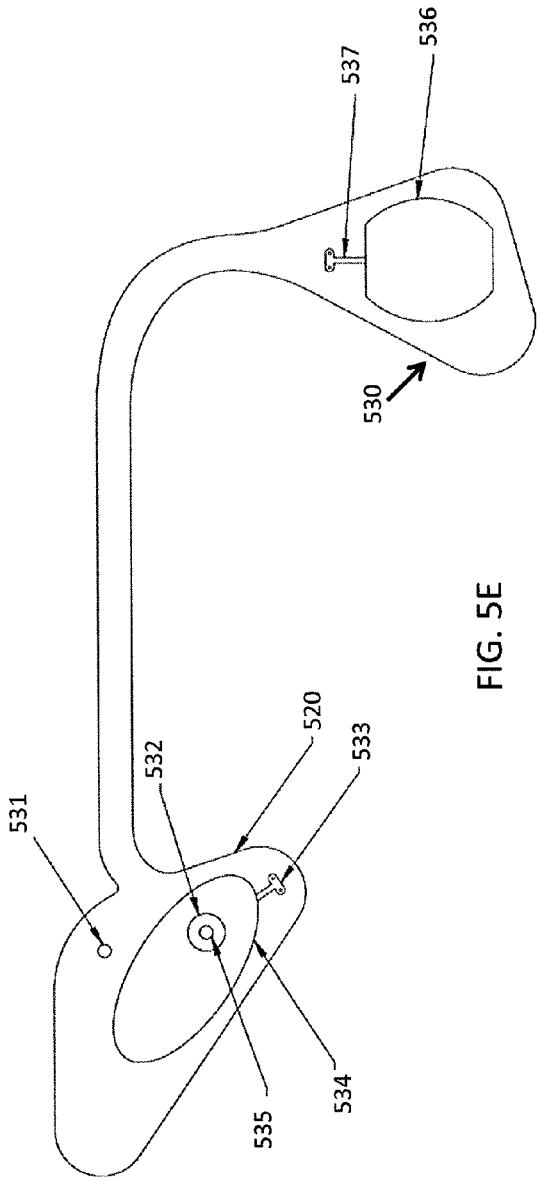
FIG. 5D
FIG. 5E

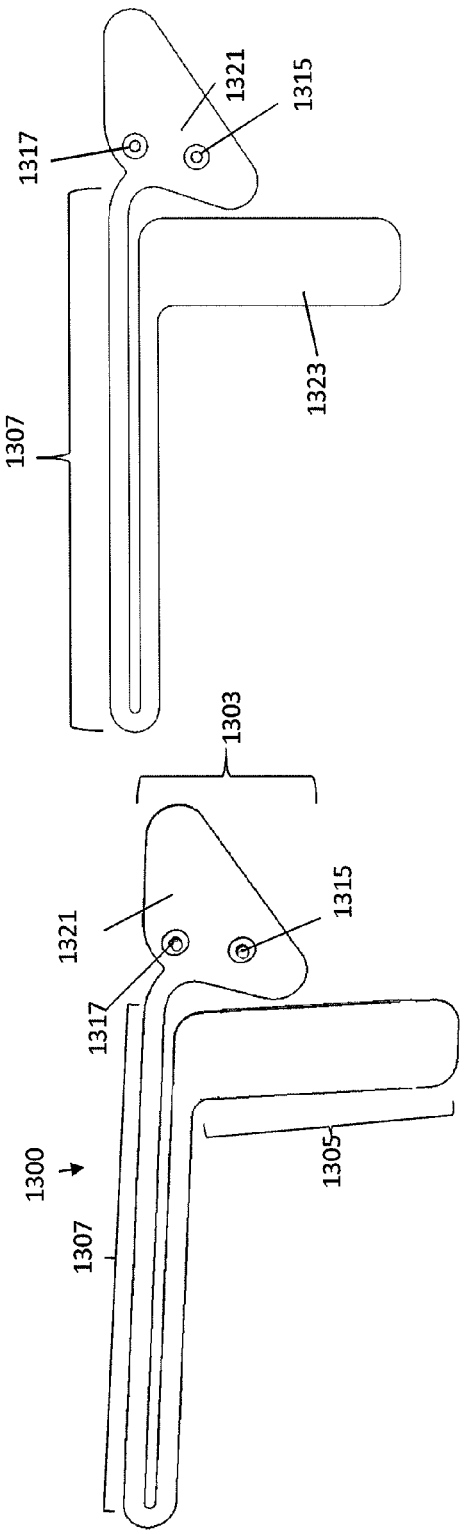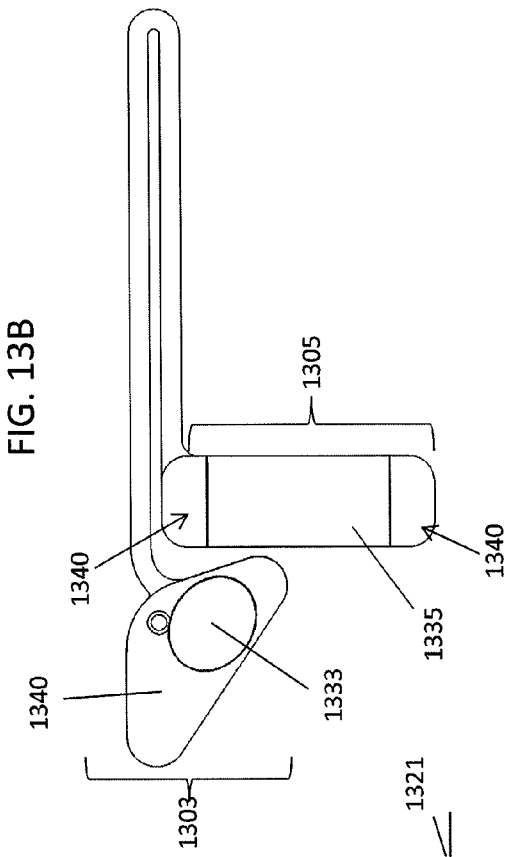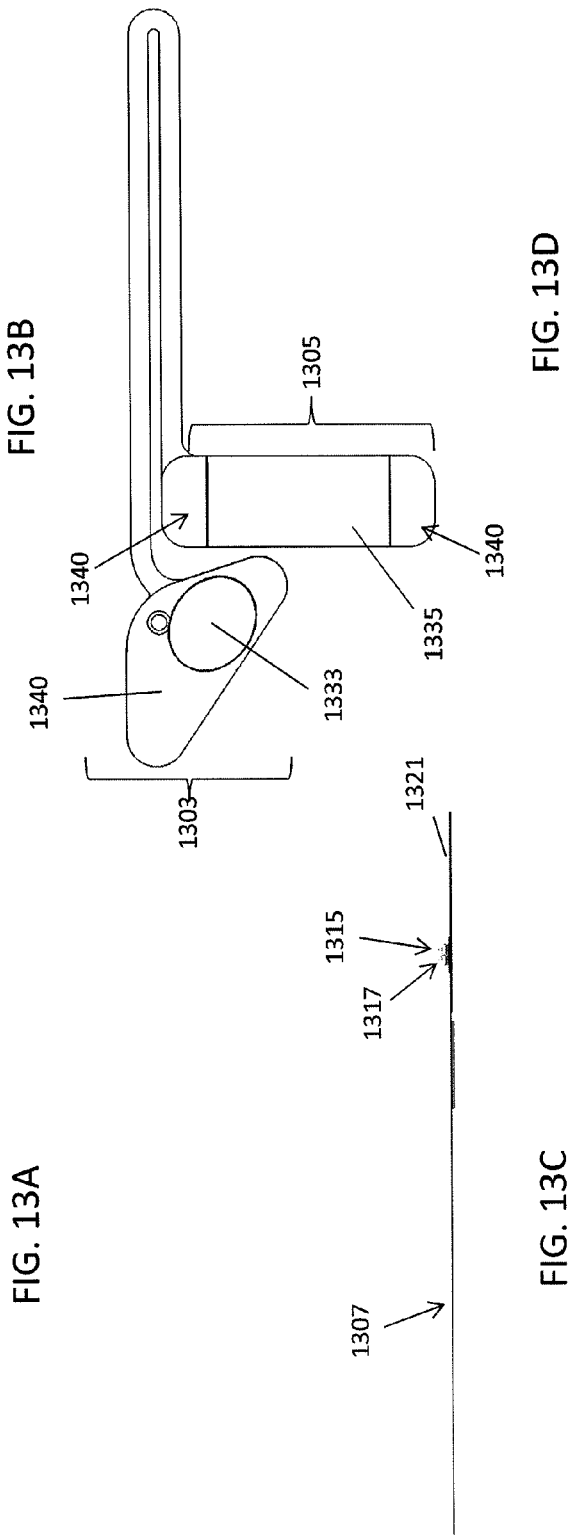
FIG. 13A
FIG. 13B
FIG. 13C
FIG. 13D

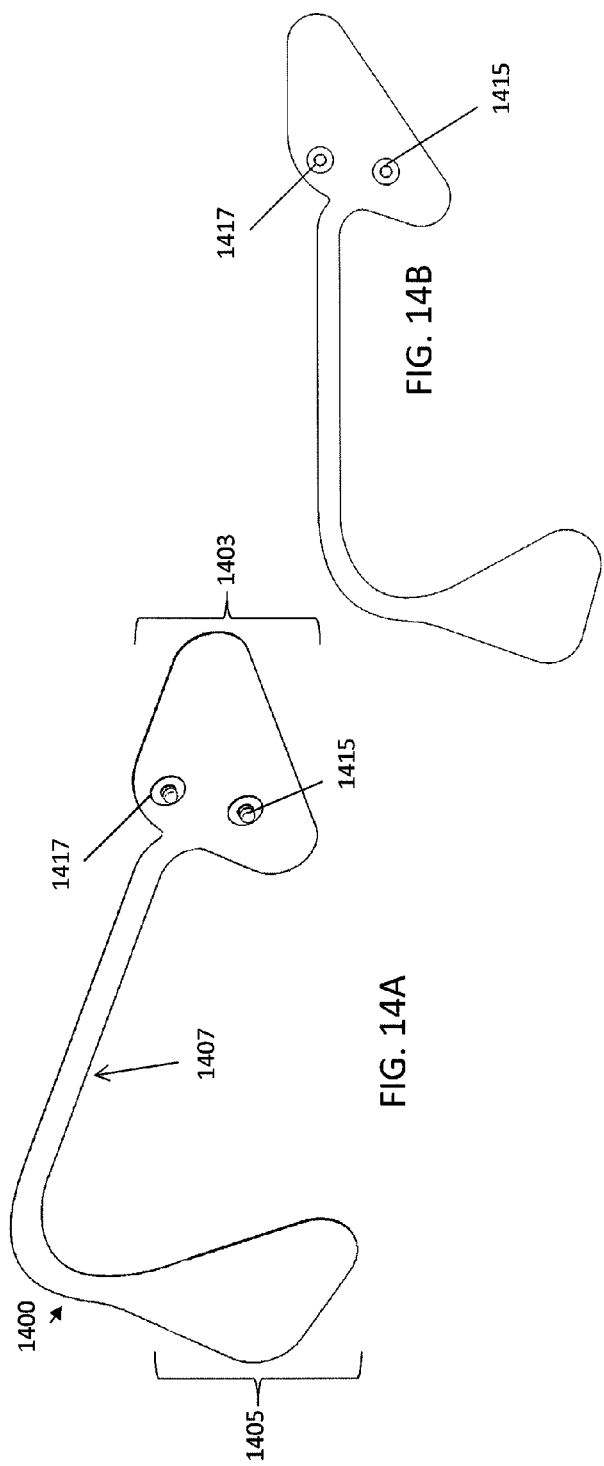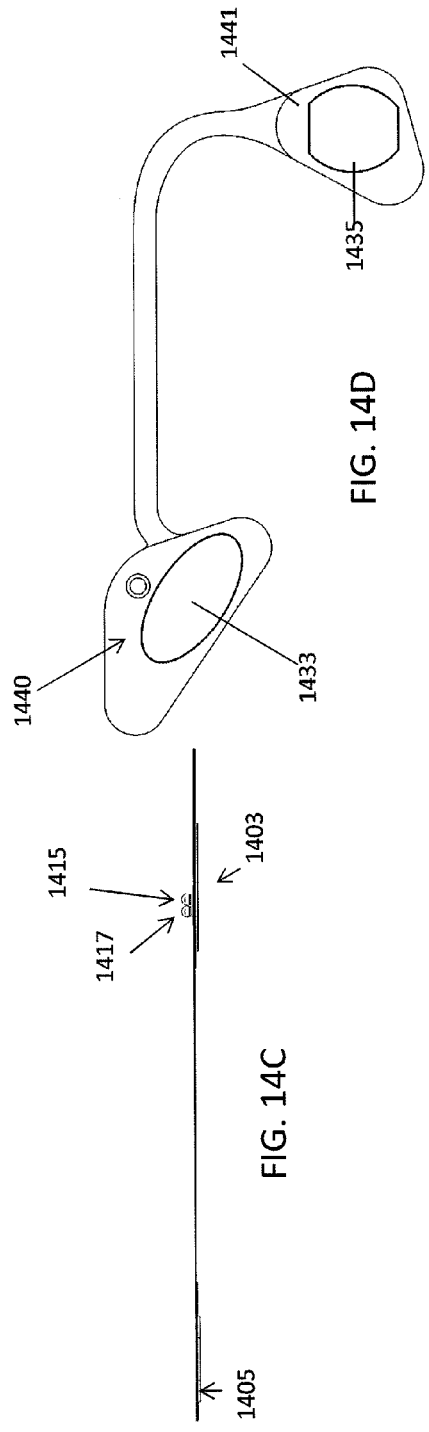
FIG. 14A FIG. 14B FIG. 14C FIG. 14D

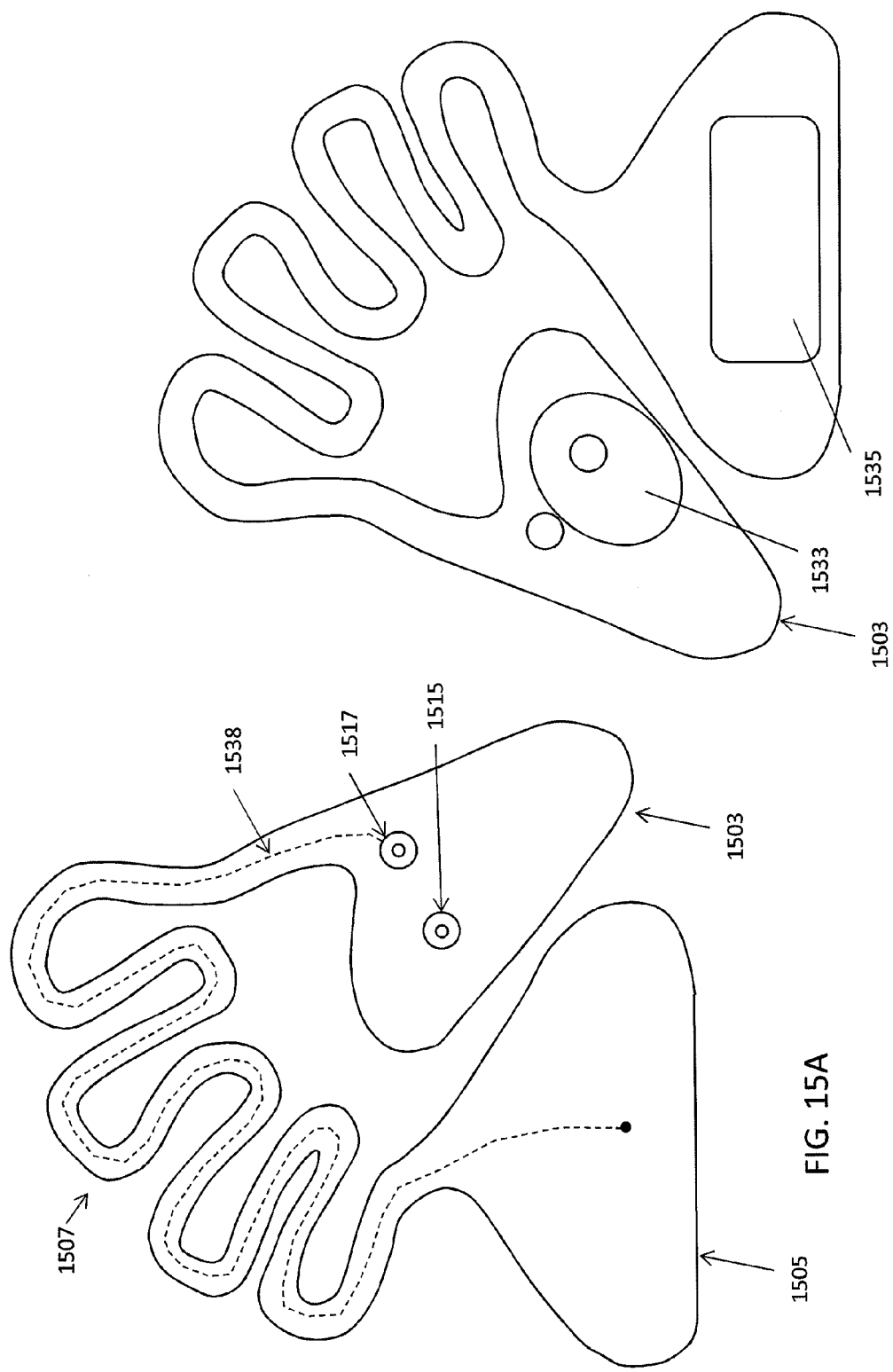

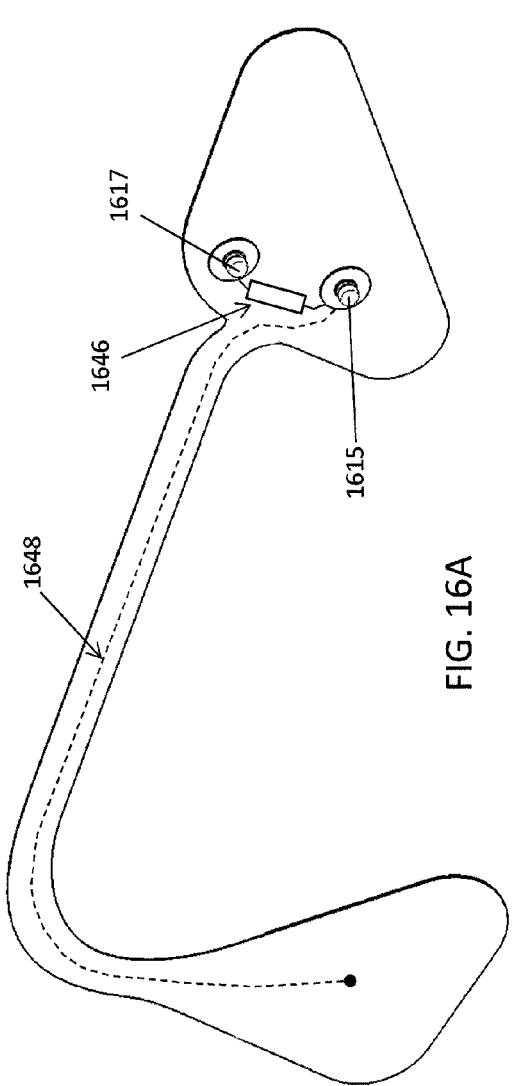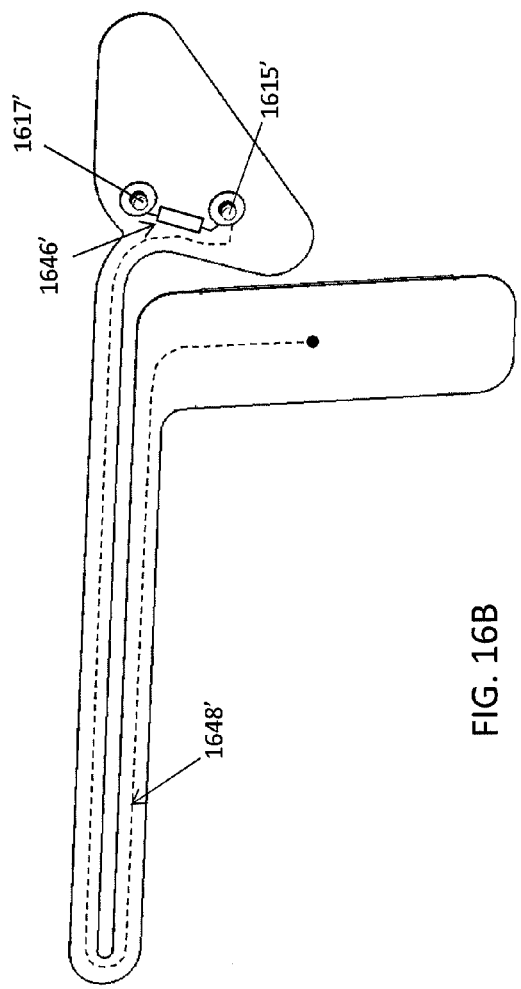
FIG. 16A
FIG. 16B

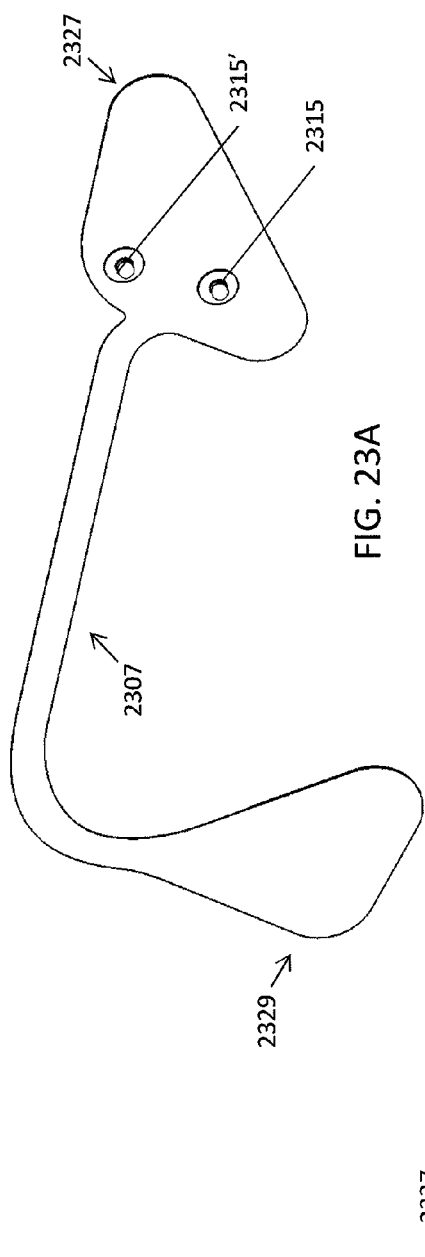
FIG. 23A
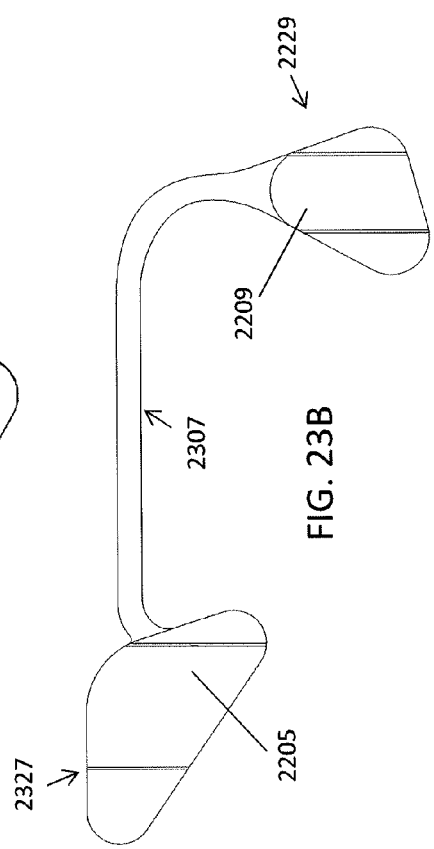
FIG. 23B
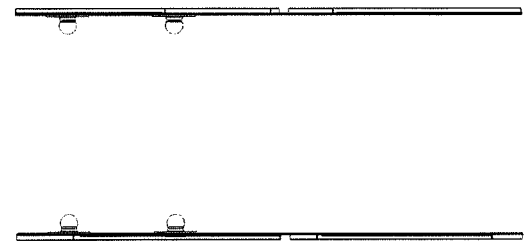
FIG. 23E    FIG. 23F
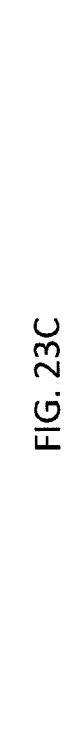
FIG. 23C
FIG. 23D

METHODS FOR ATTACHING AND WEARING A NEUROSTIMULATOR

CROSS REFERENCE TO RELATED APPLICATIONS

This application claims priority to each of: U.S. Provisional Patent Application No. 62/002,910, titled "TRANSDERMAL ELECTRICAL STIMULATION ELECTRODE DEGRADATION DETECTION SYSTEMS AND METHODS OF USING THEM," and filed on May 25, 2014; U.S. Provisional Patent Application No. 62/065,577, titled "FLEXIBLE ELECTRODE DEVICES FOR TRANSDERMAL AND TRANSCRANIAL ELECTRICAL STIMULATION,"and filed on Oct. 17, 2014; U.S. Provisional Patent Application No. 62/076,459, titled "CANTILEVER ELECTRODES FOR TRANSDERMAL AND TRANSCRANIAL STIMULATION," and filed on Nov. 6, 2014; U.S. Provisional Patent Application No. 62/075,896, titled "SYSTEMS AND METHODS FOR NEUROMODULATION," and filed on Nov. 6, 2014; U.S. Provisional Patent Application No. 62/099.950, title "CANTILEVER ELECTRODES FOR TRANSDERMAL AND TRANSCRANIAL STIMULATION," and filed on Jan. 5, 2015; and U.S Provisional Patent Application No. 62/099,977, titled "FLEXIBLE ELECTRODE DEVICES FOR TRANSDERMAL AND TRANSCRANIAL ELECTRICAL STIMULATION," and filed on Jan. 5, 2015. Each of these applications is herein incorporated by reference in its entirety. This application is also a continuation-in-part of the following design patent applications: U.S. Design Patent Application No. 29/508,490, titled "ELECTRODE ASSEMBLY FOR TRANSDERMAL AND TRANSCRANIAL STIMULATION," AND FILED ON Nov. 6, 2014; U.S. Design Patent Application No. 29/513,764, titled "ELECTRODE ASSEMBLY FOR TRANSDERMAL AND TRANSCRANIAL STIMULATION," and filed on Jan. 5, 2015; and U.S. Design Patent Application No. 29/517,629, titled "ELECTRODE ASSEMBLY FOR TRANSDERMAL AND TRANSCRANIAL STIMULATION," and filed on Feb. 13, 2015, All of these applications are herein incorporated by reference in their entirety.

This application may be related to one or more of U.S.patent application Nos. 14/091,121, titled "WEARABLE TRANSDERMAL ELECTRICAL STIMULATION DEVICES AND METHODS OF USING THEM," filed on Nov. 26, 2013, now U.S. Pat. No. 8,903,494; U.S. patent application No. 14/320,443, titled "TRANSDERMAL ELECTRICAL STIMULATION METHODS FOR MODIFYING OR INDUCING COGNITIVE STATE," filed on Jun. 30, 2014, now U.S. Pat. No. 9,014,811; and U.S. patent application No. 14/320,461, titled "TRANSDERMAL ELECTRICAL STIMULATION DEVICES FOR MODIFYING OR INDUCING CONGNITIVE STATE," filed on Jun. 30, 2014, now U.S. Pat. No. 9,002,458. Each of these reference is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are noninvasive neuromodulation apparatuses, including devices and systems, and methods of using them. In particular described herein are electrode apparatuses (including cantilever electrode apparatuses) that may be attached to a wearable neurostimulator (neuromodulator) and worn on a user's head and/or neck and used for electrical stimulation to modulate the user's cognitive state.

BACKGROUND

Noninvasive neuromodulation technologies that affect neuronal activity can modulate and potentially alter behavior, cognitive states, perception, and motor output without requiring an invasive procedure. To date, the majority of transdermal non-invasive neuromodulatory devices apply electrical energy to a subject's skin using one or more electrodes that typically attach to the neurostimulator via a cord or cable, which can be long and awkward to wear, particularly in a non-clinical or non-research setting.

For example, transcranial and/or transdermal electric stimulation (hereinafter "TES") using scalp electrodes has been used to affect brain function in humans in the form of transcranial alternating current stimulation (hereinafter "tACS"), transcranial direct current stimulation (hereinafter "tDCS"), cranial electrotherapy stimulation (hereinafter "CES"), and transcranial random noise stimulation (hereinafter "tRNS"). Systems and methods for TES have been disclosed (see for example, Capel U.S. Pat. No. 4,646,744; Haimovich et al. U.S. Pat. No. 5,540,736; Besio et al. U.S. Pat. No. 8,190,248; Hagedorn and Thompson U.S. Pat. No. 8,239,030; Bikson et al. U.S. Patent Application Publication No. 2011/0144716; and Lebedev et al. U.S. Patent Application Publication No. 2009/0177243). tDCS systems with numerous electrodes and a high level of configurability have been disclosed (see for example Bikson et al. U.S. Patent Application Publication Nos. 2012/0209346, 2012/0265261, and 2012/0245653).

TES has been used therapeutically in various clinical applications, including treatment of pain, depression, epilepsy, and tinnitus. Despite the research to date on TES neuromodulation, existing systems and methods for delivering TES are lacking. In particular, systems having electrodes that are effective, comfortable, and easy-to-use, e.g., easy to apply and remove, particularly in a non-clinical (e.g., home) setting, have been lacking.

Most electrical stimulation systems targeting the nervous system incorporate a tabletop or handheld hardware comprising a user interface, electrical control circuitry, a power supply (e.g. battery), wires leading to electrodes affixed to a user, and predetermined and/or preconfigured electrical stimulation protocols. Conventional systems are limited regarding the comfort, design, and use of electrodes to deliver TES waveforms. For example, they may use uncomfortable and inflexible electrodes, such that the electrodes do not conform to the body of the user, resulting in uneven impedance, increased irritation during stimulation, and reduced cognitive effects. Further, most prior art electrodes are not well suited to attach to a wearable neurostimulator so that the neurostimulator is held to the body by the electrode.

Although a handful of small, lightweight and presumably wearable neuromodulation devices have been described, none of these systems include electrodes (e.g., disposable electrodes) for applying energy to a patient's head or head and having a cantilevered body that securely attaches to a small and wearable lightweight neurostimulator. Thus, there is a need for lightweight, wearable neuromodulation systems, and in particular for electrodes that reliably connect to such neuromodulation devices and contact two or more widely separated regions of the wearer's body, including the head or head and neck.

Further, there is a need for neurostimulators that use a variety of electrode configurations adapted for particular uses. Specifically, there is a need for electrode apparatuses (systems and devices) that can be automatically detected and/or identified by the neurostimulator. It would also be beneficial to provide neurostimulators and electrode apparatuses for use with reusable neurostimulators that are capable of detecting use and detecting and/or indicating when the electrode should be replaced.

It would be beneficial to provide one or more electrode apparatuses that include a pH regulating consumptive layer that is flexible and can make reliable electrical contact with the user's skin. Finally, it would also be useful to provide electrode assemblies that are capable of making reliable and durable electrical contact with the user's skin while allowing somewhat more forgiving attachment and/or support of a typically rigid wearable neurotransmitter.

Described herein are apparatuses (e.g., devices and systems), and methods that may address at least the needs identified above.

SUMMARY OF THE DISCLOSURE

Described herein are wearable neuromodulation devices configured to be worn on a subject's head or on the subject's head and neck. Also described herein are cantilever electrodes for use with the wearable neuromodulation devices. The cantilever electrodes may be configured to mate with the wearable neuromodulation devices to form a neuromodulation system. The neuromodulation systems described herein may also be referred to as neurostimulation systems, neurostimulator systems, neuromodulator systems, applicator systems, neuromodulation applicator systems, or the like.

The wearable neuromodulation devices described herein are small, lightweight and specifically adapted to be conforming to the subject so that they can be worn while the subject goes about their daily activities. In particular, these devices are adapted to be worn on the subject's head (e.g., at the temple region) comfortably even while wearing headgear such as hats, glasses, hoods, scarves, or the like. These devices typically have a first surface (subject-facing surface) that has a curved and twisted shape so that an electrode on the surface conforms to a subject's temple region. The thickness of the device (measured from the first surface) is typically thinner at one end and thicker at the other end. The thinner end region may be configured to be oriented relative to the subject's eye, with the thicker region worn higher on the subject's head, toward the center of the subject's forehead. The neuromodulation devices described herein are also configured to include attachments to the cantilever electrodes on the underside (e.g., the first surface), providing electrical connection to at least two electrodes on the cantilever electrode assembly. These neuromodulation devices may also be referred to as neurostimulation devices, neurostimulators, neuromodulators, applicators, neuromodulation applicators, electrical stimulators, or the like.

A cantilever electrode may also be referred to as an electrode assembly, electrode pad, electrode system, or electrode apparatus, may be durable or disposable, and is generally configured to connect to the neuromodulation device and apply energy (e.g., current) from the neuromodulation device to the subject's skin to modulate a subject's cognitive state (e.g., calming, invigorating, etc.) or other cognitive function. The cantilevered electrodes described herein are configured to attach to a subject's body and to connect to a wearable neurostimulator so that the neurostimulator is held to the body by the electrode (electrode assembly). As used herein, the term "cantilever" or "cantilevered" in reference to the electrodes and/or neurostimulators generally refers to electrodes that are configured to mechanically connect to a wearable neurostimulator at one or more (e.g., two) locations that are off-center relative to the patient-facing surface of the neurostimulator, and are typically near an end region or edge region of either or both the patient-facing surface of the neurostimulator and the outward-facing side of the electrode assembly. This will typically result in a mechanical connection between the neurostimulator and the electrode body that is pinned at one end region, holding one end or end region of the neurostimulator fixed to the electrode (and therefore the body when worn by a user) but not the other. Thus, in some variations, the portion of the neurostimulator that is opposite from the connection(s) to the electrode assembly may move relative to the electrode assembly, or may move closer or further from the user's skin when the device is worn. Thus, the cantilevered attachment arrangement described herein has the benefit of allowing a rigid body of a neurostimulator to adjust to different skin surface shapes and curves, since the attachment at one end region will allow a limited hinge-like movement relative to the end region that is mechanically connected to the electrode body. In reference to the electrode assemblies described herein, the electrode assemblies may have a relatively long, flat body (e.g., an elongate body) and may have a length that is greater than a few inches long (e.g., greater than 2 inches, greater than 3 inches, greater than 4 inches, greater than 5 inches, e.g., from a first region of electrical contact to the next nearest region of electrical contact); the connections to the wearable neurostimulator may all be located at or near one end region of the electrode assembly, such as over or adjacent to (though on the opposite face of the electrode assembly from) one of the regions of electrical contact.

For example, described herein are electrode apparatuses for use with an electrical stimulator to be worn on a subject's head. In general, these electrode apparatuses include two electrical connections on one end region (which may be mechanical connectors such as snap connectors or the like) for connecting to the electrical stimulator. The position of these electrical connectors may be between about 0.6 and 0.9 inches from center-to-center. This distance has been found to be sufficient to both allow electrical isolation when connecting to different active regions of the electrode apparatus, while also providing sufficient mechanical support and/or tolerance to the cantilever electrode when it is connected to the electrical stimulator and then worn by a subject.

The cantilever electrode apparatuses described herein are generally elongated, thin bodies that include a first active region for applying electrical energy to a subject's skin at or near one end region, and a second active region for applying electrical energy to another region of a subject's skin at or near a second end region. The electrical connectors to connect to the electrical stimulator are typically both at or near one end region of the elongate body. The first and second active regions on the body may be connected by an elongated portion that is typically greater than 2 inches long. In some variations the elongate body is stiff or relatively rigid (though it may be ductile or include a ductile region that can be bent to set a shape). In some variations the elongate body has a limited flexibility, e.g., so that it is flexible in a first axis (e.g., an x-axis) but is not flexible in a second axis (e.g., y-axis), and may be rotated. For example, the elongate body of the electrode apparatus may be formed of a sheet of material such as a flex circuit material.

As used herein, when a component is described as being at an end region of another component, it should be understood that the first component is not limited to being at the extreme end of other component, but may be adjacent to or near the absolute end or edge of the other component. For example, the first component may be within 20% or less of the total length of the other component from an edge or absolute end of the other component. In contrast, when a component is described as being at the end or edge of another component, the first component may be at or immediately adjacent to the absolute end or edge of the other component.

For example, an electrode apparatus may include: a first electrode portion having a front side and a back side; a first active region on the front side that is configured to deliver energy to the subject's skin; a first connector extending proud from the back side, wherein the first connector is in electrical communication with the first active region; a second connector extending proud from the back side, wherein the first and second connectors are separated by between about 0.7 and about 0.8 inches from center to center; a second electrode portion separated from the first electrode portion by an elongate body region extending at least two inches between the first electrode portion and the second electrode portion; and a second active region on a front side of the second electrode portion that is in electrical communication with the second connector and is configured to deliver energy to the subject's skin.

As used herein, an electrode portion may refer to a region of the electrode assembly that includes, on one surface, an electrically active region that is, for example, configured as a cathodic or anodic region, and may also include surrounding non-electrically active regions including, for example, adhesive for holding the electrically active region to the skin of the user. The electrically active region may include multiple sub-regions that may be electrically activated together or as subsets, as described in detail below. An electrode portion may also include a surface that is opposite from the surface with the electrically active region; in some examples this opposite surface may include one or more contacts for making electrical and/or mechanical contact with a wearable neurostimulator. Other electrode portions may not include contacts, but may be connected (e.g., by electrical trace(s)) to contacts that are present at other locations on the electrode assembly. An electrode portion may be a sub-region of the substrate forming the electrode assembly, for example, at an end region of the substrate. In some variations the electrode portion is a discrete region of the electrode assembly (which may include two or more such electrode portions).

As mentioned, the first and second conductors are typically configured to electrically connect the apparatus to the electrical stimulator. For example, the first and second connectors may be snap connectors. The first and second connectors may be integrated to form a single connector unit with at least two separate conductive paths between the neurostimulator and the electrode apparatus. The connectors may provide mechanical as well as electrical connection to the electrical stimulator. The connectors may hold (or assist in holding) the cantilever electrode apparatus to the electrical applicator. Alternatively or additionally, the electrode apparatus may include a mechanical fastener configured to secure the electrode apparatus to the electrical stimulator. In some variations the connectors are sufficient to secure the electrode apparatus to the electrical stimulator. In some variations an adhesive may be used between the electrode apparatus and the electrical applicator (e.g., neurostimulator) to secure the cantilever electrode apparatus to the electrical applicator. For example, the apparatus may include an adhesive on the back side of the first flat electrode portion configured to hold the electrode apparatus to the electrical stimulator. In some variations, a magnet and ferromagnetic material are used to couple the electrode apparatus to the neurostimulator instead of or in addition to a mechanical connector. In general, the first and second connectors are configured to electrically connect the electrode apparatus to the electrical stimulator.

As mentioned above, the elongate body region between the first and second electrode portions (and the first and second active regions) may be flexible in a first direction but not flexible in a direction normal to the first direction. For example, the elongate body region may be formed of a strip of material such as a flex circuit material. Examples of flex circuit materials are well known, including, for example, polymers such as polyester (PET), polyimide (PI), polyethylene napthalate (PEN), Polyetherimide (PEI), various fluoropolymers (FEP) and copolymers.

In general, the electrode apparatus may be substantially flat. For example, the thickness of the electrode apparatus may have an overall thickness (e.g., thickness of the substrate, and layers printed, silk-screened or otherwise adhered onto the substrate) that is less than 5 mm, less than 4 mm, less than 3 mm, less than 1 mm, less than 0.9 mm, less than 0.8 mm, less than 0.7 mm, less than 0.6 mm, etc., and extend in a plane (that may be bent or curved). The connectors may extend proud of this overall thickness. In addition, the electrode portions may extend above/below this overall thickness.

In any of the variations described herein the electrode apparatus may include an electrically conductive gel over the first active region and/or the second active region. The conductive gel may be adhesive and/or it may be surrounded by an additional adhesive for securing the active region to the subject's skin. For example, the electrode apparatus may include an adhesive on the front side of the first electrode portion and/or on the front side of the second electrode portion.

In some variations the electrode apparatus includes a foam region. For example, the apparatus may include a foam on the first electrode portion. The foam may help comfortably seat the first active region against the subject's skin, and may also provide spacing between the apparatus and the subject's skin so that the electrode apparatus coupled to the neurostimulator conforms more closely to curved portions of a subject's body that may vary from person to person.

Both the first and second connectors are typically adjacent to each other on the back side of the first electrode portion, though separated by a distance sufficient to allow tolerance and support, as mentioned above. In some variations the first connector is behind the first active region and the second connector is not behind the first active region.

The first active region of the first electrode portion may be positioned off-center on the first electrode portion.

The apparatus may generally include a thin (e.g., flat) and flexible elongate body having a front side and a back side, wherein the first electrode portion is at or near a first end region of the flexible elongate body and wherein the second flat electrode portion is at or near a second end region of the flexible elongate body and the elongate body region extends between the first and second active regions. The elongate body may be greater than two inches long (e.g., greater than 3 inches long, greater than 4 inches long, etc.). In some variations the elongate body is curved or bent (when not flexed). For example, the elongate body may have a bend in it or other out-of-plane structure or rigidity.

In some variations the elongate body region may include an electrical trace on a flexible elongate substrate. The electrical trace may be printed or otherwise applied onto (or embedded in) the substrate. For example, the trace may be flexographically printed, silk screened, or laser printed using conductive ink.

The electrical trace may provide the electrical connection between the second connector and the second active region of the second electrode portion.

An electrode apparatus for use with an electrical stimulator to be worn on a subject's head may include: a flat and flexible elongate body having a front side and a back side; a first electrode portion at or near a first end region of the elongate body; a first active region on the front side of the first electrode portion, wherein the first active region is configured to deliver energy to the subject's skin; a first connector extending proud from behind the back side of the first electrode portion, wherein the first connector is in electrical communication with the first active region; a second connector extending proud from the back side of the first electrode portion; a second electrode portion at or near a second end region of the elongate body that is separated from the first electrode portion by at least two inches; and a second active region on the front side of the second electrode portion that is in electrical communication with the second connector and is configured to deliver energy to the subject's skin; wherein the first and second connectors are configured to electrically connect the apparatus to the electrical stimulator.

As mentioned, the first and second connectors are configured to electrically connect the apparatus to the electrical stimulator, and may be, for example, snap connectors.

As mentioned above, the electrode apparatus may include an electrically conductive gel (e.g., over the first active region and/or the second active region), an adhesive on the front side of the first electrode portion and on the front side of the second electrode portion, a foam on the first flat electrode portion, or the like. In any of the electrode apparatuses described herein the first and second connectors may be separated by between about 0.6 to about 0.9 inches (e.g., about 0.7 to about 0.8 inches, about 0.72 inches, etc.).

A flexibly connected electrode apparatus for use with an electrical stimulator to be worn on a subject's head may include: a flat and flexible elongate body having a front side and a back side; a first electrode portion at a first end region of the elongate body; a first active region on the front side of the first electrode portion, wherein the first active region is configured to deliver energy to the subject's skin; a first connector extending proud from the back side of the first electrode portion behind the first active region, wherein the first connector is in electrical communication with the first active region; a second connector extending proud from behind the back side of the first electrode portion, wherein the first and second connectors are separated by between about 0.7 and about 0.8 inches; a second electrode portion at a second end region of the elongate body; and a second active region on the front side of the second electrode portion that is in electrical communication with the second connector and is configured to deliver energy to the subject's skin; wherein the first and second snap connectors are configured to electrically connect the apparatus to the electrical stimulator.

Also described herein are methods of applying the electrode apparatuses to a subject, and methods of applying electrical stimulation to a subject using any of these electrode apparatuses. For example, a method of applying electrical stimulation to a subject's head (or head and neck) using a flat elongate electrode apparatus coupled to a wearable electrical stimulator may include: connecting a first and second electrical connector of the electrode apparatus to the wearable electrical stimulator by inserting the first electrical connector into a first receptacle on an underside of the wearable electrical simulator and a second electrical connector of the electrode apparatus into a second receptacle on the underside of the wearable electrical stimulator, wherein the first and second electrical connectors extend proud of a back side of a first active region of the electrode apparatus; adhesively securing the electrode apparatus coupled to the electrical stimulator to the subject's head so that the first active region on a front side of the electrode apparatus is in electrical contact with the subject's head; and adhesively securing a second active region on the front side of the electrode apparatus at a second location on the subject's head or neck wherein the second active region is separated from the first electrode portion through a flat and flexible elongate body (though the first and second active regions may be on the same substrate) with the second active region is electrically connected to the second electrical connector. The method may also include adhesively securing the back side of the first active region to the underside of the wearable electrical stimulator.

The method may also include applying energy from the wearable electrical stimulator between the first and second active regions. For example, the method may include applying current from the wearable electrical simulator having a peak current of at least 3 mA, a frequency above 640 Hz, and a duty cycle of greater than about 10%. For example, the method may include applying current of at least 5 mA or greater, e.g., having a maximum for the waveform ensemble of between about 5 mA and about 25 mA, a maximum dominant frequency of between about 750 Hz and 15 kHz, and a duty cycle between about 20-70%, etc., where the waveform is biphasic and asymmetric, and in some variations includes a transient 'short' or discharge within the repeated waveform(s).

Adhesively securing the electrode apparatus coupled to the electrical stimulator may comprise securing the first active region and the wearable electrical stimulator to the subject's temple. For example, with the active region lateral and/or slightly above the subject's eye. In some variations, adhesively securing the second active region comprises securing the second active region to the subject's neck or a region behind the subject's ear (e.g., in the mastoid region, e.g., on or near the mastoid). Connecting the first and second electrical connectors may comprise connecting the first and second electrical connectors wherein the first electrical connector is between about 0.7 and 0.8 inches from the second first electrical connector.

In general, adhesively securing a second active region comprises bending the flat and flexible elongate body around the subject's head to position the second active region on the subject's head or neck (e.g., on the back of the subject's neck or behind the subject's ear on or near the mastoid region).

Methods of wearing an electrode apparatus may include: connecting a first and second electrical connector of the electrode apparatus to a wearable electrical stimulator by inserting the first electrical connector into a first receptacle on an underside of the wearable electrical simulator and a second electrical connector of the electrode apparatus into a second receptacle on the underside of the wearable electrical stimulator, wherein the first and second electrical connectors extend proud of a back side of a first active region of the electrode apparatus; adhesively securing the electrode apparatus coupled to the electrical stimulator to the subject's head so that the first active region on a front side of the electrode apparatus is in electrical contact with the subject's head; and adhesively securing a second active region on the front side of the electrode apparatus at a second location on the subject's head or neck wherein the second active region is connected to the first active region through a flat and flexible elongate body so that the second active region is electrically connected to the second electrical connector.

In some variations, two or more electrical connectors are connected to a multi-pin receptacle on the neurostimulator. For example a single mechanical connector may be used having two or more electrical connectors.

The method may also include adhesively securing the back side of the first active region to the underside of the wearable electrical stimulator.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is a perspective view of a first variation of an electrode apparatus as described herein.

FIGS. 1B, 1C and 1D show front, top and back views, respectively of the cantilever electrode apparatus of FIG. 1A.

FIG. 2A is an exploded view of the front of the cantilever electrode apparatus similar to that shown in FIG. 1B.

FIG. 2B is an exploded view of the back of the cantilever electrode apparatus similar to that shown in FIG. 1D.

FIG. 3 is an alternative front view of a cantilever electrode apparatus similar to the apparatus shown in FIG. 1B, in which a foam pad is not included over the front of the first electrode region.

FIG. 5D is a front view of the variation shown in FIG. 5C that may be worn so that a first electrode active region is positioned on a user's temple region on a first (e.g., right or left) side of the body while a second electrode active region is positioned on the user's mastoid region.

FIG. 5E is a back view of the cantilever electrode apparatus of FIG. 5D.

FIGS. 13A-13D show perspective, front, top and back views, respectively of another variation of a cantilever electrode apparatus.

FIGS. 14A-14D show perspective, front, top and back views, respectively of another variation of a cantilever electrode apparatus.

FIGS. 15A and 15B show to and bottom views, respectively, or another variation of a cantilever electrode.

FIG. 16A is a perspective view of a variation of a cantilever electrode apparatus having a detectable electrical element between the first and second electrodes that can be sensed by a neurostimulator.

FIG. 16B is another example of a perspective view of a cantilever electrode apparatus having a detectable electrical element between the first and second electrodes that can be sensed by a neurostimulator.

FIG. 18A is a top view showing traces connecting through the substrate (shown in FIG. 18B) to multiple sub-regions forming an active region of the electrode on the bottom surface, shown in FIG. 18C.

FIG. 22A is a front perspective view, FIG. 22B is a back view, FIGS. 22C and 22D show top and bottom views, respectively, and FIGS. 22E and 22D show left and right views, respectively.

FIG. 23A-23F illustrate another variation of a cantilevered electrode assembly similar to the one shown in FIGS. 4A-4D and 5A, in which the two electrode skin-contacting portions (connected by the flexible elongate body region) are oriented differently than shown in FIG. 4A-4D; the active regions of the electrode skin-contacting portions extend from edge-to-edge of a central region of both electrode skin-contacting portions. FIG. 23A is a front perspective view, FIG. 23B is a back view, FIGS. 23C and 23D show top and bottom views, respectively, and FIGS. 23E and 23D show left and right views, respectively.

DETAILED DESCRIPTION

Figure 4A:
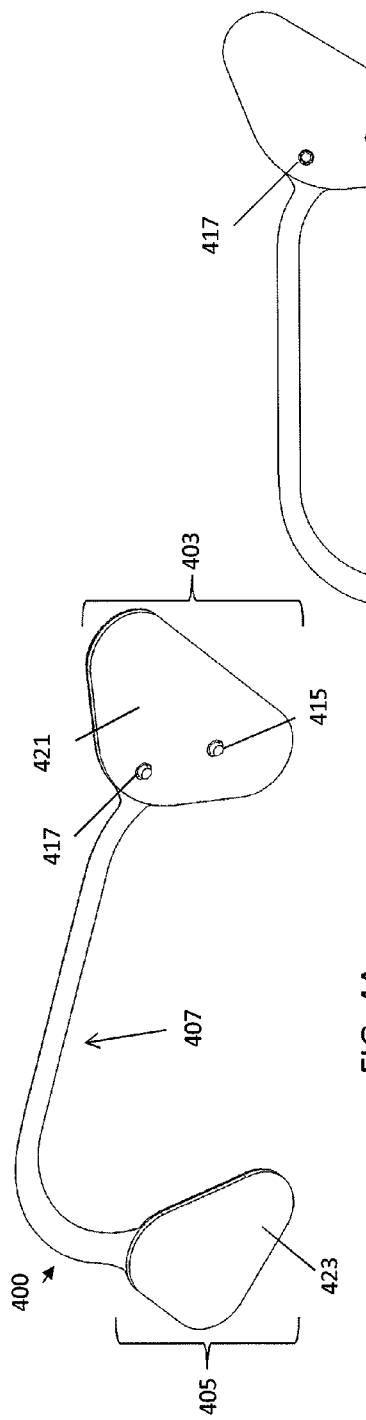
FIG. 4A is a perspective view of a variation of an electrode apparatus as described herein.
Figure 4C:
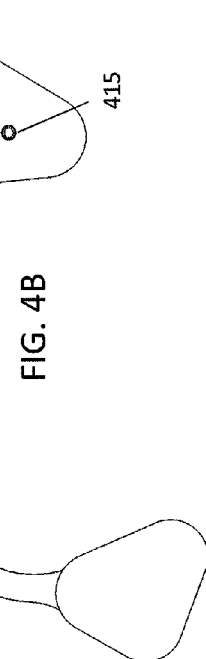
FIGS. 4B, 4C and 4D show front, top and back views, respectively of the cantilever electrode apparatus of FIG. 4A.
Figure 4B:
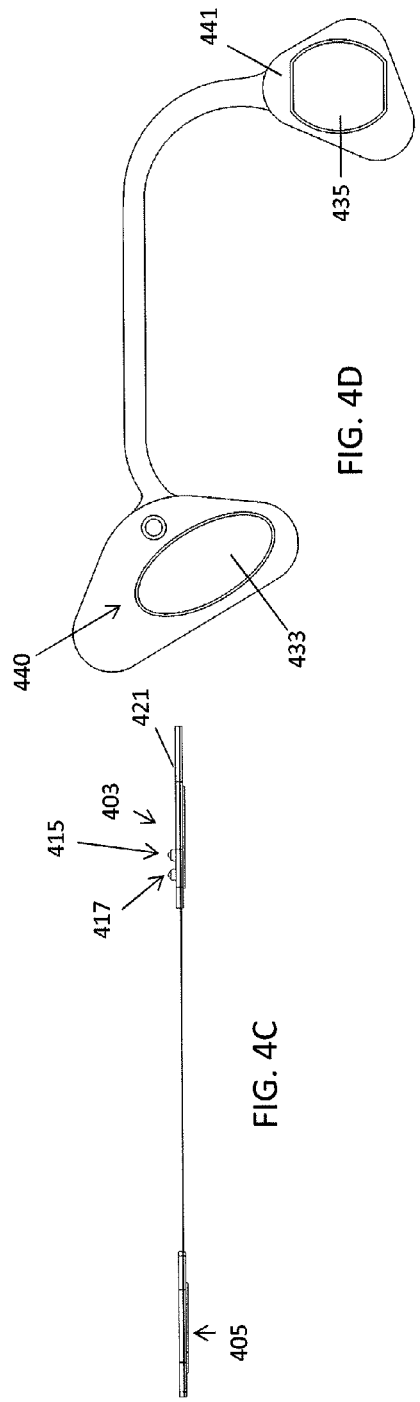
Figure 4D:
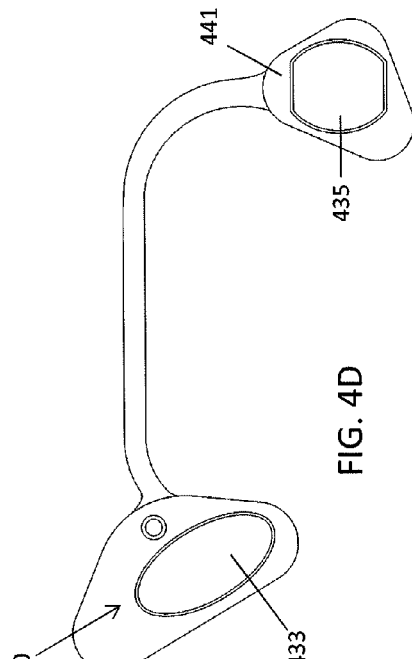

In general, described herein are cantilever electrode apparatuses, systems including them, and methods of wearing and using them to deliver neurostimulation/neuromodulation to a subject. The cantilever electrode apparatuses described herein may act as an interface between a wearable, lightweight and self-contained neurostimulator ("electrical stimulator") and a subject's body, particularly the head or head and neck region, where stimulation is to be applied. These cantilever electrode apparatuses may be disposable (or semi-disposable) components (and may be recyclable or semi-recyclable) that are connected to the neurostimulator and applied directly to the subject; energy (typically current) from the neurostimulator is guided and delivered to the subject by the cantilever electrode apparatus. Although the neurostimulator may be small and lightweight, the cantilever electrode apparatus may allow it to secure to the subject's body and deliver energy to two or more regions on the body (e.g., temple, neck, chest, etc.) that are separated by a distance that is much greater than the size of the neurostimulator.

Although the majority of the electrode apparatuses described herein are configured for use with a wearable neurostimulator that is attached in a cantilevered manner to the electrode assembly, these electrode assemblies are not limited to this use, but may also find use with non-wearable or partially wearable electrical stimulators. For example, a neurostimulator may couple to the connectors of the electrode apparatuses described herein by attaching one or more wires that then connect to a portable or desktop neurostimulator.

System Description

In general, a neurostimulation system as described herein may include at least two parts: (1) a lightweight, wearable, neurostimulator device (neurostimulator) that is configured to be worn on the head; and (2) a consumable/disposable electrode assembly. There may be multiple configurations (e.g., shapes) of the electrode assembly, and, as described in greater detail herein, the electrode assembly may generally be formed on a flexible material ('flex circuit' material) and mechanically and electrically connected to the neurostimulator. In some variations a third component may be a controller that is separate from but communicates with the neurostimulator. For example, in some variations the controller may be a user device that wirelessly communicates with the neurostimulator. In some variations the controller is a mobile telecommunications device (e.g., smartphone or tablet) being controlled by an application that sends instructions and exchanges 2-way communication signals with the neurostimulator. For example, the controller may be software, hardware, or firmware, and may include an application that can be downloaded by the user to run on a wireless-connectable (i.e. by Bluetooth) device (e.g., handheld device such as a smartphone or tablet) to allow the user to select the waveforms delivered by the neurostimulator, including allowing real-time modulation of the delivered neurostimulation to modify the user's cognitive state as described herein.

For example the system can be operated to induce either "calm" states of mind or "energetic" states of mind. Operating the system to induce a state of increased energy can be alternatively described as one or more of: enhancing focus and attention; enhancing alertness; increasing focus and/or attention; enhancing wakefulness; increasing subjective feeling of energy; increasing objective physiological energy levels; increasing motivation; increasing physiological arousal; and evoking a physical sensation of warmth in the subject's chest. Operating the system to induce a state of enhancing a calm or relaxed mental state can be alternatively described as one or more of: a state of calm within about 5 minutes of starting a TES session; a care-free state of mind; a mental state free of worry; induction of sleep; facilitating falling asleep; a perception of slowing of a passage of time; muscular relaxation; enhanced concentration; inhibition of distractions; increased cognitive clarity; increased sensory clarity; a dissociated state; a mild intoxication; a euphoric state; a relaxed state; enhanced enjoyment of auditory and visual experiences; reduced physiological arousal; increased capacity to handle emotional or other stressors; a reduction in psychophysiological arousal associated with changes in the activity of the hypothalamic-pituitary-adrenal axis; a reduction in biomarkers of stress, anxiety, and mental dysfunction; anxiolysis; a state of mental clarity; enhanced physical performance; resilience to stress; a physical sensation of relaxation in the periphery; and a perception of feeling the heart beat.

For example, to induce energy, the electrode apparatus may be attached to the user's temple and behind the user's ear (e.g., mastoid region). To induce calm, the electrodes may be attached to the user's temple and the back of the user's neck. In both examples, the neurostimulator may apply an ensemble waveform for about 5-30 min (or longer) that is made up of different "blocks" having repeated waveform characteristics; the waveform ensemble may include transition regions between the different blocks. In general, at least some of the waveform blocks (and in some variations most or all of them) generally have a current amplitude of >5 mA (e.g., between 5 mA and 40 mA, between 5 mA and 30 mA, between 5 mA and 22 mA, etc.), and a frequency of >750 Hz (e.g., between 750 Hz and 25 kHz, between 750 Hz and 20 kHz, between 750 Hz and 15 kHz, etc.), the current is typically biphasic and is charge imbalanced, and has a duty cycle of between 10-99% (e.g., between 20-95%, between 30-80%, between 30-60%, etc.). One or more of these characteristics may be changed during stimulation over timescales of every few seconds to minutes.

Figure 8B:
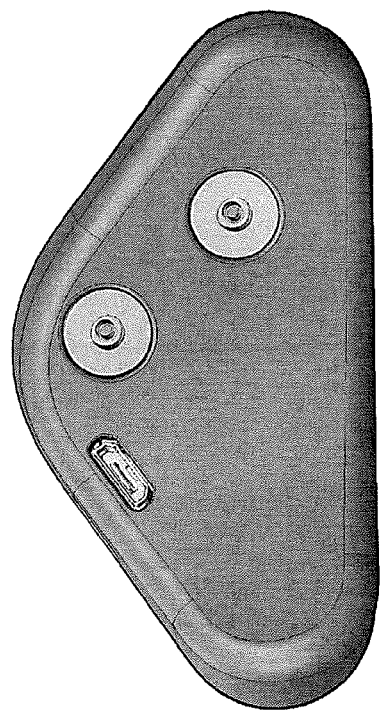
FIG. 8B is a back perspective view of a neurostimulation device similar to the device shown in FIGS. 7A-7F.
Figure 8A:
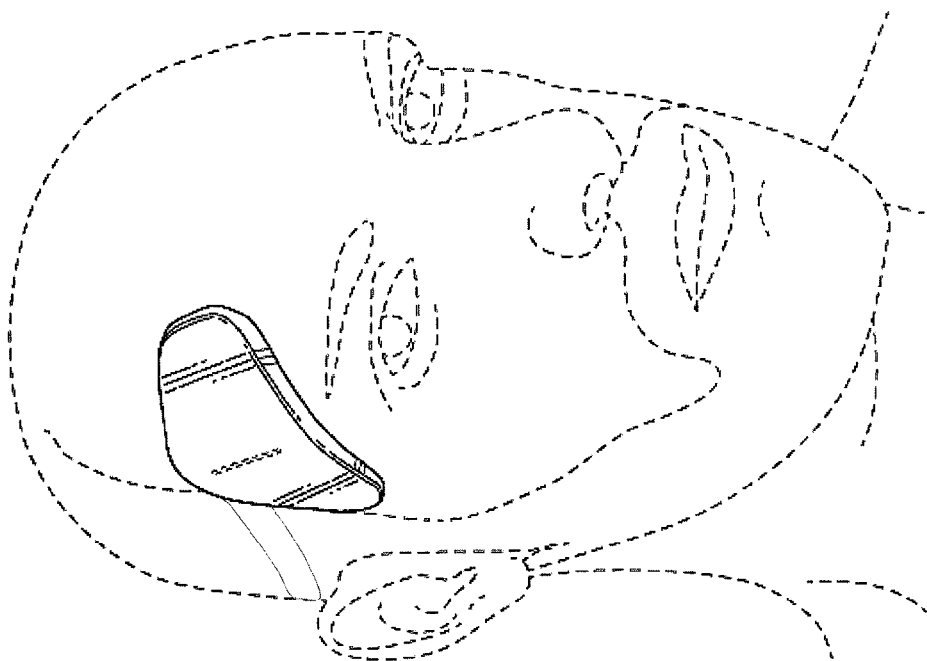
FIG. 8A illustrates the neurostimulation device shown in FIGS. 7A-7F worn with a cantilever electrode apparatus on a subject.

When worn, the system may resemble the system shown in FIG. 8A, having an electrode assembly attached at two locations (points or regions) on the subject's head and/or neck) and a neurostimulator attached to the electrode assembly, as shown; in some variations a separate controller may be attached to coordinate the application of stimulation.

As will be described in greater detail herein, the neurostimulator may be lightweight (e.g., less than 30 g, less than 25 g, less than 20 g, less than 18 g, less than 15 g, etc.), and self-contained, e.g. enclosing the circuitry, power supply, and wireless communication components such as a rechargeable battery and charging circuit, Bluetooth chip and antenna, microcontroller, current source configured to deliver waveforms with a duration of between 10 seconds and tens of minutes. A neurostimulator may also include safety circuitry. The neurostimulator may also include circuits to determine that the electrode is attached and what "kind" of electrode it is (i.e., for the calm or the energy mode; or indicating the batch and/or source of manufacture). FIGS. 7A-7F and 8B illustrate one variation of a neurostimulator.

A neurostimulator may be contoured so that it fits on or near the right temple/forehead area of a subject and may conform thereto. As will be described in greater detail herein, the electrode assembly may mechanically and/or electrically connect to the neurostimulator, e.g., by snapping to the underside of the neurostimulator at one or more (e.g., two) connectors such as snap receivers. Thus in some variations the neurostimulator may be held onto the subject's (user's) head by the electrode assembly; the electrode assembly may be adhesively connected to the user's head and/or neck to form an electrical contact with the desired regions on the user, and the neurostimulator may be connected e.g., adhesively and/or electrically, to the electrode assembly. As described below, the connectors between the neurostimulator and the electrode assembly may be positioned in a particular and predetermined location that allows the neurostimulator to be robustly connected to the electrode assembly and therefore the user's head/neck without disrupting the connection, and while permitting the system to be worn on a variety of different body shapes.

Electrode assemblies are generally described in detail below, along with specific examples and variations. In particular, described herein are electrode assemblies that are thin (e.g., generally less than 4 mm, less than 3 mm, less than 2 mm, less than 1 mm, etc. thick, which may not include the thickness of the connectors that may extend proud from the thin electrode assembly), and flexible, and may be flat (e.g., formed in a plane). For example, they may be printed on a flex material, such as the material used to print a flex circuit. In use, they can be wrapped around the head to contact it in at least two locations (e.g. at the temple and the back of the neck and/or behind the ear). The electrode assembly may include a connector (electrical and/or mechanical) that extends proud of the otherwise flat/planar surface to connect the active regions of the electrode assembly to the neurostimulator. For example, the neurostimulator may be mechanically and electrically connected by one or more snaps extending from the front of the electrode assembly. In some examples, one snap connects to a first active electrode region (anodic or cathodic region) that is surrounded by an adhesive to adhere the active region to the user's head. A second electrode region (anodic or cathodic) on a separate part of the electrode assembly may be electrically connected to the other connector. For example, the second electrode region may be adapted to fit either on the region over the mastoid bone, behind the subject's ear (energy electrode configuration) or a region across the user's neck at the base of the hairline, e.g., near the midline of the neck (calm electrode configuration).

The electrode apparatus may be printed (e.g., by flexographic printing, laser printing with conductive ink, silkscreening, etc.) on a flexible plastic substrate (flex substrate) and may also include a pair of connectors (snaps) on the side opposite the skin-facing electrodes. The electrode active regions on the back of the assembly may include a layer of conductor (e.g., silver), over which a layer of Ag/AgCl that is sacrificial and acts as a pH buffer. A next layer of hydrogel overlays the Ag/AgCl electrode so that it can uniformly transfer charge across the active region into the skin. A portion of the electrode assembly around the active electrode area may have an adhesive that permits good contact with a user's skin.

In use, a user may interact with a controller (e.g., a smartphone controlled by application software/firmware) that pairs with the neurostimulator (e.g. by Bluetooth). The user may operate the controller to select the operational mode, e.g., the type of cognitive effect to be induced, such as an energy mode or calm mode, and/or the device could automatically detect based on the configuration of an electrode to which the apparatus is attached. The user may select, for example, from a set of ensemble waveforms which ensemble waveform to execute. There may be separate waveforms to evoke a desired experience/effect (e.g., "calm" or "energy" ensemble waveforms). An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, i.e. current amplitude, frequency, duty cycle, charge imbalance, shorting/capacitive discharge, etc., and these parameters may change at pre-specified times as they change to new segments; a transition period may be included to switch between block properties. Once the user selects an ensemble waveform, they can start the neurostimulation and the user can control or change the perceived intensity (e.g., by dialing the perceived intensity up or down), pause, or stop the session using the phone (app). In general, the perceived intensity can be scaled by the user between 0-100% of a target perceived intensity (e.g., a target current, frequency, duty cycle, charge imbalance, and/or shorting/capacitive discharge), using a control such as one or more buttons, sliders, dials, toggles, etc., that may be present on the controller (e.g., smartphone) in communication with the neurostimulator. The controller may also allow a user to activate ("on demand") a waveform configuration that is designed to evoke a predetermined response. For example, the control device could be adapted to display one or more icons to trigger phosphenes or an intensification of the perceived cognitive effect of skin sensation intensity. In addition, the controller may be configured to allow the user to press an icon to help in applying the electrode apparatus and/or neurostimulator. For example, activating this control may cause the smartphone to activate a front-facing camera on the phone to help the user to attach the apparatus to the head. During or after a session, a user can access help screens, a profile page, social sharing interfaces (i.e. tweet your experience), feedback about a session, and analysis & history of previous use. In general, the system may also be configured to pass data to and from the controller and/or the neurostimulator and to/from a remote server via the Internet. These data may include user information, waveform data, information about the function or state of the hardware device or electrode assembly, etc.

Electrode Assemblies

Any of the electrode assemblies described herein may be referred to as cantilever electrode apparatuses (or alternatively as cantilevered electrode apparatuses, cantilever electrode assembly, or simply electrode assembly), and these cantilever electrode apparatuses may include at least two electrode regions, separated from each other along an elongate body. The cantilever electrode apparatus typically attaches to the neurostimulator device by two (or more) electrical connectors (which may be referred to herein as connectors) that are in electrical contact with the electrode regions. The electrical contacts may be positioned on the cantilever electrode apparatus adjacent to each other and in a particular manner that permits both the secure attachment to the neurostimulator and prevents disruption of the electrical contact while the cantilever electrode apparatus is worn by the subject, even while the subject moves about. For example, the spacing of the connectors may be between 0.6 and 0.9 inches apart on center (from center to center), and more preferably between about 0.7 inches and about 0.8 inches. The electrical connectors typically extend from the otherwise substantially flat surface of the cantilever electrode apparatus, and may plug into the neurostimulator. The electrical connectors may mechanically engage with the neurostimulator (e.g., they may be snaps), which may also provide mechanical support for the connection between the cantilever electrode apparatus and the neurostimulator, and thereby help support and hold the neurostimulator on the subject's body when the cantilever electrode apparatus is attached to the subject.

In general the cantilever electrode apparatuses include two or more connectors at or near one end region of the elongate body of the cantilever electrode apparatus, and two (or more) electrode regions are positioned along the elongate body of the cantilever electrode apparatus. The two or more connectors (which may also be referred to as electrical connectors) may be at one end region and help secure the entire cantilever electrode apparatus to the neurostimulator, even while a second electrode region is positioned at a distance (e.g., greater than 2 inches, greater than 3 inches, greater than 4 inches, etc.) along the elongate body of the cantilever electrode apparatus from the connectors and another electrode region.

Each electrode region of the cantilever electrode apparatuses described herein typically includes an active region on a back side of the electrode region that is adapted to contact the subject. The active region may include a hydrogel that transfers energy (e.g. current) from the neurostimulator to the subject's skin. The active region is in electrical communication with the connector.

In general, the elongate body forming the cantilever electrode apparatuses may be made of a material that is rigid in at least one direction, even while flexible in another direction. For example, the elongate body of the cantilever electrode apparatus may be formed of a relatively flat sheet of material (e.g., flex circuit material) that is relatively thin (e.g., less than 3 mm, less than 2 mm, less than 1 mm, etc.). The sheet of material may extend in a plane, and the material may not be bendable in the direction of the plane although it may be bendable out of the direction (e.g., can be curved up/down), and may twist. This partial rigidity may help support the cantilever electrode apparatus on the body while allowing it to conform to a wide variety of subject body sizes. In some variations the cantilever electrode apparatus is made of a material that is rigid, but can be bent by the application of force to hold a shape. For example, the elongate body of the cantilever electrode apparatus may be ductile, e.g., may be made (at least in part) of a shape memory material that allows bending.

The configuration of the cantilever electrode apparatuses described herein may provide numerous benefits compared to other possible arrangements, including variations in which a wire or separate connection connects a second (or more) electrode region(s) to a neurostimulator. Manufacturing electrode sets with connectors and cabling (or wires) can be time-consuming, expensive, and may be a source of variability or poor yield. The electrode apparatuses described here are more consistent, robust, and manufacturable at scale. For example, the cantilever electrode apparatuses described herein may include least a few mm of adhesive surrounding the active area of each electrode, which may help make good contact with the skin when the cantilever electrode apparatus is attached to a wearable neurostimulator. For electrode apparatuses and microstimulators that are configured to be worn on the temple (e.g., adjacent to the eye), the amount of adhesive in one portion of the electrode apparatus may be limited; in particular, the portion that will be positioned below a lower edge and/or above an upper edge of the electrode, to prevent the unit from extending too far towards the eye and/or towards the hairline at the temple. In some variations it is desirable to have the cantilever electrode apparatus and the electrical stimulator with its overlaying hardware unit positioned on the face so that it does not interfere with a temple portion of a pair of glasses that may be worn while wearing the device (e.g., the region adjacent to the ear). In addition, it may be beneficial for the bottom edge of the cantilever electrode assembly (at the first electrode portion) to correspond with the bottom edge of the electrical stimulator to help guide self-placement using the lower edge of the device to align horizontally with the edge of the eye, an easy landmark for self-placement; thus, it may be beneficial to limit the amount of adhesive below/around the lower section of the electrode.

As mentioned above, there are also numerous benefits of using a connector for electrically connecting the active regions of the cantilever electrode apparatus to the electrical stimulator both mechanically and electrically. For example, an apparatus that uses a mechanical and electrical connector, such as a snap connector or other connector that stands proud from the relatively thin cantilever electrode apparatus may prevent misadjustment of the apparatus. In particular, it may be beneficial to have two connectors (e.g., snaps) rather than just wires or one snap and a wire to connect the wearable apparatus and the cantilever electrode apparatus. The second mechanical/electrical connector such as a snap may improve the physical connection between electrode, adhesive pad, and hardware unit (neurostimulator/electrical stimulator). In addition, the hardware unit (neurostimulator/electrical stimulator) and electrode apparatus may fit under the temple portion of an eyeglass frame for users wearing glasses; thus the portion of the combined assembly (electrode assembly and neurostimulator) should ideally be thin enough to fit between glasses and the temple region. However, it may also be beneficial to have some portions of the system (e.g., the neurostimulator) be sufficiently thick to allow the apparatus to contain a sufficient battery (or other power portion) so that the unit can be used for a reasonable amount of time between charges (e.g. at least 20 minutes of electrical stimulation, at least 30 minutes of electrical stimulation, at least 40 minutes of electrical stimulation, at least 50 minutes of electrical stimulation, at least 60 minutes of electrical stimulation, at least 120 minutes of electrical stimulation, etc.). Thus one portion of the neurostimulator may be thick enough to allow a standard battery and/or circuitry at one end region (e.g., an end that is worn higher up on the face). Thus, it may be beneficial to locate the mechanical/electrical connectors such as snaps that extend proud from the cantilever electrode assembly toward the thinner end, separated from the battery compartment of the neurostimulator to reduce the overall thickness of the system in some variations, allowing the connector receptacles to be under a PCB (or in a through hole/exclusion of a PCB) rather than under a thick battery portion (or under both a battery and PCB). However, in some variations it may be beneficial to have the connector(s) be positioned under the battery portion or have one connector under the battery portion and one connector under the thinner region separated from the battery portion.

For example, in some variations it may be beneficial to have one connector on the electrode assembly (e.g., cantilever electrode assembly) near the portion of the neurostimulator hardware that is highest up on the forehead; this may help ensure that this upper portion of the device doesn't pull away from the electrode. If that happens, then the weight of the hardware unit may pull the electrode further from the head and eventually lead to poor (i.e. non-uniform, inconsistent, or high impedance) contact between the electrode active area and the skin. An adhesive may be used between the neurostimulator and the electrode assembly to prevent this; alternatively or additionally an additional mechanical connector may be used (an adhesive may be considered one type of mechanical connector, and may be present on the electrode assembly and/or on the neurostimulator body).

It may also be beneficial to have at least one of the electrical/mechanical connectors (such as a snap) at or near (and preferably behind) the active area of the first electrode portion, as this may make the electrical connection with the hardware unit easier and more robust. Another reason it may be beneficial to have at least one of the electrical/mechanical connectors (such as a snap) at or near (and preferably behind) the active area of the first electrode portion is that both the active region and connector receptacle on the stimulator device may be placed centrally within the electrode portion and dermal-facing side of the stimulator. Positioning the first active region centrally in an electrode portion (i.e. away from the edges of the electrode portion) is advantageous in some cases when adhesive is placed around the active region in order to improve the uniformity of contact with the subject's skin. Positioning a connector receptacle (e.g. for a snap) centrally in a wearable electrical stimulator is also advantageous because the receptacle requires vertical clearance and may not easily fit near the edge of the stimulator device.

As will be described in greater detail in reference to FIGS. 7A-7F, the overall shape of the neurostimulator may be triangular, and particularly the surface of the neurostimulator (though curved/concave and twisted) adapted to connect to the electrode apparatus and face the patient may be three-sided (e.g., roughly triangular). This roughly triangular shape may include rounded edges, and the thickness of the stimulator (in the direction perpendicular to the surface contacting the cantilever electrode apparatus) may vary, e.g., be thinner along one side, and particularly the side (the portion between the orbital edge and the auricular edge) that will extend laterally from the edge of the eye in the direction of the ear. This shape may also be beneficial when helping to fit/be worn on most people in a region of the face/head that tends to not have hair. Both adhesive and conductive hydrogel that may cover an active electrode region function more effectively on skin with little or no hair. This thin lower corner (the orbital/auricular corner) may fit between the eyebrow and hairline, while the wider portion is positioned up in the forehead area where there is less likely to be hair.

FIGS. 1A-1D and 2 illustrate one variation of a cantilever electrode apparatus ("electrode apparatus") that may be used with a neurostimulator to be is worn on a subject's head. In this example, the cantilever electrode apparatus 100 includes a plurality of electrode portions (two are shown) 103, 105. In FIG. 1A, a front perspective view is shown. The front side is the side that will face away from the subject when worn. The cantilever electrode apparatus is thin, so that the electrode portions include a front side (visible in FIGS. 1A and 1B) and a back side (visible in FIG. 1D). As shown in the side view of FIG. 1C, the device has a thin body that includes the electrode portions 103, 105 as well as an elongate body region 107 extending between the two electrode portions. The elongate body is also thin (having a much larger diameter and height than thickness). The thickness is shown in FIG. 1C.

In this example, two connectors 115, 117 (electrical and mechanical connectors, shown in this example as snaps) extend from the front of the cantilever electrode apparatus. The front of the first electrical portion 103 may also include an optional foam and/or adhesive material 121 through which the snaps extend proud of the first electrical portion. The first electrical portion is shaped and sized so that the snaps will connect to plugs (ports, holders, opening, female mating, etc.) on the electrical stimulator. As described above, the connectors may be separated by between about 0.6 and about 0.9 inches (e.g., between about 0.7 and about 0.8 inches, etc., shown in FIGS. 1A-1D and 2 as about 0.72 inches). The second electrode portion may also include a foam or backing portion 123. This foam/backing region may be optional. In some variations the separation between the connectors is not limited to 0.7 to 0.8, but may be larger (e.g., between 0.7 and 1.2 inches, 0.7 and 1.1 inches, 0.7 and 1.0 inches, 0.7 and 0.9 inches, etc.) or smaller (e.g., between 0.2 and 0.7, 0.3 and 0.7, 0.4 and 0.7, 0.5 and 0.7, 0.6 and 0.7 inches, etc.).

FIG. 1D shows a back view of this first example of a cantilever electrode apparatus. In this example, the first 103 and second 105 electrode portions are also shown and include active regions 133, 135. The active regions are bordered by adhesive 140. The first 103 electrode portion includes, on the back (patient-contacting) side, a first active region 133, surrounded by an adhesive material 140 that extends. The active region may include a conductive material (e.g., electrically conductive gel). Similarly, the back of the second electrode portion 105 includes the second active region 135 which is bounded, e.g., around its entire circumference, or at least on, by an adhesive 140. The adhesive may be any biocompatible adhesive that can releasably hold the material to the skin.

FIGS. 2A and 2B show exploded views of the exemplary cantilever electrode apparatus of FIGS. 1A-1D. In FIG. 2A, the front side of the cantilever electrode apparatus is shown with the foam backing 121, 123 (which may be adhesive on one or both sides) materials and snaps 117, 115 removed. The snaps may include two parts (not shown in FIG. 2A), a base and a post, and the base may be positioned on the back side of the elongate body forming the substrate (or base) 108 for the cantilever electrode apparatus. The base may be a flex circuit material, e.g., that is relatively insulating, flexible out of the plane of the material, but rigid in the plane (meaning it can be bent up/down out of the plane, but has rigidity when pushed/pulled in the direction of the plane of the material). The flex circuit may have a dielectric layer covering all or part of the front and/or back side, covering and insulating conductive traces. Many of the structures used to form the electrode regions and connectors may be printed directly onto the base or attached to the base (e.g. by flexographic printing, silk screening, or laser printing with conductive ink). For example, in FIG. 2B, the back (patient-facing) side of the base of the cantilever electrode apparatus is shown with the snaps attached so that the base of the snaps extends along the back side and can be in electrical contact in one case with the electrically conductive first active region forming part of the first electrode portion. The second snap is offset from the first electrically active region and may contact a conductive trace (e.g., printed on the body 108 of the base) and extending along the elongate body region 107 until it contacts the second active region. In this manner, the first and second connectors may establish electrical communication between the active regions and the neurostimulator. In FIG. 2B the active regions includes a conductive gel (although additional materials, including sacrificial materials, pH buffer materials, antibacterial/germicidal materials, analgesic, itch-reducing, etc.). The adhesive portion 140 is also shown in this exploded view.

As described above, the foam material over either or both of the front sides of the first and second electrode portions may be omitted. FIG. 3 shows an example in which the foam material, which may also or alternatively be an adhesive to help secure the cantilever electrode apparatus to the neurostimulator is not included in the cantilever electrode apparatus. In this example, the connectors (snaps 117, 115) alone may be used to secure the cantilever electrode apparatus to the neurostimulator.

Figure 6:
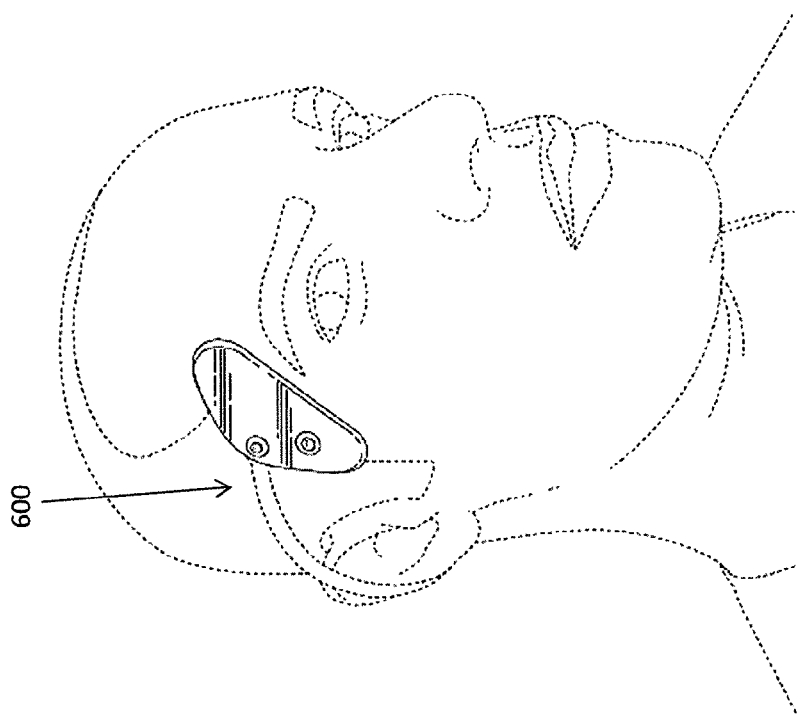
FIG. 6 illustrates a cantilever electrode apparatus (similar to those shown in FIGS. 1A and 4A) worn on a subject's head.

The cantilever electrode apparatus show in FIGS. 1A-3 may be particularly useful, for example, to connect a neurostimulator to a subject's head (as illustrated in FIG. 6, below). The neurostimulator is attached to the front side of the cantilever electrode apparatus by snapping onto the proud connectors, while the elongate body region 107 is bent to extend behind the subject's head and down to a portion on the midline of the back of the patient's neck. Both the first electrode portion and the second electrode portion may be adhesively held with the electrically active regions against the skin, allowing the neurostimulator to apply energy, and in particular the waveforms as described in application Ser. No. 14/320, 443, titled "TRANSDERMAL ELECTRICAL STIMULATION METHODS FOR MODIFYING OR INDUCING COGNITIVE STATE," filed on Jun. 30, 2014, Publication No. US-2015-0005840-A1 and herein incorporated by reference in its entirety.

Another example of a cantilever electrode apparatus similar to the variation shown in FIGS. 1A-3 is shown in FIGS. 13A-13D. In this example, the cantilever electrode apparatus 1300 includes two electrode portions 1303, 1305 each having at least one active region 1333, 1335. FIG. 1A shows a front perspective view, FIG. 1B is a front view, FIG. 1C is a side view and FIG. 1D is a back view. The front side is the side that will face away from the subject when worn. Electrode portions 1303, 1305 are connected by an elongate body region 1307 extending between the two electrode portions. The elongate body is also thin (having a much larger diameter and height than thickness). The thickness is apparent in FIG. 13C). None of the figures herein are to scale, unless indicated otherwise. The width of the connection region between two electrode regions in any of the variations described herein may be relatively small (though wider than the thickness of the electrode apparatus body region), e.g., between about 0.5 mm and 20 mm, between about 1 mm and 15 mm, between about 2 mm and 15 mm, between about 3 mm and 10 mm, etc.

In this example, two connectors 1315, 1317 (snaps that act as both electrical and mechanical connectors) extend proud from the front of the cantilever electrode apparatus a few mm (e.g., between 1-5 mm). This variation does not illustrate any foam or adhesive on the front side (e.g., over the first and/or second electrical portions, as shown in FIGS. 1A-3), however such may be included. As described above, the connectors may be separated by between about 0.6 and about 0.9 inches (e.g., between about 0.7 and about 0.8 inches, etc., shown in FIG. 13A-13D as about 0.72 inches). FIG. 13D shows a back view in which the first 1303 and second 1305 electrode portions are also shown and include active regions 1333, 1335. The active regions are bordered by adhesive 1340. The first 1303 electrode portion includes, on the back (patient-contacting) side, a first active region 1333, surrounded by an adhesive material 1340 that surrounds the entire circumference of the active region. Adhesive regions that surround all or most of the circumference of an active region are beneficial in curved and/or hairy (e.g. with vellus hair) body regions to ensure as uniform electrical contact as possible between the active region and the subject's skin. The active region may include a conductive material (e.g., electrically conductive hydrogel). Similarly, the back of the second electrode portion 1305 includes the second active region 1335 which is bounded on an upper and lower side by an adhesive 1340. The adhesive may be any biocompatible adhesive that can releasably hold the material to the skin. Although the connectors shown in these exemplary cantilever electrode apparatuses are snaps, other types of connectors may include clamps, screws, clasps, clips, or the like.

Figures 22E, 22F:
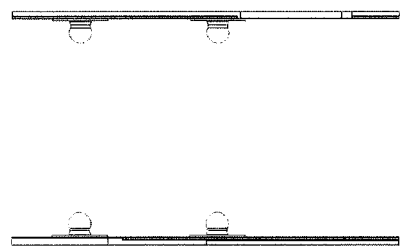
FIGS. 22A-22F illustrate another variation of a cantilevered electrode assembly similar to the one shown in FIGS. 1A-1D and 2A-3, in which the two electrode skin-contacting portions (connected by the flexible elongate body region) are oriented differently, providing a more compact profile; the active regions of the electrode skin-contacting portions extend from edge-to-edge of a central region of both electrode skin-contacting portions.
Figure 22A:
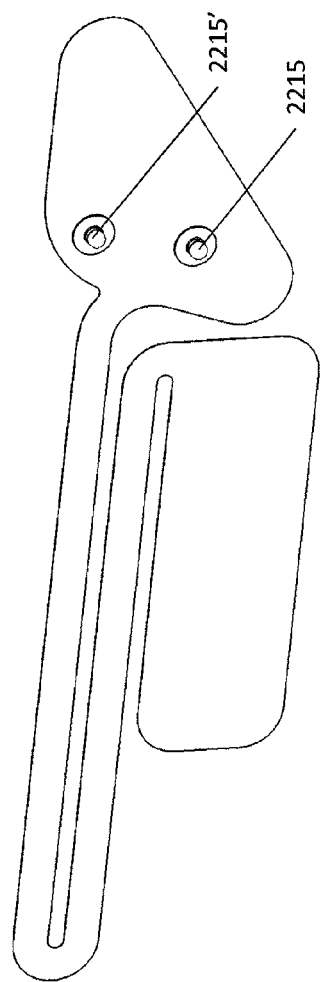
Figure 22B:
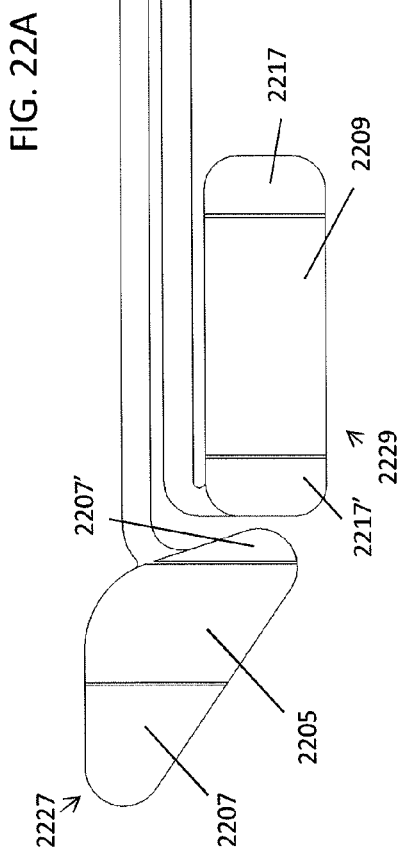
Figures 22C, 22D:

FIGS. 22A-22F illustrate another variation of a cantilever electrode apparatus (or cantilever electrode assembly) similar to the one shown in FIGS. 1A-1D and FIG. 13A-13D. In this example, the front of the apparatus includes the pair of connectors 2215, 2215' (shown as snaps) similar or identical to those described in FIGS. 1A-3 and 13A-13D, spaced between about 0.7 and 0.8 inches. In this example, the second electrode region (which may be positioned on the wearer's neck, for instance) is oriented horizontally, in the direction of the elongate connecting member. This may allow the entire assembly to be more compact for packaging and manufacture. FIG. 22B shows a back view of the apparatus, including the electrically active regions 2205, 2209 which may include a conductive hydrogel. In this example, the electrically active regions 2205, 2209 may extend from the edge-to-edge of the two skin-contacting electrode regions 2227, 2229. For example, the first conductive layer and/or the sacrficical layer (and any intervening layer) may comprise a portion of the area underlying the conductive hydrogel (e.g. 2205) so that the active electrode region is targeted and sized correctly while still permitting a strip of hydrogel 2205 to cover the electrode region from one end to another for improved manufacturability. This configuration may simplify the construction of the apparatus (as it may be formed without having to pick and place the hydrogel "islands" as shown in FIGS. 1A-1D). These conductive regions are bracketed on either side by adhesive 2207, 2207' and 2217, 2217'. For example, during manufacture, parallel lanes of adhesive and hydrogel may be placed on the flex circuit without requiring a pick and place or additional die-cut step for placing a hydrogel island surrounded by an adhesive region. In the example electrode apparatus shown in FIG. 22B, manufacturing may use three lanes of adhesive with appropriate width parallel to the adjoining strips or lanes of adhesive and hydrogel on the two electrode regions 2227,2229. For example, a first lane of adhesive having width appropriate for adhesive region 2207, a second lane of adhesive having width appropriate for the combined area of adhesive regions 2207' and 2217', and a third lane of adhesive having width appropriate for adhesive region 2217. (In another example, separate lanes of adhesive may be used for adhesive regions 2207' and 2217'.) Also during manufacture, two lanes of hydrogel of appropriate width to cover hydrogel regions 2205 and 2229 of the electrode apparatus. In some examples, a first manufacturing step places the strips of adhesive and hydrogel onto a disposable, temporary substrate so that the combined parallel strips of adhesive and hydrogel may be die cut to have the shape appropriate for the electrode regions 2227 and 2229 (including separating adhesive regions 2207' and 2217' from a single lane of material into two distinct adhesive regions for the two electrode regions), then the die cut hydrogel-adhesive regions are transferred from the temporary, disposable substrate to the electrode apparatus at the appropriate location. A beneficial feature of this design is that the electrode apparatus (and components in its manufacture) do not need to be turned, rotated, or placed and can be more readily manufactured in an efficient roll-to-roll framework. FIGS. 22C and 22D show top and bottom views, respectively, of the thin cantilevered electrode apparatus of FIG. 22A, and FIGS. 22E and 22F show right and left side views.

FIGS. 4A-4D illustrate another example of a cantilever electrode apparatus. This example is very similar to the variation shown in FIGS. 1A-2B. The connectors (snaps 417, 415) are in the same position as shown in FIGS. 1A-1D, as are the shape of the first electrode portion 403 and foam/backing material 421 (which may also or alternatively be an adhesive material). An advantage of having multiple electrode apparatuses with the same shape is that they can be used interchangeably with a single neurostimulator device. However, the example shown in FIGS. 4A-4D includes a different overall shape, and may be used to connect, for example, to different regions of the patient's head/neck. In particular, the portion of the substrate forming the elongate body region 407 extending between the two electrode portions 403, 405 is shaped slightly differently. In this example, the cantilever electrode apparatus may be configured to connect, for example, to the subject's temple with the first electrode portion (to which the neurostimulator may be connected) and the elongate body region may be bent around the subject's head so that the second electrode portion may be in electrical contact with a region behind the subject's ear (e.g., at or near the mastoid). By placing the first active region 433 of the first electrode portion 405 in electrical contact with the skin at the temple region and using the adhesive material 440 surrounding the electrically active region 433 to hold the electrically active region (and the attached neurostimulator) securely in position on the subject's skin, the second electrically active region may also be adhesively 441 held to skin so that the second electrically active region 435 is in contact with the mastoid region.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 1A-3 and FIGS. 4A-5. The bend or curve, in which the elongate body may even double back on itself, may allow the material to flex or bend to allow it to be adjustably positioned over and/or around the subject's head, as shown in FIGS. 6 and 8A, for example.

Figure 5A:
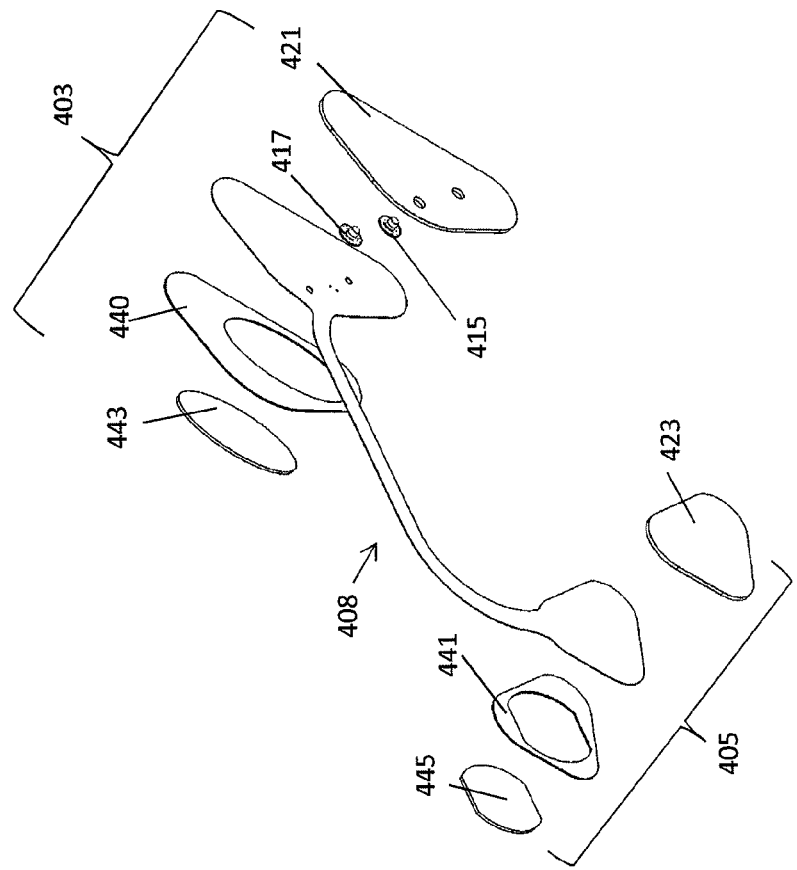
FIG. 5A is an exploded view of the cantilever electrode apparatus of FIG. 4A.

FIG. 5A shows an exploded view of the cantilever electrode apparatus of FIGS. 4A-4D. In this example, the substrate (elongate body 408) forms the elongate body region between the first electrode portion 403 (formed of the first electrically active region having conductive material (not visible in FIG. 5A), hydrogel overlying the electrically active region 443, adhesive 440 and optional backing material 421, as well as a portion of the substrate 408) and the second electrode portion 405 (formed of the second electrically active region (not visible), hydrogel overlying the electrically active region 445, adhesive 441 and optional backing material 423, as well as a portion of the substrate 408). One or more electrical traces may also be included, e.g., directly printed (or silk-screened, etc.) onto the substrate 408, connecting the second electrically conductive region to the second connector 417.

As mentioned above, the connectors (pins 415, 417) are spaced a predetermined distance apart (e.g., between about 0.7 and 0.8 inches) with the first pin 415 behind, and in direct electrical contact with the first electrically conductive region 433 of the first electrode portion 403. The second connector (pin 417) is electrically insulated from the first connector and the first electrically conductive material, and may be positioned so that it is not directly behind the first electrically active region 433, but it is still in the first electrode portion 403, and extends proud of the back of the first electrode portion (e.g., the back of the substrate forming the first electrode portion).

FIGS. 14A-14D shows another example of a cantilever electrode apparatus similar to the variation shown in FIGS. 4A-5. In FIGS. 14A-14D, the cantilever electrode apparatus includes mechanical/electrical connectors (snaps 1417, 1415) in approximately the same positions as shown in FIGS. 1A-1D and 4A-4D. The electrode apparatus includes a first electrode portion 1403 and a second electrode portion 1405. FIGS. 14A and 14B show front perspective and front views, respectively. In this example, the front side does not include any foam/backing material or additional adhesive material around either electrode portions, although such may be included. As in FIGS. 4A-4D the overall shape of the electrode apparatus may be adapted to connect to a subject's temple with the first electrode portion 1403 (to which the neurostimulator may be connected), the elongate body region may be bent around the subject's head, and the second electrode portion 1405 may be in electrical contact with a region behind the subject's ear (e.g., at or near the mastoid). By placing the first active region 1433 of the first electrode portion 1405 in electrical contact with the skin at the temple region and using the adhesive material 1440 surrounding the electrically active region 1433 to hold the electrically active region (and the attached neurostimulator) in position, the second electrically active region may also be adhesively 1441 held to skin so that the second electrically active region 1435 is in contact with the mastoid region.

FIGS. 23A-23F also illustrate another example of a cantilevered electrode array, similar to those described above in FIGS. 4A-5 and 14A-14D. In FIG. 23A, the electrode assembly includes a pair of connectors (shown as snaps) 2315, 2315' that are in approximately the same position as those described above, and are configured to mate with and secure to a wearable electrical stimulation device (e.g., neurostimulator). As described above, the cantilever electrode apparatus/assembly includes a pair of skin-contacting electrode regions 2327, 2329. The first electrode region 2327 includes the snaps on the front side (the side that will not contact a subject when the apparatus is worn), which will connect to the wearable electrical stimulator and both hold the stimulator on the head and make an electrical connection to each of the active regions on the first and second skin-contacting electrode regions 2327, 2329. The second skin-contacting electrode region 2329 will be cantilevered away from the first skin-contacting electrode region 2327 and the electrical stimulator (when attached), but will also be held against the subject's skin, for example, behind the ear.

FIG. 23B shows the back of the cantilevered electrode apparatus, which is configured to face (and contact) the subject wearing the apparatus. In this example, the both skin-contacting electrode regions include active regions that extend from at least one edge of the apparatus across the skin-contacting electrode region to form the active zones on the skin-contacting electrode regions. For example, in FIG. 23B, the first skin-contacting electrode region 2327 has an active region 2205 that forms a central strip across the skin-contacting electrode region 2327. In other examples, the hydrogel 2205, 2209 may extend from one edge of the electrode region to another edge of the electrode region, while the underlying electrode active area only covers a subset of this region in order to ensure the electrode is appropriately sized and located in order to be positioned effectively for inducing a cognitive effect. As described in more detail in reference to FIGS. 20A-20F, below, this active region is in electrical communication with one of the connectors (e.g., snap 2315), and may include a layered structure of conductive metal, sacrificial conductive layer, and hydrogel to spread the current across the entire active region; in some variations one or more additional layers may be included, such as a less-conductive (than the conductive metal and sacrificial layer) layer, e.g., comprised of carbon, between the conductive metal and sacrificial layer, that may help spread out the current across the surface of the active region before it passes into the sacrificial layer and therefore allow higher current intensities to be delivered more uniformly across the electrode-dermal contact area and thus reduce discomfort in the user. The second skin-contacting electrode region 2229 is similarly constructed, but electrically connected to the other connector (e.g., snap 2315') by a conductive trace on or in the portion of the flexible substrate 2307 extending between the two skin-contacting electrode regions.

For example, the cantilevered electrode apparatus shown in FIGS. 23A-23F may be formed of a substrate such as a Kapton (e.g., a polyimide film) and/or vinyl (e.g., coated vinyl, polyvinyl chloride or related polymer) onto which the different regions are formed by layering or attaching. The active region may include a hydrogel (e.g., AG602 Hydrogel, having a resistance of approximately 350 Ohm-cm), and Ag coating (e.g., Ag ink), Ag/AgCl coating (e.g., Ag/AgCl ink), and (optionally) a carbon conductor (e.g., Exopack Z-flo carbon filled Vinyl having a resistance of approximately <90 Ohms/cm$^2$). The connector may be a fastener including a male snap stud (e.g., Rome Fastener 76 Male Snap Stud having a resistance of <1 Ohm/cm$^2$) and an eyelet (e.g., select Engineering Carbon Filled ABS eyelet).

In another variation, a cantilevered electrode apparatus such as the one shown in FIGS. 23A-23F (or FIGS. 22A-22F) may include a substrate (e.g., Kapton or other polymeric material) and may include the active region with a hydrogel (e.g., AG602 Hydrogel, at 350 Ohm-cm), a silver/silver chloride sacrificial layer (e.g., ECM Ag/AgCl ink (85/15) with <0.2 Ohm/cm$^2$), the optional carbon layer (e.g., DuPont Carbon 5000 ink, <50 Ohm/cm$^2$), and silver layer (e.g., EMC Silver ink with <0.2 Ohm/cm$^2$). The connector may include an eyelet (e.g., Rome 76 SF eyelet with Vinyl Cover) and a stud (e.g., Rome 76 Male Snap Stud, at 1 Ohm/cm$^2$).

In any of the examples described above, the mechanical and/or electrical connectors may be positioned at or near one side (off-centered relative to) the first electrode portion. Thus, the neurostimulator, which connects at its back to the mechanical connectors on the electrode apparatus, may be connected at one side, which may allow the other end or regions of the neurostimulator to float relative to the rest of the first electrode portion of the electrode apparatus (i.e. the neurostimulator does not conform as tightly to the curvature of the body as the first electrode portion of the electrode apparatus), although pinned or held at one or more (e.g., two) points on one side or region of the electrode portion. This may allow the flexible electrode apparatus to be adhered securely to a variety of head shapes, while allowing the more rigid neurostimulator to attach with reduced risk of dislodging all or part of the first electrode portion from the wearer's head (which would cause reduced uniformity of current density on the user's skin and more discomfort), even if the wearer moves his head, including changing facial expressions, closing her eyes, squinting, etc.

As mentioned above, the elongate body region of the electrode apparatus that connects the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc., between 2 and 12 inches, between 2 and 10 inches, between 3 and 9 inches, etc.). In the plane of the electrode apparatus, the elongate body region may travel in a bent or curved path, as illustrated in the variations of FIGS. 1A-3, FIGS. 4A-5, FIGS. 13A-13D and FIGS. 14A-14D, helping to allow the material to flex or bend to be adjustably positioned over and/or around the subject's head, as shown in FIGS. 6 and 8A.

Returning now to FIG. 5B, FIG. 5B shows another example of a cantilever electrode assembly configured similar to the variation shown in FIG. 4A, in an exploded view. The cantilever electrode apparatus is configured so that a first electrode (active region) may be placed on or near a user's right temple and a second electrode (active region) may be placed on the user's right mastoid. In this example, the apparatus includes an optional backing material 421 configured to sit between the cantilever electrode assembly and an electrical stimulator device (e.g., neurostimulator). Two through holes permit a pair of conductive snap electrodes 505, 506 to fit through the backing layer 421 (i.e. foam) so that the snaps can fit into conductive receptacles of the stimulator device. There are two snaps 506 shown in FIG. 5B (a pair of conductive snaps), each of which connects a current source of a stimulator unit to a dermal electrode. However, in some variations, more than two snaps, or a single snap (e.g., having two or more electrical paths) may be used. The conductive snaps 506 may be held in place on the flexible electrode assembly by eyelets 505. The snaps and eyelets in this example are riveted via through-holes in the substrate within the region forming the first electrode region 502 (including the first electrode active region). In this example, a second electrode active region (second electrode region) 510 is located at the distal end region of the flexible electrode assembly where a second electrode active area is positioned.

Figure 5B:
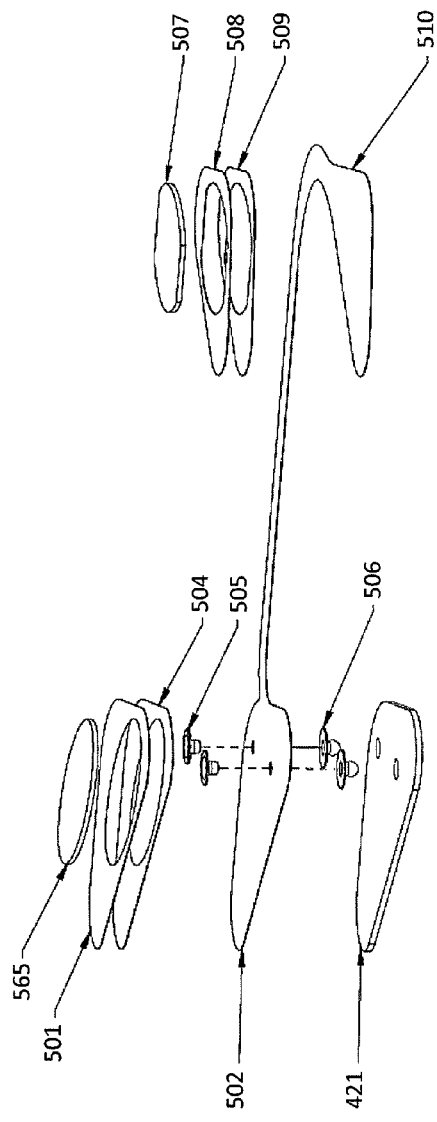
FIG. 5B is another variation of a cantilever electrode apparatus similar to the variation shown in FIG. 4A, shown in an exploded bottom perspective view.
Figure 5C:
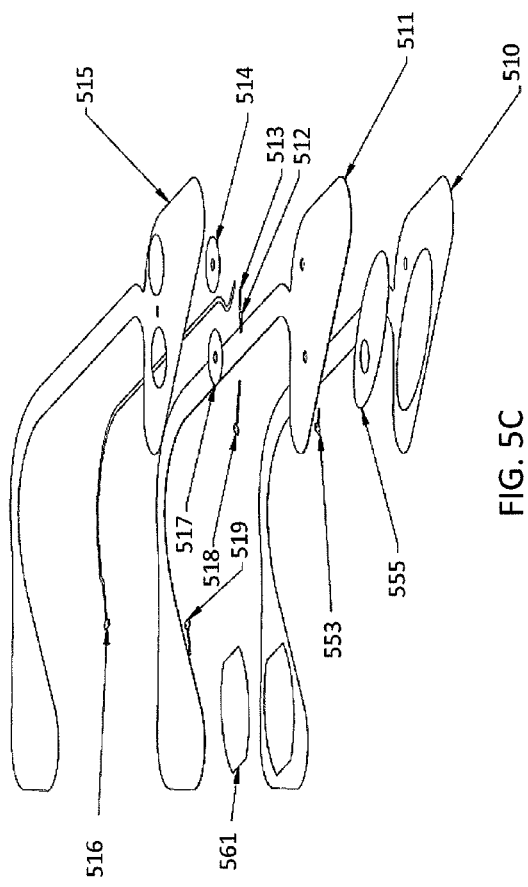
FIG. 5C is another variation of a cantilever electrode apparatus, shown in an exploded view.
Figure 7E:
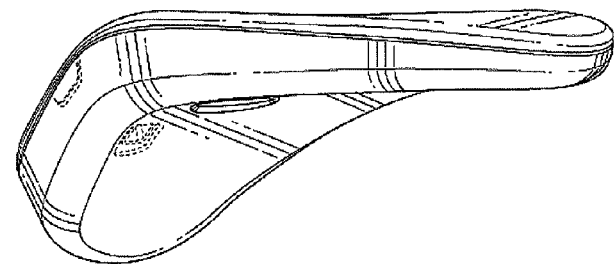
FIGS. 7A-7F illustrate front, back, left side, right side, top and bottom perspective views, respectively of a variation of a neurostimulation device (electrical stimulator) that may be used with any of the cantilever electrode apparatuses described herein.
Figure 7D:
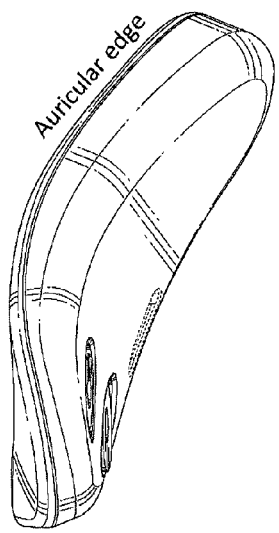
Figure 7C:
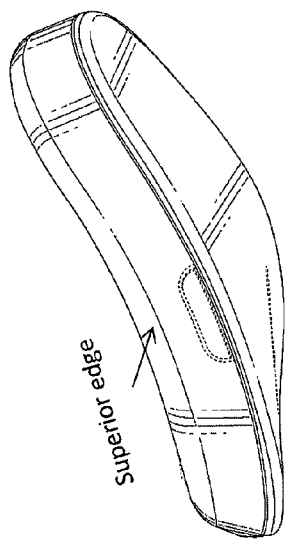
Figure 7F:
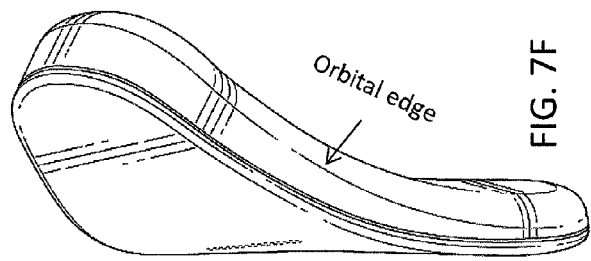
Figure 7A:
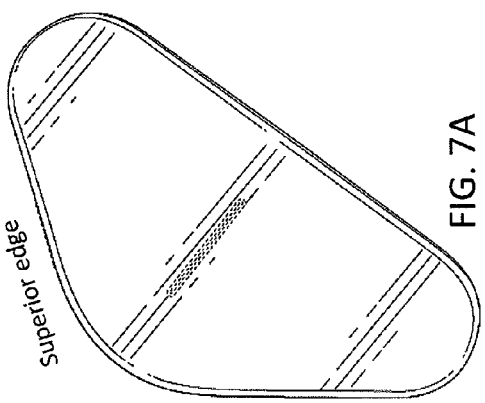
Figure 7B:
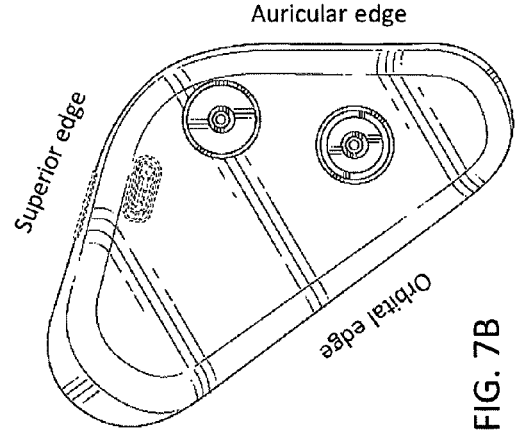

FIG. 5C shows another example of a cantilever electrode apparatus in an exploded view. FIGS. 5D and 5E show front and back views, respectively, of this variation of a flexible cantilever electrode assembly.

In FIG. 5B, the apparatus includes an oval hydrogel portion 565 that is positioned overlying the first active electrode region; the active electrode region may be formed onto the substrate (e.g., by printing, such as silk screening, photolithography, flexographic printing, or otherwise adhering it to the flexible substrate), including the conductive layer (i.e. traces and areas) and any insulating material layers. A second hydrogel region 507 may be positioned over a second active electrode region (e.g., which may include one or more conductive and, in some variations, insulating layers). A dermal adhesive region 501 may surround the first active electrode area and may help the flexible array to adhere to a subject's skin, providing adhesion around the electrode active area so that the hydrogel may make uniform and firm contact with a subject's skin. The hydrogel may also be adhesive.

In some variations, a spacer 504 may be included that has the same or similar shape as the dermal adhesive 501 and adds further depth (thickness) so that the face of the adhesive region is approximately the same distance from flexible substrate 502 as hydrogel region 565. In the variation shown, the hydrogel stands slightly proud from the surrounding adhesive region, although in other variations the hydrogel may be flush with the surrounding adhesive. In variations in which the hydrogel region extends proud, the hydrogel may slightly compress when the electrode assembly is adhered to the skin, improving the uniformity and firmness of the contact between hydrogel and skin. Similarly, in the second electrode active region at the other end region of the cantilever electrode, a second spacer 509 and dermal adhesive 508 may similarly surround the second electrode area that includes the second hydrogel 507.

FIG. 5C shows an exploded view of the flexible electrode assembly components for transdermal electrical stimulation configured similar to the variation shown in FIG. 4A. The apparatus is configured with a shape so that a first electrode active region may be placed on or near a subject's right temple and a second electrode active region may be placed on a subject's right mastoid region.

In some variations, the apparatus may be formed of multiple substrate layers. For example in FIG. 5C, the electrode apparatuses includes a skin-facing dielectric 510 layer that is an insulative layer. An additional dielectric layer 515 may be positioned to face outwards (distal from the skin and the skin-facing layer) and may have cut-out regions (exclusions) so that two snap connectors can pass through the layer. The layer may also include one or more small rectangular exclusions so that a capacitor soldered onto the internal flexible electrode substrate 511 has sufficient clearance. The top 515 (outward facing) and bottom 510 (skin facing) layers may be coatings or may be formed of solid materials that are adhesively attached to the inner substrate material 511.

In this example, an oval region 555 is a printed (silk screened, etc.) region that is formed or attached to the flexible substrate 511, and may be formed of a conductor and/or sacrificial layer (e.g., Ag/AgCl layer as described in more detail below), forming the first electrode active region. In this example, the Ag/AgCl region has a round exclusion area so that the eyelet portion of a snap electrode does not directly contact the active electrode area. Direct contact between a snap and the electrode may cause oxidation of the electrode area or create a galvanic cell due to the chemistry of the included components.

In an alternative embodiment (not shown; ideally with other, nonreactive components), the eyelet of an overlying conductive snap can be riveted through the active electrode so that the top of the eyelet is conductive with the electrode area.

FIGS. 5C-5E also illustrate various conductive traces which may be present on any of the variations described herein, to connect the electrically active regions to the electrical/mechanical connectors, such as the second electrode active region. For example, a conductive trace 553 may be formed on the skin-facing side of the flexible electrode apparatus and may conduct current through a conductive via passing from the second (outward-facing) side of the apparatus to the electrode area. A conductive, non-consumed (i.e. metal) layer (e.g. Ag, Cu, Au, conductive carbon, etc.) may also be included (not shown in FIG. 5C) as one layer forming the first and/or second electrically active regions. This conductive, non-consumed layer may be is printed as a contiguous region from trace 553 and has a similar shape as the Ag/AgCl layer 555 ("sacrificial layer"), which extends slightly beyond the underlying conductive region at all boundaries (including the interior boundary of the circular exclusion, if present) in order to ensure there are no shorts between the conductive layer printed on the flexible substrate and the overlying hydrogel. Such a short may cause current to bypass the pH buffering Ag/AgCl layer and reduce the comfort and efficacy of transdermal electrical stimulation.

Similarly, for a second electrically active region (which may be configured to position over the mastoid, as shown in FIG. 5C), a conductive trace 519 may be functionally similar to the conductive trace 553 in the first electrically active region and may be positioned and shaped to be co-incident with the Ag/AgCl layer 561 or with a conductive non-consumed layer that is in contact (and surrounded on all peripheral sides by) the Ag/AgCl layer.

In this example, flexible substrate 511 (e.g. formed of a material such as polyethylene) may form the base onto which the electrodes and any circuit elements are printed and/or attached, glued, adhered, silk-screened, etc. The substrate 511 may contain through holes for two or more conductive snap connectors; the snap connectors are not shown in FIG. 5C, but may resemble those described above in FIG. 5B.

In this example, two or more conductive carbon circular regions 514 and 517 may be coupled between the snaps and the conductive traces. Traces 512 and 513 in this example are connected by a capacitor (as described in greater detail below) that may be used as part of a capacitive element for electrode assembly identification. A capacitor is not shown in FIG. 5C, but would connect between, for example, the first and second active region, e.g., between the two electrical connectors (e.g., snaps) by traces 512, 513. Trace 518 may carry current to conductive vias (not shown) to trace 553 on the skin-facing side of the electrode assembly that is contiguous with the first electrode region (e.g., the conductive non-consumed layer, if included).

Similarly, trace 516 may carry current through a conductive via to trace 519 on the skin-facing side of the flexible electrode assembly that is contiguous with the second electrode active region (e.g., a conductive non-consumed layer, if included).

FIGS. 5D and 5E show front (away-facing) and back (skin-facing) views, respectively, of a flexible electrode assembly such as the one shown in FIG. 5C. In the plane of the electrode apparatus, the first electrode active region is at a proximal 520 end, and the second electrode apparatus is at a distal end region 530.

In any of the variations described herein, a conductive layer such as conductive carbon or another conductive material (e.g., annulus 523) may connect to a conductive snap (not shown) that fits a receptacle in an electrical stimulator unit, as well as traces that transmit current to a first electrode 534. One of the conductive carbon annuluses 521 may connect to a conductive snap that fits a receptacle in an electrical stimulator unit, as well as one or more traces that transmit current to the second electrode active region 536.

In this example, a conductive trace 524 on the front (facing away from the subject's skin) side of the apparatus transmits current from the conductive connector (e.g., from the conductive carbon layer) through a conductive via (not shown) to trace 533 on the skin-facing (back) side and then to the first electrode active region 534, which may be formed of the conductive layer(s) (e.g., non-consumed conducting layer and overlaid consumed conductive layer, and hydrogel layer). At least a portion of the conductive layer in this example includes an exclusion area (of the active electrode region) 532 and through hole 535 where the electrical (and mechanical) connector, a snap in this example (not shown) may pass. A second through hole 531 in the substrate may provide clearance for a second electrical connector (e.g., conductive snap) to be riveted through the flexible substrate. In FIG. 5D the traces 522 and 526 may act to short the two electrode paths through a capacitive element (e.g., capacitor, not shown) which may be used to identify the type and veracity of an electrode assembly as described in detail below.

FIG. 6 illustrates a variation of a cantilever electrode apparatus 600 worn on a subject's head. As illustrated, the apparatus is positioned with the first electrode portion adhesively attached at the temple region and a second electrode portion attached to a region behind the head (e.g., behind the ear or neck region, not shown).

A neurostimulator (not shown in FIG. 6) may be attached to the cantilever electrode apparatus either before or after it is applied to the subject. FIGS. 7A-7F illustrate perspective views of one variation of a neurostimulation apparatus, and FIG. 8A shows the apparatus applied to a subject's head with a cantilever electrode apparatus. FIG. 8B shows a back view of the neurostimulator (electrical applicator) of FIGS. 7A-8A.

In FIGS. 7A-7F the various edges are labeled, based on where the apparatus will be worn by the subject, similar to what is illustrated in FIG. 8A. In general, the side of the unit worn toward the ear is the auricular edge, the side worn highest on the forehead is the superior edge, and the side worn nearest the eye/eyebrow is the orbital edge. The overall shape of the neurostimulator is triangular (including rounded edges). As used herein triangular includes shapes having rounded/smooth transitions between the three sides, as illustrated. The subject-facing surface is specifically contoured to fit in the predefined orientation, making it difficult or impossible for a subject to misapply, and risk placing the active region of the attached cantilever electrode apparatus in the wrong place. When attaching the cantilever electrode apparatus to the neurostimulator, the cantilever electrode apparatus may flex or bend so that it is contoured to match the curved and twisted surface. This surface is a section of a saddle shape, in which there is an axis of curvature around which the surface is concavely curved, and an axis of twisting, which may distort the curved surface (the two axes may be different or the same).

As shown in FIG. 8B, the bottom surface of the neurostimulator, to which the cantilever electrode apparatus attaches, including mating junctions (openings, receptacles, female receivers, etc.) to receive and make electrical and mechanical contact with the connectors on the cantilever electrode apparatus. These receivers may also be positioned to optimize the placement of the cantilever electrode apparatus, allowing it to make sufficient contact with the neurostimulator and subject, and prevent the cantilever electrode apparatus from bending or breaking contact, even while the subject is mobile and/or active.

Although the variations described above for the cantilever electrode apparatus illustrate a flexible structure, in which a substrate (e.g., flex circuit) material is thin and permitted to bend in at least one axis, in some variations the cantilever electrode apparatus may be rigid. FIGS. 9A-9C and 10A-10C illustrate two variations of rigid, or semi-rigid cantilever electrode apparatuses.

Figure 9A:
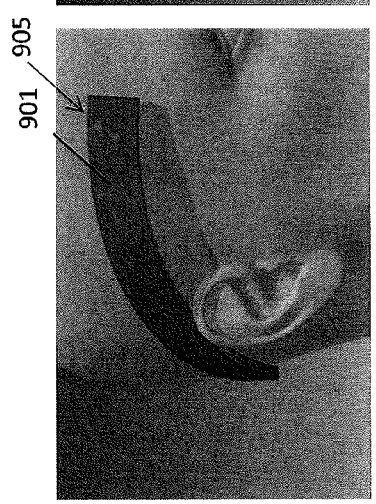
FIGS. 9A-9C show three views illustrating another variation of a cantilever electrode apparatus having a rigid body.
Figure 9B:
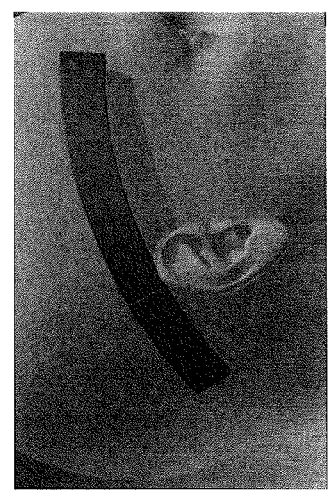
Figure 9C:
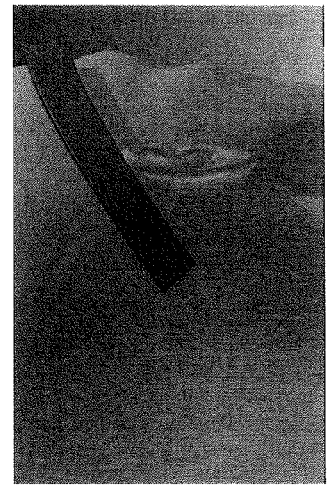

In FIGS. 9A-9C, the device is shown as a CAD rendering of an exemplar neurostimulator 903 attached to a cantilever electrode apparatus that may be bendable (ductile) or hinged to achieve a wearable form factor allowing contact with different regions of the head/neck. A neurostimulator (not shown) may include all or a subset of electronic components and may be attached to the projecting pins 905. For example, an anode electrode (the electrically active region of the first electrode portion) may be positioned on the right temple area and electrically conductive when the posterior portion (e.g., the second electrode region) of the cantilever electrode apparatus may be positioned so that a cathode electrode targeting the right mastoid behind the ear is positioned correctly (electrode active region not shown).

Figure 10A:
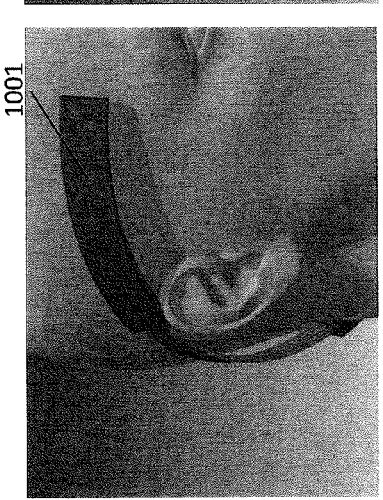
FIGS. 10A-10C show three views illustrating another variation of a cantilever electrode apparatus.
Figure 10B:
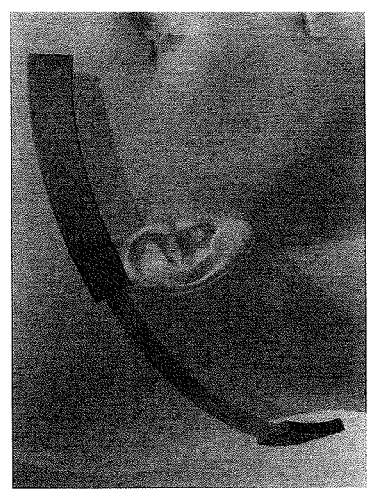
Figure 10C:

Similarly, the example shown in FIGS. 10A-10C illustrates a region having a rigid elongate body (including connector region of the elongate body), the elongate body extends further and may allow contact with the second active region on the back of the subject's neck. All or a portion of the body may be ductile so that it can be bent into a shape allowing it to conform to the neck. In some variations the elongate body may be hinged to allow it to bend/flex during use.

Figures 11A, 11B:
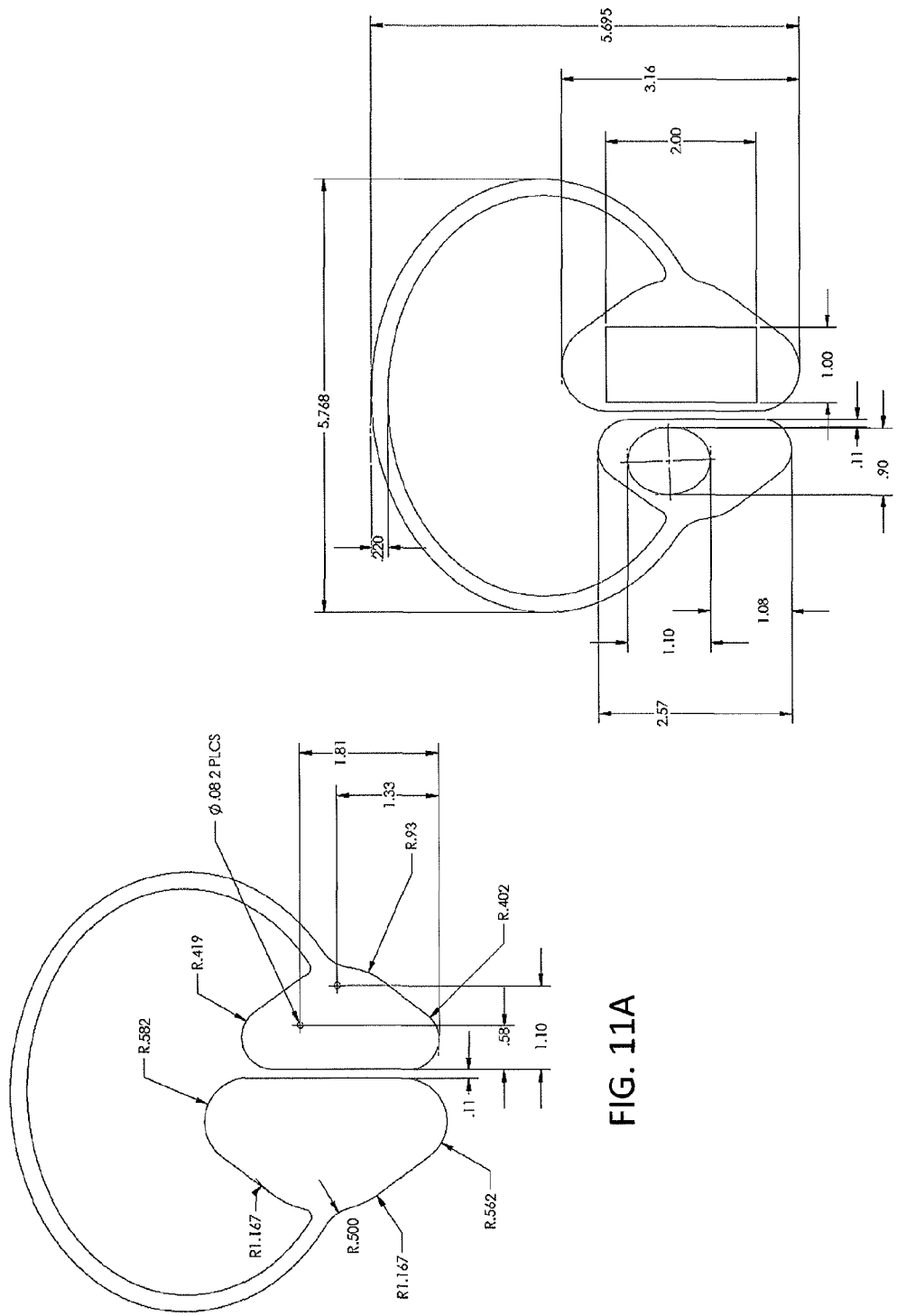
FIGS. 11A-11B show front and back views, respectively, of another variation of a cantilever electrode apparatus.

FIGS. 11A and 11B illustrate another variation of a flexible (at least in one axis of freedom) cantilever electrode apparatus which may also be formed of a flex circuit material. FIG. 11A shows a front view and FIG. 11B shows a back view of the substrate portion onto which the other elements may be attached (e.g., the active regions, the connectors, adhesive, etc.). In this example, the device includes an elongate thin connector portion of the substrate body, similar to the variations shown in FIGS. 1A-3 and 4A-5, above. Exemplary dimension (in length units of inches) are shown for illustrative purposes only, and may be varied.

Figure 12:
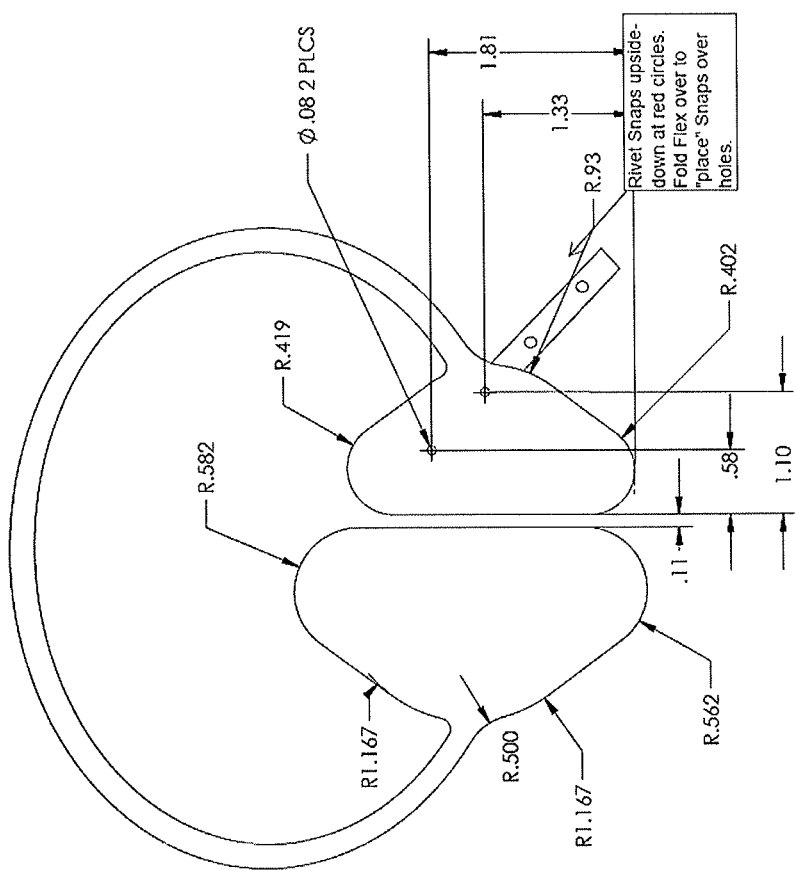
FIG. 12 is a front view of another variation of a cantilever electrode apparatus.

FIG. 12 is another variation of a cantilever electrode apparatus in which the connectors are coupled to a different portion of the substrate in an upside-down configuration, connected by conductive traces (not shown), and folded back over so that they may be positioned over the first electrode region but without requiring the connector be riveted through the flexible substrate into the active region, similar to what is illustrated in FIGS. 1A-3, and 4A-5 above. Also, this may allow a better fit for larger electrodes while reducing the constraint of where a connector for the active region is located. As will be illustrated and described in greater detail below, in general the connectors may be configured so that they engage with the neurostimulator on the top surface, and electrically connect to the active region(s) of the electrode apparatus on the opposite, e.g., bottom, surface. Thus, in some variations a snap may pass through the flat, and flexible substrate (e.g., flex circuit) material and make electrical contact with the electrically conductive material of the active region. To avoid concentrating delivered current too focally, the apparatus may be configured so that a portion (e.g., the bottom, user-facing side) of the eyelet or other connector portion is insulated, while an upper surface that has passed through the substrate makes electrical contact with the active region. The variation shown in FIG. 12, in which the connectors (snaps) are attached to a separate piece of substrate that is folded back over to make contact may be used to make a direct electrical contact with an edge of the active region.

FIGS. 15A and 15B illustrate another variation of a cantilever electrode. FIG. 15 shows a top view of the neurostimulator-facing side of the electrode apparatus. In this example, as before, a pair of connectors 1515, 1517, shown as snaps in this example, are separated by between 0.7 and 0.8 inches. Thus, a neurostimulator can be connected to the first electrode portion (region 1503). A second electrode portion (region 1505) is connected to the first electrode region by elongate body region 1507. In any of the variations described herein, one of the connectors 1515 makes electrical connection to the first active region 1533 on the first electrode portion 1503, while the second connector 1517 may connect to the second active region 1535 of the second electrode portion 1505. The second connector 1517 may connect via an electrical trace 1538 that may be present on the top or bottom of (or within) the flexible substrate forming the body of the electrode apparatus. In FIG. 15A, the connecting trace extends down the elongate body region 1507 on the top surface, and may be insulated. As with any of the layers forming the electrically active region, the trace (and/or insulator) may be printed, silk-screened, deposited, or otherwise applied to the substrate. In this example, the second connector 1517 is not positioned over the first active region, which may prevent shorting of the first and second active regions; however in some variations the connectors may both be entirely or partially positioned over (on the opposite side of) the first active region.

Any of the electrode apparatuses described herein may include a passive or active electrical element (e.g., circuitry) to identify the electrode apparatus to the neurostimulator. In particular, described herein are electrode apparatuses using passive electrical identification in which a simple capacitive element is connected between the electrical contacts of the electrode device. The capacitive element may be a single capacitor forming a simple RC circuit between the electrical contacts. The capacitive element (e.g., capacitor) may be chosen so that at frequencies below the expected operating frequency of the electrode apparatus (e.g., less than about 30 kHz, less than about 25 kHz, less than about 20 kHz, less than about 18 kHz), the capacitive connection is effectively an open circuit, and does not interfere with the application of the neurostimulation ensemble waveforms. Above this threshold for the expected operating frequency, the capacitor may be sensed by detection circuitry on the neurostimulator. In particular, the resulting RC circuit between the two electrical contacts may have a characteristic resonance that can be detected by the detection circuitry on the neurostimulator. By selecting different capacitor types (capacitance values and resulting resonance) for different classes of electrode apparatuses, the detection circuitry may be able to determine the corresponding "type" (e.g., calm, energy, date and batch of manufacture, etc.) of the attached electrode apparatus. For example, the capacitive element (e.g., capacitor) may be configured so that its impedance increases with decreasing frequency, therefore blocking the low-frequency signals that could shunt between the connectors from the neurostimulator. For example, the capacitive element may have a lower impedance at high frequencies (in the MHz range) and a high impedance in the KHz range, effectively acting as a capacitive high-pass filter between the two connectors. The cut-off frequency for the high-pass filter may be less than 1 MHz (e.g., less than 900 KHz, less than 800 KHz, less than 700 KHz, less than 600 KHz, less than 500 KHz, less than 400 KHz, less than 300 KHz, less than 200 KHz, less than 100 KHz, less than 90 KHz, less than 80 KHz, less than 70 KHz, less than 60 KHz, less than 50 KHz, etc.).

FIGS. 16A and 16B illustrate two different types of cantilever electrode apparatuses, each having a capacitor connecting the electrode contacts. For example, in FIG. 16A, the first and second electrical/mechanical contacts 1615, 1617 are connected by a capacitive element 1646. The capacitive element may be a capacitor that is chosen so that frequencies within the neurostimulation operating frequency range (e.g., at frequencies below about 18 kHz, below about 20 kHz, below about 25 kHz, below about 30 kHz, etc.) the capacitor looks like an open circuit and therefore does not interfere with the application of the ensemble waveforms to the user. At higher frequencies (e.g., above about 18 kHz, above about 20 kHz, above about 25 kHz, above about 30 kHz, etc., and particularly in the MHz range), the capacitor has a characteristic response that can be sensed by the detection circuitry in the neurostimulator, e.g., which may detect the resonant frequency of the resulting RC circuit in the electrode apparatus. For example, in FIG. 16A, which illustrates one example of an "energy" electrode apparatus that may be used to evoke an energy effect as described above, the capacitive element may be a 16 pF capacitor 1646 (or any capacitor having a value of between about 1 pF and 200 pF, e.g., 10 pF, 11 pF, 12 pF, 13 pF, 14 pF, 15 pF, 16 pF, 17 pF, 19 pF, 19 pF, 20 pF etc.). In contrast, the electrode apparatus shown in FIG. 16B, which may describe a "calm" type of electrode apparatus, may have a different characteristic capacitive element 1646' such as a 100 pF capacitor that resonates at a different frequency. In FIG. 16B, the capacitive element 1646' is also connecting the two electrical contacts 1615' and 1617' that each connect to an active region on the back of the electrode apparatus. In this example, at 3 MHz the capacitive elements (capacitors) of both electrode apparatuses (shown in FIGS. 16A and 16B) resonate, however, at 1 MHz only the 100 pF capacitor of FIG. 16B resonates, while the 16 pF capacitor of FIG. 16A does not. Thus the neurostimulator apparatus may be adapted to detect both when an electrode apparatus is attached (by examining the response at 3 MHz), and then by checking for a response at a second frequency range such as 3 MHz or thereabout, determine which type of electrode apparatus is attached (e.g., a calm or energy category of electrode apparatus).

Figure 17:
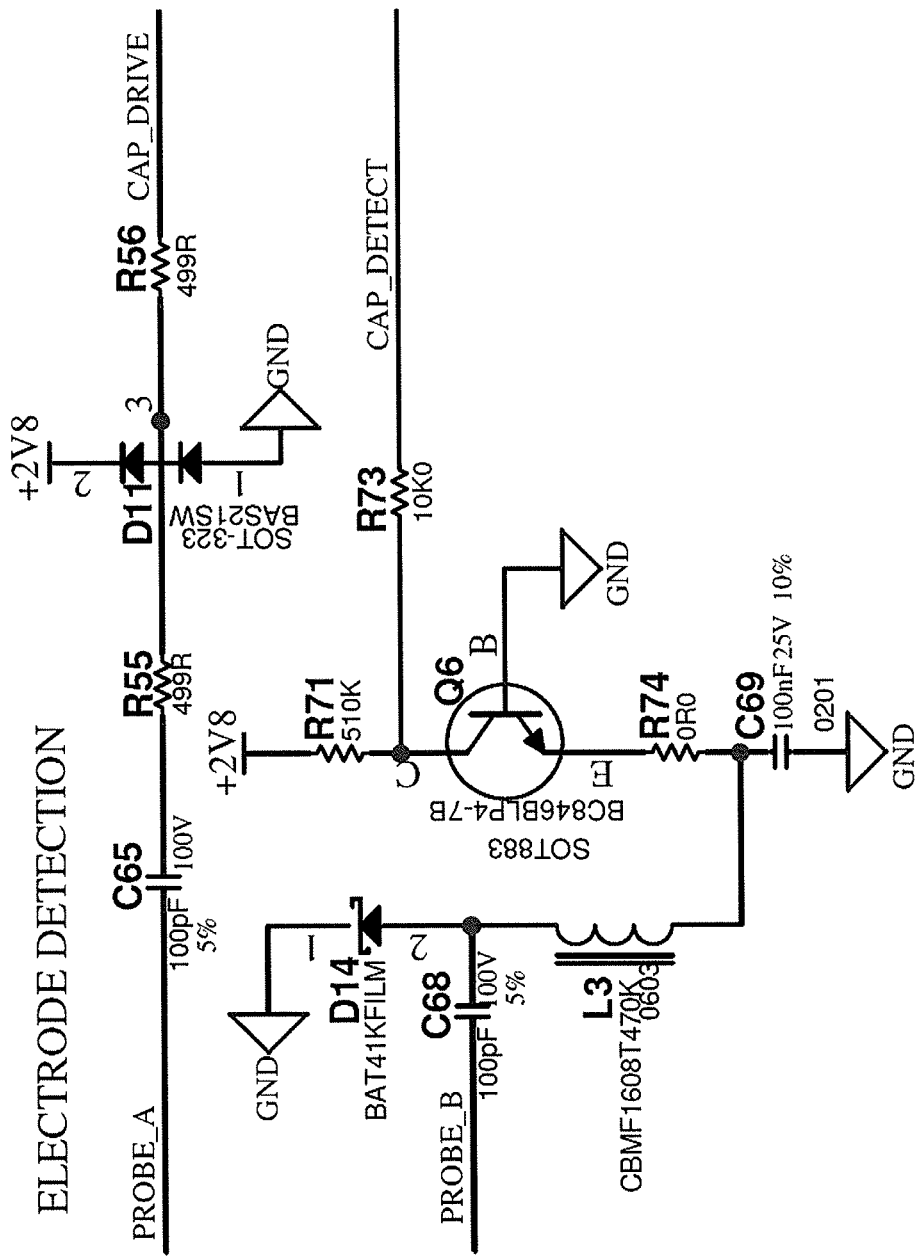
FIG. 17 is one example of a detection circuit that may be used to detect connection and or the type or identity of an electrode apparatus; the detection circuit may be included on a neurostimulator to detect some variations of the electrode apparatuses described herein.

For example, FIG. 17 illustrates one example of a detection circuit that may be used (e.g., included in a neurostimulator) to determine if, and what type, of electrode apparatus is attached to the neurostimulator. In this example, the probe A and probe B portions communicate with the first and second contacts, respectively, on the electrode apparatus to which the neurostimulator is attached. Probe A acts as the drive line to the capacitive element on the electrode assembly (which may be referred to as a detection capacitor or detection capacitive element) connected between the electrical (or electrical and mechanical, e.g., snaps) connectors of the electrode apparatus, while Probe B includes the sensing ("capacitive detection") circuit. The circuitry shown in FIG. 17 is only one example of sensing circuitry that may be used to detect the capacitor on the electrode apparatus, including the category of electrode apparatus based on the electrical (RC) characteristics of the electrode apparatus. In general, sensing circuitry may apply one or a plurality of high-frequency currents between the electrical connections (anodic, cathodic) of the electrode apparatus to identify the RC characteristics (e.g., resonance) of the detection capacitor on the electrode apparatus.

The detection circuit of the neurostimulator shown in FIG. 17 may be connected to a microcontroller or other logic circuit to detect a signal (i.e. voltage) indicating resonance of the 'in-series' capacitor mounted between the electrode-connecting traces of the electrode apparatus. The microcontroller or other logic circuit may also incorporate a clock or other timing circuit in order to determine the latency to resonance. In addition to the presence and/or amplitude of resonance, the latency at which resonance begins can be used to distinguish an electrode apparatus circuit having a particular capacitance value (which may include stray capacitance of all connected traces etc. on the electrode assembly) from another capacitance value.

Alternatively or additionally, in some variations, an electrode apparatus such as the cantilever electrode apparatuses described herein may include active circuitry such as a surface mounting chip to identify the electrode apparatus and/or for security. For example, when the electrode apparatus include a substrate that is a flex circuit, the circuitry may be configured to provide a unique identifier, and/or a counter that may be increment with use(s).

Any of the electrode assembly embodiments described herein may additionally or alternatively include an identification tag configured to designate the electrode assembly type (e.g., energy, calm) and/or other identifying information or use information about the electrode assembly. An identification tag may be disposed on a surface of the substrate, for example, on an outer (not skin-facing) surface of the substrate, or on a connector physically coupled to the substrate. Any suitable identification tag(s) may be used, for example, a Bluetooth transmitter, a Bluetooth Smart beacon, an RFID tag, a near-field communication tag, a resistive element, a capacitive element, a microcontroller, and/or a visual identifier such as a bar code, a QR code, a light transmitter, or an image. The identification tag may serve to identify one or more characteristics of a particular electrode assembly. For example, the identification tag may uniquely identify an electrode assembly's: model (e.g., calming effect, energizing effect, or focusing effect), brand, manufacturer, date and/or time of manufacture, physical size (e.g., small, medium, or large), or stimulation capacity (for example, as determined by the amount of Ag and Ag/AgCl and/or hydrogel present in the electrode assembly).

As described above in reference to a capacitive element for identification of the electrode assembly, an electrical stimulation system may be adapted for use with an identification tag of an electrode assembly. Further, any of the controllers that may be used with the neurostimulators described herein may be configured to recognize (and the electrode assembly and marker may be configured so as to be recognizable) by a controller, e.g., a specialized remote control, smartphone, tablet, etc. In some such variations, the controller may include an electronic reader, electronic receiver, or image reader configured to detect and recognize the identification tag. In some variations the neurostimulator may pass along the identifying information to the controller specifically. For example, in one embodiment of the system, the controller includes a Bluetooth receiver, and the electrode assembly includes a Bluetooth transmitter or Smart beacon; in another embodiment, the controller includes an RFID reader, and the electrode assembly includes an RFID tag. In another embodiment, the controller includes a near-field communication antenna, and the electrode assembly includes a near-field communication tag. Additionally or alternatively, the controller may include an electrical connector and resonating circuit, such as a series of electrical pins, and the electrode assembly may include a resistive element or a capacitive element.

In one embodiment of a system including an electrode assembly, the electrode assembly and the controller (and/or the neurostimulator) each includes a microcontroller (e.g., a microprocessor or a programmable chip) programmed with firmware. The firmware, when run, allows for one-way or two-way communication between the coupled microcontrollers and further allows the microcontrollers to run an authentication protocol to query and confirm that the controller and the electrode assembly are authentic and authorized for use together.

In another embodiment, the controller (and/or neurostimulator) may include an image reader configured to detect a visual identification tag, and the electrode assembly may include a visual identification tag. In some embodiments, the image reader includes an image capturing mechanism (e.g., a camera, a lens, a bar code reader, a QR code reader, or a diode) and a microprocessor, and the visual identification tag of the electrode assembly includes: a bar code, a QR code, a light transmitter, an image, or other visual identifier.

The controller and/or neurostimulator of various embodiments may be programmed such that, if the controller cannot recognize the identification tag of an electrode assembly, the controller will not provide a stimulating current to the electrode assembly. For example, if a controller running is communicatively coupled to an electrode assembly having an unrecognized identification tag (or lacking such a tag), the controller may render the coupled electrode assembly inoperable. No stimulating current will be delivered to the electrode assembly. In such a manner, the electronic identification tag may prevent the system from operating with unauthorized electrode assemblies.

In some embodiments, when a controller and/or neurostimulator is communicatively coupled to an electrode assembly having an identification tag, the microprocessor of the controller and/or neurostimulator may compare the detected identification tag to a database of identification tags stored in a memory to confirm that the detected identification tag matches a known identification tag. Additional electrode-specific information may be stored in the database with each known identification tag, such as, for example: the appropriate stimulation protocol for the respective electrode, acceptable threshold levels (e.g., temperature, pH, and/or current values), acceptable operating parameters (e.g., temperature, humidity, etc.), and the like. In other embodiments, the microprocessor of the controller and/or neurostimulator may transmit data indicative of the detected identification tag to a remote server where a database of known identification tags is stored, and the remote server may compare the detected identification tag to the known tags, and if there is a match, transmit data associated with the known tag back to the controller. With the information obtained from the database, the controller and/or neurostimulator may test the electrode assembly and current conditions to confirm the electrode(s) are still within acceptable operating specifications (e.g. temperature, humidity, force, etc.); the controller may then deliver a programmed stimulation protocol to a user.

Sensors

Instead of or in addition to the detection capacitor described above, any of the variations described herein may also include one or more sensors. These sensors may be read by the neurostimulator, which may analyze, store, and/or transmit the sensed information to the controller and/or a third party platform. For example, any of the electrode apparatuses described herein may include one or more sensors that may provide information useful to determine when the electrode apparatus has degraded, and/or requires replacement, refurbishing, or removal. Although in many of the examples provided herein the electrode apparatus is configured to be single use, and disposable, in any of the examples described herein the electrode apparatus may be durable or multi-use.

For example, the apparatuses (including devices and systems) and methods described herein may be configured to determine when (or if) the electrode apparatus for TES neuromodulation has degraded and requires replacement, refurbishing, or removal. Using only electrode apparatuses that meet quality criteria is beneficial so that TES neuromodulation is comfortable for a subject and reliably induces a desired cognitive effect. In general, the apparatuses described herein can be used with any TES system, including the wearable neuromodulators described herein, as well as other non-wearable TES systems, including TES systems with a portable (e.g. tabletop or handheld) controller unit.

For example, a TES apparatus may incorporate an electrode apparatus or a set of electrode apparatuses. Disposability and replaceability may be important features for components of the system that contain electrodes, because electrodes typically degrade in important ways that affect comfort, efficacy, and usability.

As described above, at least one anodic electrode contact and one cathodic electrode contact are typically used with a transdermal electrical stimulation apparatus for inducing a cognitive effect in a subject. The TES apparatus ("neurostimulator") generally includes a durable portion that couples with a disposable or replaceable portion (electrode apparatus) comprising the electrodes. Also as briefly described above, the durable or reusable portion may include a processor and/or controller, power source, wireless transmitter-receiver, and a connector for connecting to two or more electrodes in the disposable portion to drive stimulation between the electrodes (active regions) to induce a cognitive effect in a subject wearing the apparatus. As used herein, a disposable element may refer to a limited-use item (e.g., single-use or limited multiple-use, including 2-3 uses, 2-5 uses, 2-7 uses, 2-10 uses, or less than 5 uses, less than 10 uses, etc.). A disposable element may be used once (or 2-3 times, etc.) and then removed from the apparatus and replaced with a new element. In particular, the electrode apparatuses described herein may be disposable elements that include a conductive material (e.g., conductive gel, conductive adhesive, etc.) and/or adhesive that is only reliably useful a limited number of times before needing to be replaced or refurbished.

Beneficial features of transdermal electrodes that degrade over time and over use include adherence, pH buffering, and uniform distribution of current across the face of the electrode. In general, an electrode apparatus may define use cases for which properties (e.g., adhesion, pH buffering, uniform distribution of charge) are within acceptable ranges. Methods for determining when an electrode apparatus requires replacement or refurbishing may use one or more product specification, compare that value to one expected after a detected amount and type of electrode apparatus use, determine whether or not the electrode apparatus quality is outside a specified range, and then either inform a user that the electrode apparatus requires replacement or refurbishment or automatically stop a neurostimulation (or lock out the neurostimulator so that a waveform ensemble cannot be started).

Adherence is a first beneficial property of electrode apparatuses that degrades over time. In general, apparatuses and methods for maintaining adhesive properties over time and use may include a way to determine or estimate when the adhesive properties of an electrode apparatus have degraded such that the electrode requires replacement or refurbishment. The quality of an adherent active region of the electrode apparatus may be reduced each cycle of adherence to a subject and removal from the subject. For instance, a hydrocolloid adhesive component of an electrode apparatus on the dermal-facing portion of a disposable electrode apparatus may degrade when it is used or if it gets wet (e.g. due to rain, sweat, or a liquid spill). An adherent electrode apparatus will also generally require a storage device such as wax paper or plastic between uses to protect the adhesive for subsequent adherences of the unit on the subject's skin. The act of placing an adherent electrode apparatus onto a protective covering (or equivalently placing a protective covering on the electrode) may also somewhat degrade the adhesive properties of the electrode apparatus despite the composition of the covering being selected so as to minimally affect the adhesive. Transdermal electrode components of the system that become less adherent are less than ideal for any number of reasons, including that an electrode apparatus may partially or completely separate from a user's skin (e.g. fall off); or the impedance of electrical connection between an active region and a user's skin may increase because the physical connection is not uniform across the electrically conductive portion of the electrode apparatus.

Adhesive materials of an adhesive electrode apparatus may include a portion of the active region intended for delivering electrical stimulation (i.e. adhesive and conductive) and/or a portion of the electrode apparatus that is not intended for delivering electrical stimulation that is configured to cause an active region/portion of the electrode to be in close physical contact (i.e., low impedance) contact with a user's skin.

Buffering pH is a second beneficial property of electrode apparatuses that degrades over time. Causing current to be distributed evenly across the transdermal face of an electrode is a third beneficial property of electrode apparatuses that degrades over time. Uniform current distribution and pH buffering can be improved by features of electrode apparatuses, including the water composition of a hydrogel component of an electrode apparatus for TES and the amount of Ag and Ag/AgCl contained in a component that couples an electric current through the active region to the skin. Water in a hydrogel component of an electrode apparatus (or other water-containing conductive material) is consumed as net charge is transferred into a subject's body. Ag/AgCl components of an electrode (including components coated with Ag/AgCl and Ag/AgCl ink) improve the efficiency of charge transfer to tissue (essentially a salt solution) and are also consumed during electrical stimulation.

Charge imbalanced TES waveforms are often necessary for inducing cognitive effects, but these waveforms can consume Ag, Ag/AgCl, and water, causing the degradation of transdermal electrodes and limiting their effective use.

If too much water in an active region is consumed, the efficiency of redox reactions is reduced leading to pH changes that may cause skin irritation, pain, and/or tissue damage. Thus, in some variations a pH sensor may be sufficiently sensitive such that a user (or the neurostimulator and/or controller, for automated systems) can stop or turn down the net charge of stimulation or replace an electrode apparatus before irritation, pain, or tissue damage occurs. A pH-sensitive material may be incorporated in a visible portion of an electrode apparatus so that a user (or third party) can determine if pH changes are occurring. Alternatively, a pH sensor may be configured to detect pH changes and transmit this information to a visible part of an electrode apparatus, to a durable portion of a neurostimulator/controller, or to a computing device connected to a durable portion of a neurostimulator/controller in a wired or wireless fashion.

A TES system can automatically or by user input keep track of parameters of use that affect electrode quality, including but not limited to: number of adherence and removal cycles from the skin; number of TES sessions; duration of stimulation; cumulative net charge delivered; cumulative absolute charge delivered; peak current delivered; and the like. A Coulomb counter may be included in the electronic circuitry of a neurostimulator system to determine the amount of charge transferred to a subject during a stimulation session.

In some variations, a sensor contained in an electrode apparatus can be used to determine when the electrode apparatus has been placed on a user. This may be advantageous, because it does not require a self-report by a user each time an electrode apparatus is adhered or removed from the skin. Effective sensors for determining whether an electrode apparatus has been adhered to or removed from a subject's skin include, but are not limited to: an accelerometer, a capacitive sensor, an EMG sensor, an optical sensor (e.g. a light-emitting diode or other light source and a diode, CMOS, or other detector to measure reflectivity), a microphone, or another sensor effective for determining whether an electrode apparatus is adhered to or removed from a user's skin. For example, one or more accelerometers may be contained within an electrode assembly; in a durable assembly coupled to the electrode apparatus; or both.

In general, an appropriate signal processing and algorithm workflow may be applied to data from the one or more sensors in the above list to determine whether an electrode apparatus has been adhered to or removed from a user. Determining whether an electrode apparatus has been placed (adhered) onto a subject's body (generally, a subject's skin) may be achieved by a non-transitory computer-readable storage medium storing a set of instructions capable of being executed by a remote processor (including a smartphone, smartwatch, tablet computer, or the like), that when executed by the computing device containing the remote processor causes sampling of at least one sensor (e.g. a single-axis or multi-axis accelerometer) over time, and applies appropriate signal processing and signal detection algorithms to identify when an electrode is adhered to a subject or removed from a subject.

For example, with an accelerometer sensor, adherence of an electrode apparatus to a subject could be determined or estimated based on a sequence of accelerometer signals corresponding to a subject holding the electrode apparatus in their hand; followed by the user slowly placing the electrode apparatus onto his/her skin; followed by a period of time when accelerometer signals that are consistent with the biomechanics of the part of the body to which the electrode was adhered are detected (which can be known by the type of electrode apparatus and thus appropriate body positioning thereof; or by other means such as an image taken by a smartphone camera). One skilled in the art of wearable sensors and signal processing will recognize that signals from each of the sensors listed above can be used to define an algorithm that determines electrode-dermal connections with an appropriate reliability and sensitivity.

In another exemplary embodiment, a sensor may be an imaging sensor (i.e., camera) oriented by the user (or a third party) such that the field of view of the camera includes a part of a user onto which an electrode apparatus is adhered and/or removed. In another example, the sensor is a microphone and detects the adherence or removal of the electrode apparatus based on a sound generated by the electrode apparatus. In some embodiments, electrode apparatuses are designed to incorporate an element or feature that generates sound when adhered to a subject or removed from a subject. For example, an electrode apparatus may generate a sound when manipulated to be placed on a curved portion of a subject (i.e. a snapping sound). Alternatively, the sound signal may relate to connecting an electrode apparatus to a durable portion of the neurostimulator, such as a snap connector or set of snap connectors.

In some instances, use of an electrode apparatus does not require a sensor and may be self-reported by a user or reported by a third-party observing the user (e.g., through a user interface on a display of a TES system or a smartphone or other computing device). In other instances, whether an electrode apparatus has been used relies on a non-transitory computer-readable storage medium storing a set of instructions capable of being executed by a remote processor (including a smartphone, smartwatch, tablet computer, or the like), that when executed by the computing device containing the remote processor causes an entry to be made in a database locally or remotely (i.e. on a server connected via the Internet) or other machine-readable communication that relates to the use of the electrode apparatus for TES by a particular subject.

Effective transdermal electrical stimulation for neuromodulation may require appropriately placed active regions of an electrode apparatus. Naïve or less experienced users may need to adhere and remove an electrode apparatus several times before commencing electrical stimulation. In such cases, a conservative estimate of the number of adherence/removal cycles may be necessary for each TES stimulation delivered. For example, an estimate of three adherences and removals could be made for each TES stimulation event in novice or naïve subject.

In general, an electrode apparatus may have a sensor that measures the amount of time since the electrode has been removed from its original airtight packaging. For example, a TES electrode may be stored in opaque packaging and include a material that changes color or otherwise indicates exposure to light. Other materials may be used in addition to or instead of the light-sensitive material to indicate exposure to particular temperature, humidity, or other ambient environmental factors that may degrade electrode quality.

In general, a timer or alarm may determine how long an electrode apparatus has been outside of its packaging and/or used for TES. A timer or alarm may be configured to be: integrated in the assembly containing the adhesive transdermal electrode apparatus; self-contained and included in the airtight packaging of a disposable transdermal electrode apparatus or set of electrode apparatuses; integrated in the airtight packaging of a disposable electrode apparatus or set of electrode apparatuses; and/or achieved by a non-transitory computer-readable storage medium storing a set of instructions capable of being executed by a remote processor (and particularly a smartphone, smartwatch, or the like), that when executed by the remote processor causes a timer to determine the amount of time since an airtight packaging of a disposable electrode apparatus or set of electrode apparatuses is opened. In some embodiments, the set of instructions capable of being executed by a remote processor uses an integrated sensor of a portable computer; smartphone; smartwatch; or tablet computer containing the remote processor to determine when the airtight packaging is opened (e.g. by analyzing signals from a microphone sensor to detect the sound of the electrode packaging opening).

In other embodiments, a durable unit of a TES system (e.g., neurostimulator) includes a sensor and other necessary components for measuring exposure to light, heat, humidity, etc. and determines when a particular instance of an electrode apparatus is in proximity and thus is expected to receive similar environmental exposure. In yet other embodiments, a non-transitory computer-readable storage medium storing a set of instructions capable of being executed by a remote processor (and particularly a smartphone or the like), that when executed by the processor causes the processor to determine one or more of temperature, humidity, and exposure to direct sunlight either continuously or intermittently since the electrode apparatus has been removed from airtight packaging. In such an embodiment, a geolocation sensor (e.g. GPS) of the computing unit (e.g. smartphone) can be associated with publicly available weather data to estimate exposure without requiring a sensor.

In general, degraded electrode apparatuses of the present invention may be configured for recycling so that more durable portions of the electrode apparatus can be reused while those parts that have degraded are replaced or refurbished.

In general, a user may wear a neuromodulation device and apply one or more waveforms (e.g., waveform ensembles) using the neuromodulation device to induce a cognitive effect. The apparatuses described herein may be configured to provide one or more cognitive effects. In general, a cognitive effect may include any induced cognitive effect that is perceived subjectively by the recipient as a sensory perception, movement, concept, instruction, other symbolic communication, or modifies the recipient's cognitive, emotional, physiological, attentional, or other cognitive state. For example, an effect of electrical stimulation is one or more of inhibition, excitation, or modulation of neuronal activity. Specific examples of cognitive effects may include relaxation, enhanced attention, mood elevation, increased energy (e.g., physiological arousal, increased subjective feelings of energy), or the like. Cognitive effects may be stereotypical across a population (though with individual variation and degree) and may be demonstrated by any appropriate means, including by subject reporting, objective testing, imaging, physiological recording, etc. Particular cognitive effects evoked may depend upon the position of the electrodes of the apparatus with respect to the subject, and/or the stimulation parameters described herein. The apparatuses described herein may be optimized to achieve a specific cognitive effect.

A cognitive effect of neuromodulation may cause a change in a user's level of energy, fatigue, sleepiness, alertness, wakefulness, anxiety, stress, sensory experience, motor performance, formation of ideas and thoughts, sexual arousal, creativity, relaxation, empathy, and/or connectedness that is detectable by an objective measurement (e.g. behavioral assay) and/or subjective report by the user.

For example, a cognitive effect of neuromodulation may cause a change in an emotional state of the user where the change is detectable by an objective measurement (e.g. behavioral assay) and/or subjective report by the user and an emotion affected is selected from the list including but not limited to: affection, anger, angst, anguish, annoyance, anxiety, apathy, arousal, awe, boredom, confidence, contempt, contentment, courage, curiosity, depression, desire, despair, disappointment, disgust, distrust, dread, ecstasy, embarrassment, envy, euphoria, excitement, fear, frustration, gratitude, grief, guilt, happiness, hatred, hope, horror, hostility, hurt, hysteria, indifference, interest, jealousy, joy, loathing, loneliness, love, lust, outrage, panic, passion, pity, pleasure, pride, rage, regret, relief, remorse, sadness, satisfaction, self-confidence, shame, shock, shyness, sorrow, suffering, surprise, terror, trust, wonder, worry, zeal, and zest.

In some variations, the cognitive effects evoked by the apparatuses described herein may be positive cognitive effects; positive cognitive effects may refer to cognitive effects resulting in an increase in alertness, an increase in relaxation, a decrease in fatigue, and a decrease in anxiety, an enhancement in motor performance, an increase in recall, and an increase in empathy.

A cognitive effect of neuromodulation may cause a change in brain activity measured by one or a plurality of: electroencephalography (EEG), magnetoencephalography (MEG), functional magnetic resonance imaging (fMRI), functional near-infrared spectroscopy (fNIRS), positron emission tomography (PET), single-photon emission computed tomography (SPECT), computed tomography (CT), functional tissue pulsatility imaging (fTPI), xenon 133 imaging, or other techniques for measuring brain activity known to one skilled in the art.

A cognitive effect of neuromodulation may be detectable by a physiological measurement of a subject, including but not limited to measurements of the following: brain activity, body temperature, electromyogram (EMG), galvanic skin response (GSR), heart rate, blood pressure, respiration rate, pulse oximetry, pupil dilation, eye movement, gaze direction, measurement of circulating hormone (e.g. cortisol or testosterone), protein (e.g. amylase), or gene transcript (i.e., mRNA); and other physiological measurement. A cognitive effect of neuromodulation may be detectable by a cognitive assessment that takes the form of one or more of: a test of motor control, a test of cognitive state, a test of cognitive ability, a sensory processing task, an event related potential assessment, a reaction time task, a motor coordination task, a language assessment, a test of attention, a test of emotional state, a behavioral assessment, an assessment of emotional state, an assessment of obsessive compulsive behavior, a test of social behavior, an assessment of risk-taking behavior, an assessment of addictive behavior, a standardized cognitive task, an assessment of "cognitive flexibility" such as the Stroop task, a working memory task (such as the n-back task), tests that measure learning rate, or a customized cognitive task.

In general, subjects treated with TES with appropriate electrode configurations (positions) and TES waveforms (waveform ensembles) may experience neuromodulation with cognitive effects including, but not limited to: enhanced focus and attention; enhanced alertness; increased focus and/or attention; enhanced wakefulness; increased subjective feeling of energy; increased objective (i.e. physiological) energy levels; higher levels of motivation (e.g. to work, exercise, complete chores, etc.); increased energy (e.g., physiological arousal, increased subjective feelings of energy); and a physical sensation of warmth in the chest.

In general, subjects treated with TES with appropriate electrode configurations (positions) and TES waveforms experience neuromodulation with cognitive effects including, but not limited to: a state of calm, including states of calm that can be rapidly induced (i.e. within about 5 minutes of starting a TES session); a care-free state of mind; a mental state free of worry; induction of sleep; a slowing of the passage of time; enhanced physiological, emotional, or and/or muscular relaxation; enhanced concentration; inhibition of distractions; increased cognitive and/or sensory clarity; a dissociated state; a state akin to mild intoxication by a psychoactive compound (i.e. alcohol); a state akin to mild euphoria induced by a psychoactive compound (i.e. a morphine); the induction of a state of mind described as relaxed and pleasurable; enhanced enjoyment of auditory and visual experiences (i.e. multimedia); reduced physiological arousal; increased capacity to handle emotional or other stressors; a reduction in psychophysiological arousal as associated with changes in the activity of the hypothalamic-pituitary-adrenal axis (HPA axis) generally associated with a reduction in biomarkers of stress, anxiety, and mental dysfunction; anxiolysis; a state of high mental clarity; enhanced physical performance; promotion of resilience to the deleterious consequences of stress; a physical sensation of relaxation in the periphery (i.e. arms and/or legs); and a physical sensation of being able to hear your heart beating.

Electrically Active Regions Having Sub-Regions

As discussed above, any of the electrode apparatuses herein may be flexible multi-electrode assemblies that are typically flexible such that two separate but connected regions of the electrode assembly conform to two or more body regions of a user, such as a portion of the user's forehead and/or neck and/or an area surrounding an ear. Conforming the multi-electrode assembly to the body portion of the user may result in increased comfort during electrical stimulation, increased uniformity in impedance, and improved cognitive effects. In some embodiments, the use of a unified assembly with multiple electrodes (e.g., multiple electrically active regions) may eliminate the need for connectors and/or cables between electrically active regions on the electrode assembly. The substrate of the electrode assemblies described herein may be a flexible nonconductive substrate onto which the electrically active regions are formed or placed.

Any of the electrode apparatuses described herein, including the cantilever electrode apparatuses or multi-electrode assemblies, may be disposable, and single-use or multiple-use, allowing use for a plurality of times before being disposed. Alternatively, the electrode apparatuses may be durable and reusable for any length of time, for example only requiring replacement or refurbishing of certain components or elements of the device or system. An electrode apparatus as described herein is not limited to the neuromodulation systems and techniques described herein, but may be used in other fields and/or applications. For example, the electrode apparatuses described herein may be used in fuel cells, medical applications (e.g. EEG, ECG, ECT, defibrillation, etc. . . . ), electrophysiology, electroplating, arc welding, cathodic protection, grounding, electrochemistry, or any other electrode application. An electrode apparatus may be used to target non-neuronal tissues and may be placed on any portion of the body. For example a flexible electrode system as described herein may be used for muscle therapy for healing an injury.

Figure 18B:
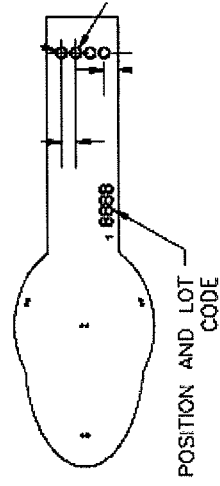
FIGS. 18A-18C illustrate a portion of an electrode apparatus including different sub-regions of active zones.
Figure 18A:
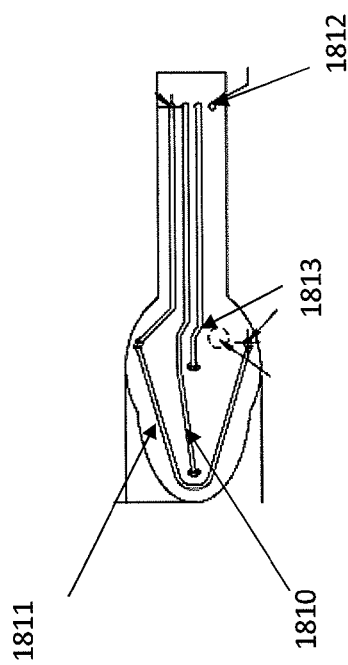
Figure 18C:
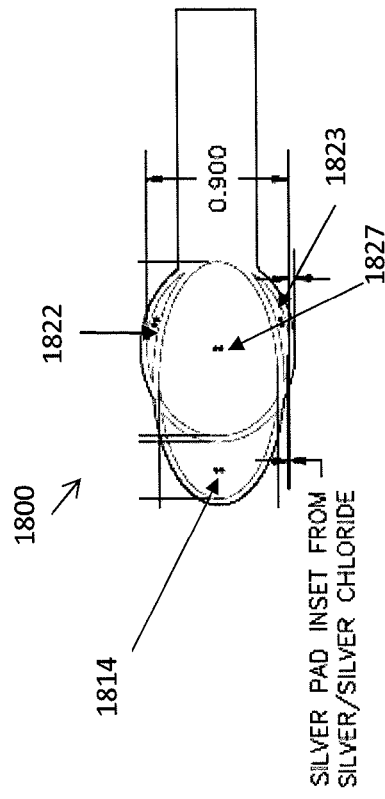

FIGS. 18A-18C illustrate one variation of a flexible electrode apparatus that includes a flexible substrate, at least two conductive traces, an adhesive component, and at least two electrodes. The electrode apparatus is preferably used for noninvasive neuromodulation, but can additionally or alternatively be used for any suitable applications, clinical or otherwise.

In FIG. 18A, a flexible substrate 1812 may include a first surface and a second surface, as shown in FIG. 18A (top view) and FIG. 18B (bottom view), respectively. The second (bottom) surface is opposite the first (top) surface. The flexible substrate may include two or more apertures each coated with an electrical conductor, such that the electrical conductor (e.g., carbon black, silver, etc.) delivers current between the first and second surfaces. As shown in FIG. 18C, the first surface may include one or more active regions 1814, such that current from the second surface is delivered to the electrodes on the first surface.

In general, an active region of an electrode may be divided up into multiple zones or sub-regions that can be individually and/or collectively driven and/or sensed from so that the size of the active region of the electrode apparatus can be increased and/or decreased as needed. This modification may be controlled by the neurostimulator and/or the controller (e.g., a control unit, including a control application that is operating on a smartphone, etc.), which may determine which groups of active regions of an electrode (typically anode or cathode) is active at a particular time. In some variations, multiple regions (sub-regions) of the active region are tied together so that they may operate together. This is illustrated, for example, in FIGS. 18A-18D.

Each sub-region of the active region may be separately or collectively coupled to a trace that connects to the power supply and/or controller. For example, FIG. 18A shows a substrate having multiple (e.g., three) conductive traces printed on an upper surface (though any surface, e.g., the top or bottom surface, may be used). The conductive traces may be printed, silk-screened, etched, soldered, welded, or otherwise attached to the surface. In some embodiments, the conductive surface may include more than two traces (e.g. FIG. 18A, three traces are shown). For example, a first trace 1810 on the back side of the portion of the apparatus shown is coupled though an opening in the substrate (which may be filled with a conductive material) to a first area of an electrode (1814 in FIG. 18C); a second trace 1811 is coupled to second and third electrode areas (1822, 1823 in FIG. 18C), where these regions are electrically shorted (connected) together; a third trace 1813 is coupled to fourth electrode area (1827 in FIG. 18C) or alternatively may be connected to a secondary electrode on either the same assembly or a second assembly. The traces may be connected to an electrical/mechanical connector for coupling to the neurostimulator. This connection may be direct, or they may be coupled to a chip, resistor, capacitor, or the like (including a capacitive element as discussed above). The sub-regions shown in this example may therefore be used to provide a single electrode apparatus that can have one or more (e.g., two) active regions that can have different dimensions, and therefore be used on different regions of the body. In practice this may allow a single electrode apparatus having at least one active region that is configured to have multiple sub-regions in which different combinations of sub-regions may be separately operated together to provide a particular shape and/or pattern for the active region. Thus, whereas separate electrode apparatuses configured for energy and relaxation are described above (e.g., FIGS. 16A and 16B, respectively), in some variations a single electrode apparatus may by dynamically configured or configurable to evoke either "energy" (using a large, relatively circular active region for placement behind the ear/on the mastoid region) or "calm" (using a more rectangular active region for placement behind the neck).

Figure 19C:
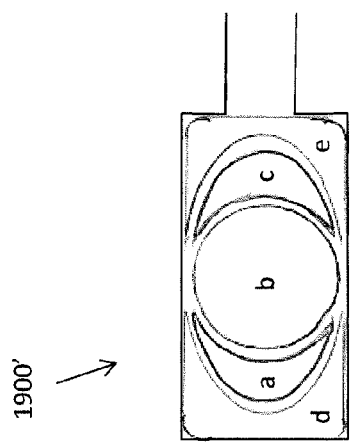
FIGS. 19B-19D show bottom, side sectional and top views, respectively of another variation of an electrode apparatus having multiple sub-regions forming an active region of the electrode on the bottom surface.
Figure 19D:
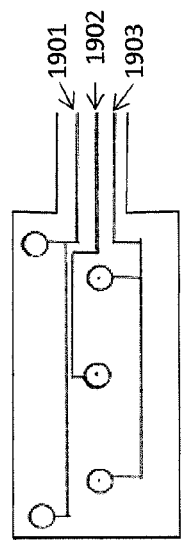
Figure 19A:
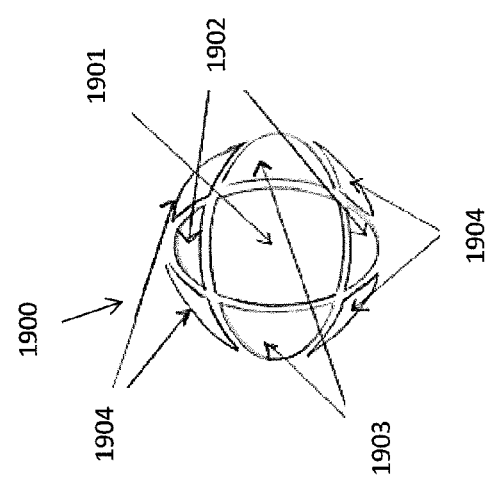
FIG. 19A is a bottom view showing multiple sub-regions forming an active region of the electrode on the bottom surface, similar to that shown in FIG. 18C.
Figure 19B:
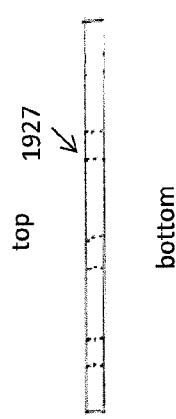

FIGS. 19A-19D show other variations of active region of an electrode apparatus in which the active region is formed of a plurality of sub-regions that may be operated together in different sub-combinations, so that they may be differentially stimulated or read from, and the size or shape of the effective active region on the surface, and thus the electrical stimulation area, may be adjusted to effect different neuromodulation outcomes. Selecting specific sub-regions of the active region from an array of active sub-regions on the surface can be used to focus stimulation to a preferred area, compensate for changes in impedance (e.g. if part of the array shifts away from the skin during use), avoid uncomfortable areas, compensate for changes in electrochemistry to improve comfort (e.g. reduced AgCl in a particular electrode vs. another) or other uses. As shown in FIGS. 19A-19D, a conductive trace on the opposite (top) surface from the active region (see, e.g., FIG. 19D) may extend to a distinct active sub-region on the bottom surface, as shown in FIG. 19B. In this example, FIG. 19D is the top surface and FIG. 19B is the bottom surface of the same electrode region. Each conductive trace may control the electrical stimulation delivered by the sub-region or sub-area to which it is coupled. For example, activating electrode areas 1901 and 1902 may induce a first cognitive effect in a user, while activating electrode areas 1901, 1902, and 1903 may induce an alternative or modified cognitive effect in a user. Any combination of electrode areas may be used to achieve the desired neuromodulation outcome. FIG. 19B illustrates how three conductive traces may be positioned to control three electrode areas. For example, trace 1901 (FIG. 19D) controls areas d and e, trace 1903 controls areas a and c, and trace 1902 controls area b. In some embodiments, any number of electrode areas may be positioned on each electrode. Further, the electrode active sub-regions may be clustered in an area of the flexible assembly or distributed over a region of the flexible assembly. Electrical current from a controller or current delivery device (neurostimulator) may be delivered to the traces through one or more connectors or pins, for example pogo pins or conductive snaps, extending from the controller to the second surface or from the second surface to the controller, such that the pogo pins/snaps are electrically connected with the traces. Further, electrical current from the conductive traces on the top surface may be delivered to the electrode sub-regions on the bottom surface through one or more conductive apertures 1927 or through holes in the nonconductive flexible substrate, as shown in the side sectional view of FIG. 19C. FIG. 19A shows another variation of a bottom portion having an active region for the electrode that includes a plurality of different sub-regions that may be differently operated together to provide different effective active regions (e.g., an active region formed of sub-regions 1902 and 1901 to provide a first oval configuration, an active region formed of sub-regions 1903 and 1901 to provide a second oval configuration, an active region formed of 1904, 1903, 1902 and 1901 to provide a large circular region).

In some variations, a second electrode having an active region formed of multiple sub-regions that may be operated in sub-combinations may be present on the electrode apparatus, e.g., in a spaced relationship from the first electrode. For example, the two electrodes may be spaced apart by about 1 inch, 2 inches, 3 inches, 4 inches, 5 inches, etc. The spacing may be along the connecting region of the substrate, as discussed above (e.g., following the shortest continuous path along the substrate). The electrodes may be spaced apart by any suitable distance so that they may target the two regions on the user's head.

As used herein the path length of the flexible elongate member separating the first and second electrode portions (which in some variations may be a cord, cable, wire, etc., or it may be a portion of the flat substrate, as illustrated above in FIGS. 1A-5) may refer to the length of the connector if it were made straight; this may also be referred to as the distance of travel between the first and second electrode portions. This distance is typically sufficient to allow the first electrode portion to be placed at a first location on the user's head (e.g., the front of the user's head), then adjust (e.g., bend, flex, etc.) the connecting region so that the second connecting region can be placed at a second region on the side of the head, back of the head or neck region. The connecting region extends between the two, so that the path length is the path taken by an electrical trace or wire extending from one of the proud connectors linking the first electrode portion to the electrical stimulator to the second electrode portion.

Within the same overall active region (e.g., 1800 in FIG. 18C, 1900 in FIG. 19A, 1900' in FIG. 19B) the individual sub-regions may be arranged such that current resists traveling through the hydrogel to "inactive" electrode areas, which are not part of an active sub-region being used. Thus, in some variations the adjacent regions may be spaced apart from each other (e.g., so that there is at least 1 mm, 2 mm, etc. between the hydrogel of different regions). In some variations the unused sub-regions may be set to "float" (electrically unconnected to ground or to an active region). In general at least one sub-region is coupled to the first surface and electrically coupled to the second surface through two or more conductive apertures, as described above. Flexible electrode assemblies containing two or more spatially distinct electrodes are advantageous by permitting stimulation between the two electrodes when they are adhered to the skin.

Figure 20A:
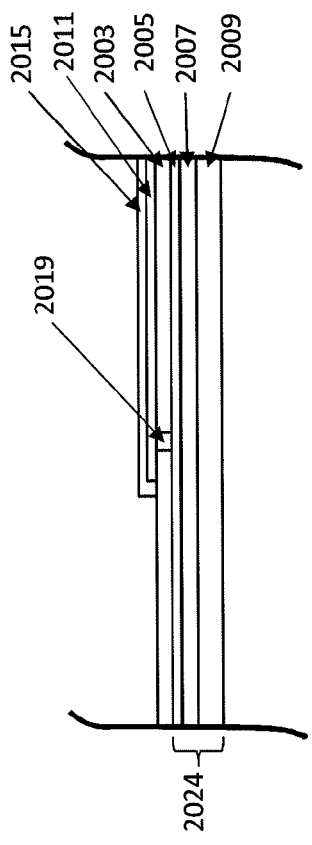
FIG. 20A shows an exemplary (not to scale) sectional view through an active region of an electrode fed by a conductive trace.

FIG. 20A is a section through one variation of an active region of an electrode apparatus, showing different layers that may be used to form the active region. For example, in FIG. 20A, an electrode trace 2011 extends on a top surface of a substrate 2003 (such as a polymeric material appropriate for use in a flexible circuit, e.g., Kapton). This trace 2011 may be insulated (e.g., by an insulating covering) 2015. An opening through the flex circuit (e.g., hole 2019) may include a conductive material (e.g., carbon black, silver, etc.) resulting in electrical communication between the trace 2011 and a portion of the electrically active region 2024, that (in this example) includes a layer of conductive metal (e.g., Ag) 2005, a layer of sacrificial conductor (e.g., Ag/AgCl) 2007 that completely covers the Ag layer and an outer, skin-contacting layer of hydrogel 2009 that is in electrical contact with the Ag/AgCl layer, and may also completely cover it (or cover it in conjunction with an insulator). The sacrificial Ag/AgCl layer 2007 in this example may also extend beyond the border of the conductive (i.e. Ag) layer 2005 to avoid shorts between the conductive (i.e. Ag) layer and the skin-contacting layer of hydrogel 2009 (i.e. extends beyond it around its entire circumference, including any internal exclusions or holes in the layer, for instance to permit a snap conductor to be placed).

Figure 20C:
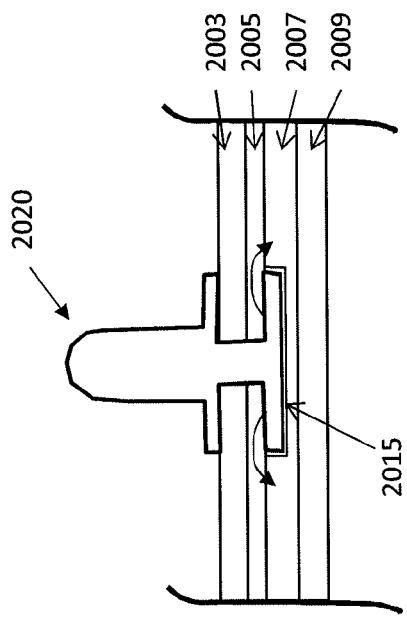
FIG. 20C is a slightly enlarged view of FIG. 20B.
Figure 20B:
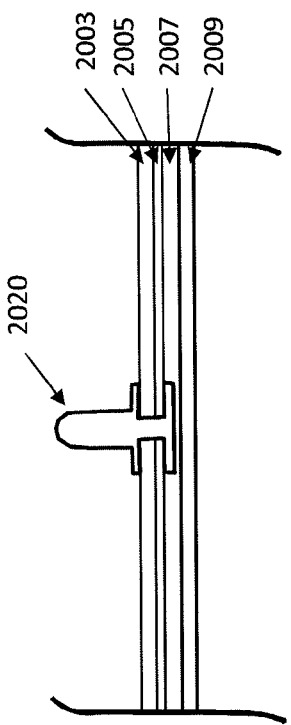
FIG. 20B shows a section view though an active region directly connected to a (snap) connector for coupling to a neurostimulator.

FIG. 20B shows a partial section through a portion of an active region that is electrically connected to an electrical and/or mechanical connector via an indirect connection pathway and thereby connects to an electrical stimulator (e.g., such as a neurostimulator). This configuration is similar to that seen in the second active region 135 in FIG. 1D or 435 in FIG. 4D. In some variations the electrode includes an active region that is directly connected to the connector, such as the first active region 133 in FIG. 1D or the first active region 433 in FIG. 4D. An example of this arrangement is shown in FIG. 20B and in detail in FIG. 20C.

In FIG. 20B the active region of the electrode includes a contact (shown as a snap or pin) for connection to the electrical stimulator (e.g., neurostimulator). In this example, the connector 2020 penetrates the substrate 2003 and a layer of conductive material (shown as a conductive metal, e.g., Ag) 2005 and makes electrical contact with this Ag layer. The bottom of the post or connector 2020 is electrically insulated (visible in FIG. 20C as the insulating layer 2015). A sacrificial layer of Ag/AgCl covers the Ag layer (and the insulated base of the post 2020), and a skin contacting layer of conductive hydrogel 2009 contacts the Ag/AgCl layer. FIG. 20C shows a slightly enlarged view of FIG. 20B, and schematically illustrates the current flowing from the electrical/mechanical connector 2020 into the hydrogel 2009 through the sacrificial Ag/AgCl layer 2007 and the Ag conductive layer 2005. In this example, the connection is configured so that the current does not flow directly into the Ag/AgCl 2007 or hydrogel 2009, but first passes from an upper surface of the connector that is in electrical contact with the Ag layer 2005 and then down into the Ag/AgCl layer 2007 and the hydrogel to contact the user. Thus, in this example, the portion of the connector base in contact with the silver/silver chloride layer is insulated 2015 so that the current primarily passes through the silver layer 2005.

In general, an electrically active region of an electrode apparatus may include a nonconsumptive conducting layer (e.g., 2005 in FIGS. 20A-20C), a consumptive conducting layer (e.g., 2007 in FIGS. 20A-20C), and a conductive hydrogel layer (e.g., 2009 in FIGS. 20A-20C). In some embodiments, the consumptive layer may be a buffer layer disposed between the nonconsumptive layer and the hydrogel layer. Further, the consumptive layer may extend beyond the boundary of the nonconsumptive layer at each edge of the nonconsumptive layer and may be configured to reduce hydrolysis in the hydrogel layer, such that the consumptive layer donates electrons for redox reactions. Examples of the conductive nonconsumptive layers may include silver, gold, copper, or any other type of conductive metal or non-metallic material, such as carbon or conductive polymers (e.g. poly(3,4-ethylenedioxythiophene). Preferably, the nonconsumptive and consumptive layers include silver. An important feature of the nonconsumptive layer is that any electrochemical reactions occurring in that layer do not cause the quality of the layer as an electrical conductor (i.e. impedance) to change during a transdermal (e.g., transcranial) stimulation. This feature ensures that current delivered to the layer is, for the most part, distributed evenly over its surface first before entering the consumptive layer. In some variations, an additional, higher impedance, layer is disposed between the nonconsumptive layer and the consumptive layer to more evenly spread current across the nonconsumptive layer before entering the higher impedance layer and, subsequently, the consumptive layer. In some embodiments, the nonconsumptive layer experiences reduced consumption, such that the nonconsumptive layer includes silver. Alternatively, the nonconsumptive layer may experience essentially zero consumption, such that the nonconsumptive layer includes carbon. In some embodiments, the nonconsumptive layer experiences reduced consumption since it does not include an anion that can be electrically consumed during electrical stimulation. The nonconsumptive layer may disperse the electrical current over its surface area before the current reaches the consumptive layer (i.e. there is lower impedance within the nonconsumptive layer than between the nonconsumptive layer and the consumptive layer). If the electrical current is not dispersed over the surface area of the nonconsumptive layer before reaching the consumptive layer, the consumptive layer may be over-consumed, such that AgCl becomes Ag(0) in a local area of the consumptive layer surface, causing uneven current distribution and the potential for local hydrolysis and local pH changes that may lead to discomfort in the subject. In embodiments, the consumptive layer is composed of a ratio of silver to silver chloride (Ag:AgCl) for efficient consumption and electrochemistry. Optimal ratios can be selected based on the charge balance of stimulation. In some embodiments, the ratio of Ag to AgCl particles in the consumptive layer may be between 40%:60% to 95%:5%, preferably 65%:35% to 85%:15%. Alternatively, the consumptive layer may include any suitable ratio of Ag:AgCl such that the chloride may be consumed but not depleted during an electrical stimulation session of sufficient length to induce a beneficial cognitive effect in a subject. The AgCl in the consumptive layer is consumed during alternating current or direct current stimulation (DC) because it acts as a sacrificial anode/cathode and is converted to Ag and a CL ion. The Ag+ in the consumptive layer is consumed during alternating current or direct current stimulation (DC) because it acts as a sacrificial anode/cathode and is converted to AgCl. In some embodiments, if the consumptive layer does not fully cover the dermal side of the nonconsumptive layer, the current may travel directly to the hydrogel layer and cause a site of high current density, for example a current hotspot. In some embodiments, the conductive hydrogel layer 37, as shown in FIG. 6, ensures that the current is transmitted substantially evenly to the skin of a user. Further, the hydrogel layer creates a uniform connection between the multi-electrode assembly and the skin of a user.

Figure 20D:
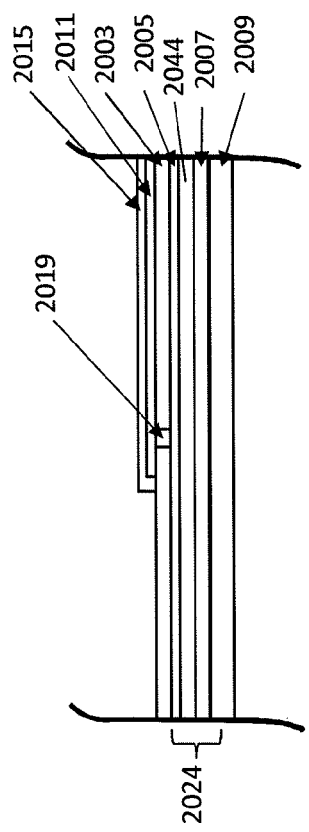
FIG. 20D illustrates another example (not to scale) of a section view though an active region of an electrode fed by a conductive trace; in this example, the active region includes a weakly insulating layer (e.g., a thin carbon layer between the silver and silver chloride layers).
Figure 20F:
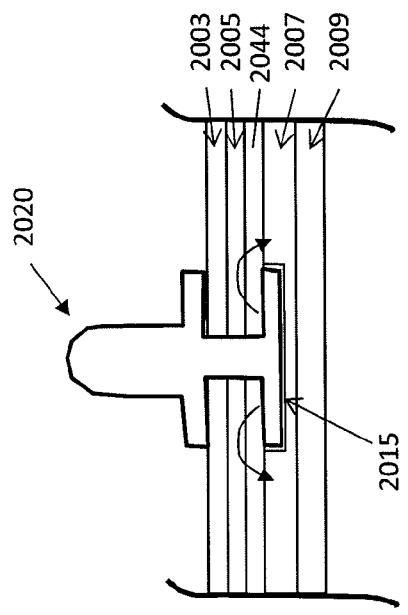
FIG. 20F is a slightly enlarged view of FIG. 20E.
Figure 20E:
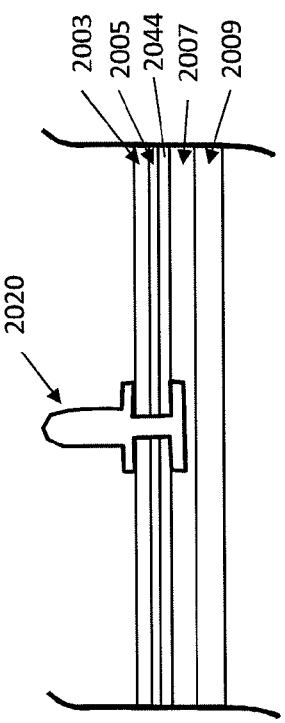
FIG. 20E shows a section view though an active region directly connected to a (snap) connector for coupling to a neurostimulator and including a weakly insulating layer (e.g., carbon)

In any of the electrode apparatuses described herein, an additional layer may be positioned between the conductive layer in electrical contact with the connector (e.g., snap connector) and the sacrificial anode/cathode layer in contact with the hydrogel. The additional layer may be a material that is less conductive than the adjacent conductive metal (e.g., Ag) layer and sacrificial (e.g., Ag/AgCl) layer, or even a weakly insulating material. In this example, the material is carbon, although other materials may be used. In general this layer may be less conductive than the layers immediately above (e.g., Ag) and below (e.g., Ag/AgCl). For example, FIGS. 20D-20F illustrate another variation of section through an active region of an electrode apparatus, showing different regions that may be used to form the active region and including an additional carbon layer. In FIG. 20D, the electrode trace 2011 extends on a top surface of a substrate 2003 (such as a polymeric material appropriate for use in a flexible circuit). This trace 2011 may be insulated (e.g., by an insulating layer 2015). An opening through the flex circuit (e.g., hole 2019) may include a conductive material (e.g., carbon black, silver, etc.) making an electrical communication between the trace 2011 and a portion of the electrically active region 2024, that includes a layer of conductive metal (e.g., Ag) 2005, a layer (e.g., carbon) having a lower conductance than the adjacent layers 2044, a covering layer of sacrificial Ag/AgCl 2007 that completely covers the Ag layer and it itself covered by the carbon layer 2044, and an outer, skin contacting layer of hydrogel 2009 in electrical contact with the Ag/AgCl layer.

In any of the electrode apparatuses described herein, the first conductive layer (e.g., a Ag layer) connects to the connector (e.g., pin, snap, clamp, etc.) and thus the electrical stimulator. This first conductive layer is separated from the sacrificial layer (e.g., Ag/AgCl layer) that connects to the gel (e.g., hydrogel) by the intermediate, less conductive layer. This less conductive layer may also be referred to as a weakly conductive layer, a weakly insulating layer, or a more resistive layer (all in reference to the adjacent first conductive layer and sacrificial layer). In general, this weakly conductive layer has an electrical conductance that is lower than either the adjacent first conductive layer or the sacrificial layer, although the electrical properties of the sacrificial layer may change with use. Thus, in general the weakly conductive layer may be more resistive than the first conductive layer; for example, the weakly conductive layer may have a resistivity that is greater than 3×, 4×, 5×, 6×, 7×, 8×, 9×, 10×, 15×, 20×, etc., the resistivity of the first conductive layer. In some variations, the resistance of the weakly conductive layer is greater than 5× the resistance of the first conductive layer that it covers. In general, each successive layer distal from the flexible substrate (i.e. a polymeric material appropriate for use in a flexible circuit) extends beyond the edge of the more proximal layer along its entire circumference to ensure that current cannot short between non-successive layers.

The weakly conductive layer may be formed of any appropriate material having the electrical properties described herein. For example, the weakly conductive layer may include carbon. For example, the weakly conductive material may be a polymeric material (including rubbers, polyvinyl chlorides, etc.) that is mixed with or incorporates carbon (e.g., carbon particles), etc.

FIG. 20E shows a partial section through a portion of another active region that is in electrical contact with a connector configured to couple with the electrical stimulator (e.g., the electrical and/or mechanical connector that contacts with the neurostimulator). The electrode may include an active region that is connected to the connector as shown in FIG. 20E and in detail in FIG. 20F. In this example, the active region of the electrode includes a contact (shown as a snap or pin) for connection to the electrical stimulator (e.g., neurostimulator). The connector 2020 penetrates the substrate 2003 as well as a layer of conductive material (shown as a conductive metal, e.g., Ag) 2005 and (in some variations) a layer of less conductive material (e.g., carbon) 2044, to make electrical contact with this Ag layer. The bottom of the post/connector 2020 is electrically insulated (shown in FIG. 20E as an insulating layer 2015). In this example, the Ag layer 2005 is separated from the sacrificial layer of Ag/AgCl 2007 by a less conductive (than either the Ag or Ag/AgCl layers) layer of carbon 2044, and a skin-contacting layer of conductive hydrogel 2009 contacts the Ag/AgCl layer 2007. FIG. 20F shows a slightly enlarged view of FIG. 20E, and schematically illustrates the current flowing from the electrical/mechanical connector 2020 into the hydrogel 2009 through the sacrificial Ag/AgCl layer 2007, less conductive layer 2044 and the conductive Ag layer 2005. In this example, current does not flow directly into the Ag/AgCl 2007 or hydrogel 2009, but first passes from an upper surface of the connector that is in electrical contact with the Ag layer 2005, either directly (not shown) or through the less conductive (e.g., carbon) layer 2044, and then flows down into the Ag/AgCl layer 2007 and the hydrogel to contact the user.

The optional less conductive layer 2044 described above may be helpful to spread the current as it moves from the highly conductive metal layer such as the Ag layer 2005 shown in FIGS. 20A-20F to the sacrificial layer (e.g., Ag/AgCl layer 2007) and into the hydrogel. In effect, this carbon layer (or similar less-conductive layer) may make the electrodes much more comfortable for the user to wear them, even when delivering relatively high intensity current signals, by improving the uniformity of current density and electrochemistry occurring in the consumptive layer and/or hydrogel.

In some embodiments, the electrode apparatus (flexible electrode assembly) may include an adhesive component. The adhesive component may be configured to couple the electrode apparatus to a body portion of a user or any other device or system. An adhesive component may surround and/or be adjacent to the boundary of the consumptive layer. In some embodiments, the adhesive component and the three layers (consumptive, nonconsumptive, and hydrogel) of the electrode active region may be substantially the same thickness, such that substantially all areas of the flexible assembly may be flush with the skin of a user. In some embodiments, the hydrogel layer may extend slightly beyond the adhesive layer so that the hydrogel makes a more uniform contact through slight compression when the electrode is adhered to the skin.

Alternatively, a flexible multi-electrode assembly may be pressed against or held to a body portion of a user. In some embodiments, the flexible transdermal multi-electrode assembly may be pressed against a body portion of the user using a headband, helmet, head scarf, or any other type of wearable device.

As described above, a single flexible transdermal assembly may include two or more electrodes (active regions) for electrical stimulation, such that only one assembly is required for electrical stimulation. For example, a user may stimulate a forehead region with a first electrode region (active region) on the flexible transdermal assembly and the back of the neck with a second electrode region (active region) on the same assembly to achieve the desired neuromodulation effect. Alternatively, the system may utilize two separate or separable assemblies, such that each assembly includes one electrode for electrical stimulation. In some embodiments, the two assemblies may be electrically coupled by a coupling element. For example, a user may position one assembly on the forehead and the second assembly on the back of the neck to achieve the desired neuromodulation outcome. Alternatively, any number of electrodes in each assembly may be used to achieve the desired neuromodulation effect. In some embodiments, any number of electrode areas on the same or different assemblies may be coupled by one or more traces. For example, one trace may couple an electrode area on the forehead to an electrode area on the back of the neck. Alternatively, one or more electrode areas on the same or different assemblies may be independently and directly controlled by the controller, for example through pogo pins as described above.

Returning now to FIGS. 15A and 15B, FIGS. 15A and 15B illustrate an example of a cantilever electrode for a TES neuromodulation system, having first and second transdermal assemblies (electrode portions 1505, 1503), and a coupling element (elongate body region 1507) to electrically couple the first and second assemblies. For example, the coupling element may couple to the first and second assemblies through a conductive connector, delivering current from the first surface to the second surface. In some embodiments, the connector may be insulated. For example, an adhesive component (e.g. a sticker, tape, adhesive paper, etc.) may be coupled to one end region of the connector. Alternatively, a material less conductive than the metal snap (e.g. using carbon filled plastic ABS) or an entirely non-conductive connector may be used. Alternatively, the connector may be coated with a non-conductive epoxy, latex, lacquer, or other non-conductive coatings. In some embodiments, the connector may include a snap system, such that the snap system includes a nonconductive eyelet. For example, the eyelet may be anodized aluminum. In some embodiments, the snap system may further include a female component and a male component. The female component may be coupled to the nonconsumptive layer of the electrode or alternatively to a conductive trace coupled to the electrode. The coupling element may include the male component on a distal end region of the coupling element, such that the female component is sized and configured to receive the male component. The male component may be coupled, for example, to the conductive layers of the electrode. In some embodiments, one of the male or female components may include a spring, or other suitable biased element, configured to maintain constant electrical contact between the male and female components. Further, the male component may include a ball head and a neck for tension between the parallel springs.

Alternatively, the coupling element may be coupled to the multi-electrode assembly independently of the connector. In some embodiments, the snap connector may be inserted upside down into part of the second surface, as shown in FIG. 12, such that the connector folds over the assembly to be snapped, fastened, or otherwise coupled to the electrode active region on the first surface. An advantage of this design is that the snap does not need to be riveted on the flexible circuit directly above an electrode area, yet by folding, can be positioned in this location to meet a connector (e.g. female) on a controller hardware assembly that snaps onto the flexible electrode assembly.

As mentioned above, a flexible multi-electrode assembly may further include one or more sensors, safety features, or identification features or devices embedded in the flexible substrate and/or integrated with the controller (e.g., in the neurostimulator). One or more sensors may include an accelerometer, thermometer, gyroscope, GPS, pH sensor, one or more biosensors, or any other type of sensor. One or more safety features may include an automatic off trigger, for example when the current reaches a certain threshold, when the temperature and/or pH of the device exceeds a threshold, or when the controller does not contain enough power to complete an entire TES session. One or more identification features may include a Bluetooth beacon, an RFID tag, a barcode, a near-field communication device, a biometric sensor for reading, for example a fingerprint of a user, or any other type of identification feature or device, including the capacitive identification system described above.

Figure 21:
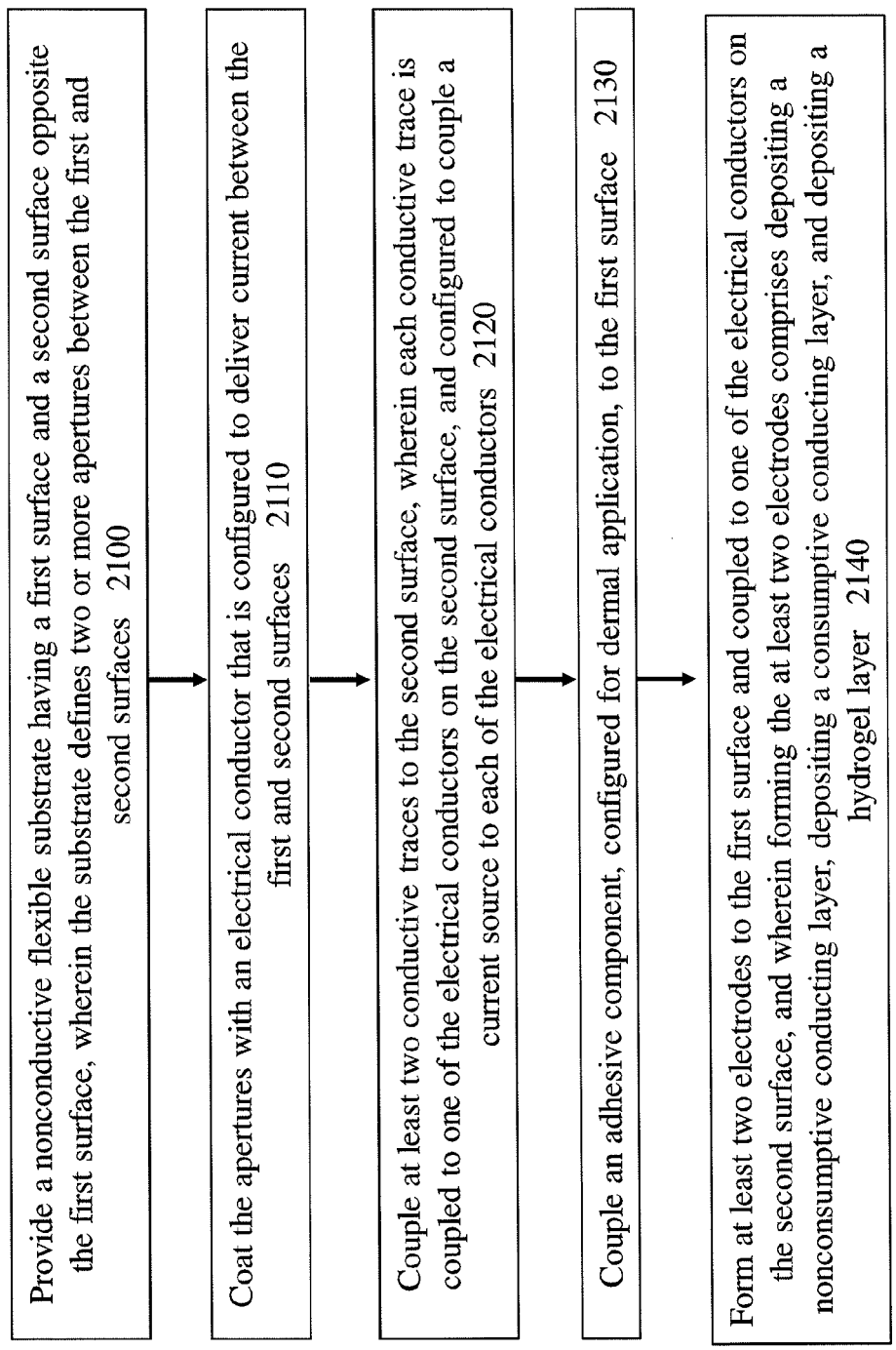
FIG. 21 schematically illustrates one method of forming an electrode apparatus such as a cantilever electrode apparatus.

FIG. 21 illustrates one method of making a flexible electrode apparatus as described herein. In this example a non-conductive flexible substrate 2100 having a first surface and a second surface opposite the first surface and two or more apertures between the first and second surfaces may be coated so that the apertures are at least partially filled (and more preferentially completely filled) with an electrical conductor that is configured to deliver current between the first and second surfaces 2110. Two or more conductive traces may then be formed on the second surface, such that each conductive trace is coupled to one of the electrical conductors on the second surface, and configured to couple a current source to each of the electrical conductors 2120; an adhesive component, configured for dermal application, may then be placed (e.g., coated) to the first surface 2130; and at least two electrodes may be formed or connected to the first surface and coupled to the one of the electrical conductors on the second surface 2140. Connecting or forming the at least two electrodes may include depositing a nonconsumptive conducting layer, depositing a consumptive conducting layer, and depositing a hydrogel layer, such that the consumptive layer is a buffer layer disposed between the nonconsumptive layer and the hydrogel layer that extends beyond the boundary of the nonconsumptive layer at each edge of the nonconsumptive layer and is configured to reduce hydrolysis in the hydrogel layer.

A preferred embodiment of manufacturing a flexible electrode apparatus for electrical stimulation to modulate a cognitive function may therefore generally include forming two or more apertures through a nonconductive flexible substrate having a first surface and a second surface opposite the first surface. In general, the flexible substrate may include polyimide, volara foam, or any other type of nonconductive material. The flexible substrate may be poured, dispersed, or otherwise positioned in a mold. The mold may include two or more protrusions, such that the flexible substrate, once set, includes two or more apertures. The flexible substrate in the mold may be thermoset and/or cured (e.g. form cross-links) by heat, a chemical reaction, and/or irradiation. In some embodiments, the cured flexible substrate may include a higher melting temperature than the temperature used to cure it. Thus, the cured flexible substrate may not be re-melted and/or deformed with the application of low intensity heat, such as the low intensity heat experienced during electrical stimulation. In some embodiments, additional components may be positioned in the flexible substrate before curing the flexible substrate, such that the additional components are embedded in the flexible substrate. The apertures formed in the flexible substrate may function to electrically connect the second surface with the first surface, such that the first surface may deliver electrical stimulation to a body portion of a user, as described above.

An alternative manufacturing process, as shown in FIG. 21, may use a flexible substrate cut, severed, or otherwise carved from a large sheet or the flexible substrate may be poured, dispersed, or otherwise positioned in a mold. Flexible substrate may include two electrode areas and a thin structure that has at least one conductive trace on the first (nondermal) side (or in an internal layer insulated on both dermal and nondermal sides) for delivering current from a snap connector to a portion of the flexible substrate containing a rear electrode pad. Electrode layers may be printed on the first (dermal facing) side of the flexible substrate. Hydrogel pieces having the same or very similar shape to the electrode areas may be placed over them. Adhesive regions adjacent to or surrounding a hydrogel and electrode area may also be placed on the first dermal facing side of the flexible assembly. The first, second, and third sheets may be bonded, glued, or otherwise fastened together to form the flexible multi-electrode assembly, such that the second sheet includes the first and second surfaces, as described above, conductive connections to an electrical stimulation controller may be made with male studs of snap connectors riveted through flexible substrate layers. Each snap connector is conductively connected to one of the electrode areas either directly or via a conductive path printed on the second (nondermal facing) side of the flexible substrate (or in an internal layer insulated on both dermal and nondermal sides). Further, the nonconsumptive and consumptive layers may be deposited in the opening of the first adhesive sheet, so that the hydrogel layer overlies it as shown in FIG. 20. In some embodiments, the second and third sheets may further include apertures for electrical conduction.

A method of manufacturing a flexible transdermal multi-electrode assembly for electrical stimulation of a neural target may include step 2110, which recites coating the apertures with an electrical conductor that is configured to deliver current between the first and second surfaces. In some embodiments, the apertures may be coated, silkscreened, painted, or printed with a conductive metal. For example, the conductive metal may include gold, silver, copper, aluminum, or any other type of conductive material. Once coated, the apertures may function to deliver current from the conductive traces on the second surface to the electrode(s) on the first surface. Alternatively, a pogo pin may be positioned in the aperture to connect the first and second surfaces.

A method of manufacturing a flexible transdermal multi-electrode assembly for electrical stimulation of a neural target may include coupling at least two conductive traces to the second surface, such that each conductive trace is coupled to one of the electrical conductors on the second surface, and configured to couple a current source to each of the electrical conductors. The conductive traces may be coupled to the second surface by printing, silk-screening, soldering, welding, gluing, or any other type of coupling process. The conductive trace may be positioned in proximity to a conductive aperture and in communication with the electrical conductors coating the aperture. In some embodiments, multiple conductive traces may be electrically connected to the same electrode, such that each trace electrically controls a subset (e.g. electrode area) of the electrode, as described above.

Further, a method of manufacturing a flexible transdermal multi-electrode assembly for electrical stimulation of a neural target may include coupling an adhesive component, configured for dermal application, to the first surface. The adhesive component may be adhered, secured, coupled, fastened, bonded, or otherwise attached to the flexible substrate adjacent to and/or surrounding the electrodes. In some embodiments, an adhesion promoter may be required to couple the adhesive component to the flexible substrate. Once coupled to the flexible substrate, the adhesive component may be flush with and/or not extend beyond the height of the other components coupled to the flexible substrate. Further, in some embodiments, the adhesive component may include a protective layer on the skin facing side, such that a user would need to peel the protective layer off before adhering the adhesive component to a body portion of the user. The protective layer may include plastic, synthetic rubber-like material, wax paper, or any other type of material that can be removably detached from the adhesive without significantly reducing dermal adhesion.

A method of manufacturing a flexible transdermal multi-electrode assembly for electrical stimulation of a neural target may also include forming and/or bonding at least two electrodes to the first surface and coupling them to one of the electrical conductors on the second surface, such that the step of bonding the at least two electrodes further includes depositing a nonconsumptive conducting layer, depositing a consumptive conducting layer, and depositing a hydrogel layer, such that the consumptive layer is a buffer layer disposed between the nonconsumptive layer and the hydrogel layer that extends beyond the boundary of the nonconsumptive layer at each edge of the nonconsumptive layer and is configured to reduce hydrolysis in the hydrogel layer. The nonconsumptive and consumptive layers may be printed or silk-screened on the flexible substrate. The silver ink in the nonconsumptive and consumptive layers may include 60-70% silver solids plus ethylene glycol and additional solvents. The ethylene glycol and additional solvents are flashed off while drying each of the layers after depositing each of the layers. Alternatively, other methods of printing the silver on the flexible substrate may be used. In some embodiments, the method may further include applying an adhesion promoter to enhance the coupling of the nonconsumptive and consumptive layers to the flexible substrate.

In use, any of the electrode apparatuses described herein may be connected to the user for neuromodulation. For example, an electrode assembly may be connected to a body portion of a user, before or after being coupled to a neurostimulator so that at least two electrodes of the electrode apparatus are coupled through one or more mechanical and/or connectors. As mentioned, the connectors connecting the electrode apparatus and the wearable neurostimulator may be located on just one side region (one end) of the neurostimulator so that the opposite end region of the neurostimulator may be cantilevered relative to the attachment point and allowed to move slightly thereby adjusting for different user body shapes and sizes. The neurostimulator may then electrically stimulate through the at least two electrodes, such that the neurostimulator delivers stimulation waveforms (or an ensemble of waveforms as discussed above) to the at least two electrodes for transdermal electrical stimulation and modification of the user's cognitive state. The method preferably functions to stimulate neural pathways, the brain, and/or nerves of a user using electrical stimulation delivered by a flexible electrode apparatus and neurostimulator.

Thus, neuromodulation using a multi-electrode assembly may include adhering a multi-electrode assembly to a body portion of a user to position a multi-electrode assembly on a body portion of a user such that the user may begin a transdermal or transcranial electrical stimulation protocol. In some embodiments, the system includes a single assembly containing two or more electrodes sized, configured, stimulated and positioned, as described herein, for achieving the desired neuromodulation effect. In some embodiments, the two or more electrodes within one assembly may include two or more electrode areas, such that the two or more electrode areas may be differentially stimulated to achieve different neuromodulation outcomes with one assembly, as described above. Alternatively, in some embodiments, the system comprises two or more assemblies, each containing at least one electrode for achieving the desired neuromodulation effect. The user may position the adhesive component on the first surface of the multi-electrode assembly, and press, stick, or otherwise secure the adhesive component to a body portion. In some embodiments, a user may remove a protective layer from the adhesive component before securing the adhesive component to a body portion of the user.

In some embodiments, the multi-electrode assembly may include sensors or other detectors that may detect a location or position of the multi-electrode assembly on the user. The multi-electrode assembly may begin delivering stimulation waveforms as soon as it is positioned in the correct location or position. Alternatively, the multi-electrode assembly may prevent a user from positioning the multi-electrode assembly in an inappropriate or incorrect location, such that the multi-electrode assembly may not deliver stimulation waveforms until it is repositioned or relocated.

Neuromodulation using a multi-electrode assembly may include coupling a controller to the at least two electrodes of the multi-electrode assembly through one or more connectors. The neurostimulator may be coupled to the multi-electrode assembly through a coupling element that couples the neurostimulator to the connectors on the electrode apparatus, as described above. Alternatively, the neurostimulator may be embedded in the flexible substrate (i.e. circuit components such as resistors, capacitors, current sources, microcontroller, switches, etc.) and electrically coupled to the electrodes in the electrode apparatus, such that all components are self-contained in the flexible substrate.

Neuromodulation using an electrode assembly may include electrically stimulating the at least two electrodes with the neurostimulator, such that the neurostimulator delivers stimulation waveforms to the at least two electrodes for transdermal/transcranial electrical stimulation. This may deliver stimulation waveforms to the electrode apparatus from the neurostimulator. Stimulation waveforms may include one or more waveforms selected from the group including: constant direct current; pulsed direct current stimulation (also referred to as pulsed monophasic alternating current stimulation); pulsed direct current stimulation with a constant direct current offset; alternating current stimulation (also referred to as biphasic alternating current stimulation); pulsed biphasic stimulation; or combined direct current stimulation and alternating current stimulation (also referred to as biased alternating current stimulation).

In some variations, any waveform described above can be combined in series or in parallel (i.e. concurrently) to create a hybrid waveform, or ensemble waveform. In embodiments, any waveform described above can be added, subtracted, convolved, or otherwise amplitude modulated. Moreover, in embodiments, any waveform above can have its amplitude ramped using linear, exponential, or another ramp shape including by one or more controllers that the user may manually adjust during stimulation.

The stimulation waveforms may include constant direct current stimulation above 3 mA maximum intensity. Alternatively, a constant direct current stimulation may be of any suitable maximum intensity such that a cognitive effect is induced. The stimulation waveforms may include a pulsed direct current stimulation above 5 mA (e.g., above 7 mA, etc.). Alternatively, a pulsed biphasic stimulation may be of any suitable magnitude such that a cognitive effect is induced. The stimulation waveforms may include an alternating current stimulation above 2 mA maximum intensity. Alternatively, an alternating current stimulation may be of any suitable maximum intensity such that a cognitive effect is induced. The stimulation waveforms may include a biased alternating current stimulation with a direct current offset less than 1.5 mA and maximum alternating current amplitude above 3 mA. Alternatively, the direct current offset and the maximum alternating current amplitude may be of any suitable magnitude such that a cognitive effect is induced. The values of the direct current offset and the maximum alternating current amplitude for the biased alternating current stimulation may be in any combination to achieve the desired stimulation waveform.

In some embodiments, using alternating current stimulation or pulsed direct current stimulation, pulses can comprise square waves, sine waves, sawtooth waves, triangular waves, rectified (unimodal) waves, pulse-width modulated, amplitude-modulated, frequency-modulated, or other pattern of alternating current waveform. For preferred embodiments using alternating current stimulation or pulsed biphasic or unimodal stimulation, a primary frequency of stimulation is between 0.5 Hz and 1 MHz; optionally between 650 Hz and 50 kHz; optionally between 650 Hz and 20 kHz; and optionally between 750 Hz and 20 kHz. Alternatively, the primary frequency stimulation may be in any suitable range such that a cognitive effect is induced.

In some embodiments, for pulsed biphasic stimulation and alternating current stimulation, the maximum intensity delivered to a subject transcranially is generally greater than 3.0 mA; optionally greater than 3.5 mA; optionally greater than 4 mA; optionally greater than 5 mA; optionally greater than 7.5 mA; optionally greater than 10 mA; optionally greater than 15 mA; and optionally greater than 20 mA. Alternatively, the maximum intensity may be of any suitable maximum intensity such that a cognitive effect is induced. In preferred embodiments using pulsed direct current stimulation and/or alternating current stimulation, efficacious peak current intensities are generally between about 3 mA and about 25 mA.

In some embodiments, for constant direct current stimulation, the maximum intensity delivered to a subject transcranially is greater than 3.0 mA; optionally greater than 3.5 mA; optionally greater than 4 mA; optionally greater than 5 mA; optionally greater than 7.5 mA; and optionally greater than 10 mA. Alternatively, the maximum intensity may be of any suitable maximum intensity such that a cognitive effect is induced.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of attaching an electrical stimulator to a user's head using an electrode apparatus formed of a flat substrate extending in a plane having a first electrode portion and a second electrode portion, a first active region on a back of the substrate in the first electrode portion, and a second active region on the back of the substrate in the second electrode portion, wherein the first and second electrode portions are connected by a connecting region of the substrate that extends in a path that is 2 inches or longer, the method comprising:
  adhesively securing the first active region of the electrode apparatus to the user's head in a first location;
  bending the connecting region out of the plane;
  adhesively securing the second active region of the electrode apparatus to the user's head in a second location; and
  coupling a wearable electrical stimulator to a first and second connector extending proud from the first electrode portion at a region that is off-center on a bottom of the wearable electrical stimulator so that the wearable electrical stimulator is worn on the user in the first location, allowing one end region of the electrical stimulator to be held securely while an opposite end region may move, wherein the wearable electrical stimulator is coupled either before or after adhesively securing the first active region of the electrode apparatus to the user's head.

2. The method of claim 1, wherein adhesively securing the first active region comprises adhesively securing the first active region to the user's temple.

3. The method of claim 1, wherein adhesively securing the second active region comprises adhesively securing the second active region to the user's neck or to the skin behind the user's ear.

4. The method of claim 1, wherein coupling the wearable electrical stimulator comprises securing the wearable electrical stimulator to the first electrode portion in a cantilevered attachment.

5. The method of claim 1, wherein coupling the wearable electrical stimulator to the first and second connector extending proud from the first electrode portion comprises snapping the wearable electrical stimulator onto the first and second connectors wherein the first and second connectors are separated from each other by between about 0.7 and 0.8 inches.

6. The method of claim 1, wherein coupling the wearable electrical stimulator to the first and second connector comprises snapping the wearable electrical stimulator onto the first and second connectors.

7. The method of claim 1, wherein adhesively securing the first active region comprises attaching a hydrogel on the first active region against the user's head in the first location.

8. The method of claim 1, wherein coupling the wearable electrical stimulator comprises connecting an underside of the wearable electrical stimulator to the first and second connectors to make an electrical contact with the wearable electrical stimulator and the first and second active regions.

9. A method of attaching an electrical stimulator to a user's head using an electrode apparatus formed of a flat substrate extending in a plane having a first electrode portion and a second electrode portion, a first active region on a back of the substrate in the first electrode portion, and a second active region on the back of the substrate in the second electrode portion, wherein the first and second electrode portions are spaced apart and connected by a connecting region of the substrate that extends in a path that is 2 inches or longer, the method comprising:
  adhesively securing the first active region of the electrode apparatus to the user's head in a first location;
  bending the connecting region out of the plane;
  adhesively securing the second active region of the electrode apparatus to the user's head in a second location; and
  coupling a back surface of a wearable electrical stimulator to a first connector and to a second connector that both extend proud from the first electrode portion, so that the wearable electrical stimulator cantilevers from the first electrode portion and is secured to the first electrode portion at a first back surface region of the wearable electrical device while a second back surface region of the wearable electrical device is not secured and is free to move relative to the first electrode portion, wherein the wearable electrical stimulator is coupled either before or after adhesively securing the first active region of the electrode apparatus to the user's head.

10. The method of claim 9, wherein adhesively securing the first active region comprises adhesively securing the first active region to the user's temple.

11. The method of claim 9, wherein adhesively securing the second active region comprises adhesively securing the second active region to the user's neck or to the skin behind the user's ear.

12. The method of claim 9, wherein coupling the back surface of the wearable electrical stimulator to the first and second connector comprises snapping the wearable electrical stimulator onto the first and second connectors, wherein the first and second connectors are separated from each other by between about 0.7 and 0.8 inches.

13. The method of claim 9, wherein coupling the back surface of the wearable electrical stimulator to the first and second connector comprises snapping the wearable electrical stimulator onto the first and second connectors.

14. The method of claim 9, wherein coupling the back surface of the wearable electrical stimulator further comprises making electrical contact between the wearable electrical stimulator and the first and second active regions through the first and second connectors.

15. The method of claim 9, further comprising applying electrical stimulation from the wearable electrical stimulator between the first active region and the second active region.

16. A method of attaching an electrical stimulator to a user's head using an electrode apparatus formed of a flat substrate extending in a plane having a first electrode portion and a second electrode portion, a first active region on a back of the substrate in the first electrode portion, and a second active region on the back of the substrate in the second electrode portion, wherein the first and second electrode portions are connected by a connecting region of the substrate that extends in a path that is 2 inches or longer, the method comprising:
  adhesively securing the first active region of the electrode apparatus to the user's head in a first location;
  bending the connecting region out of the plane;
  adhesively securing the second active region of the electrode apparatus to the user's head in a second location; and coupling a wearable electrical stimulator to an electrical and mechanical connector extending proud from the first electrode portion so that the wearable electrical stimulator cantilevers from the first electrode portion and is secured to the first electrode portion at a first back surface region of the wearable electrical device while a second back surface region of the wearable electrical device is not secured and is free to move relative to the first electrode portion, wherein the wearable electrical stimulator is coupled either before or after adhesively securing the first active region of the electrode apparatus to the user's head.

17. The method of claim 16, wherein adhesively securing the first active region comprises adhesively securing the first active region to the user's temple.

18. The method of claim 16, wherein adhesively securing the second active region comprises adhesively securing the second active region to the user's neck or to the skin behind the user's ear.

19. The method of claim 16, wherein coupling the wearable electrical stimulator to the electrical and mechanical connector comprises snapping the wearable electrical stimulator onto the mechanical and electrical connector.

* * * * *